US008937096B2

(12) United States Patent
Smith-Swintosky et al.

(10) Patent No.: US 8,937,096 B2
(45) Date of Patent: *Jan. 20, 2015

(54) USE OF BENZO-FUSED HETEROCYLE SULFAMIDE DERIVATIVES FOR THE TREATMENT OF MANIA AND BIPOLAR DISORDER

(75) Inventors: Virginia L. Smith-Swintosky, Hatfield, PA (US); Allen B. Reitz, Lansdale, PA (US)

(73) Assignee: Janssen Pharmaceutica NV, Beerse (BE)

(*) Notice: Subject to any disclaimer, the term of this patent is extended or adjusted under 35 U.S.C. 154(b) by 1888 days.

This patent is subject to a terminal disclaimer.

(21) Appl. No.: 11/612,222

(22) Filed: Dec. 18, 2006

(65) Prior Publication Data

US 2007/0155826 A1    Jul. 5, 2007

Related U.S. Application Data

(60) Provisional application No. 60/751,493, filed on Dec. 19, 2005.

(51) Int. Cl.
*A61K 31/335* (2006.01)
*A61K 31/44* (2006.01)
*A61K 31/33* (2006.01)
*A61K 31/353* (2006.01)
*A61K 31/357* (2006.01)

(52) U.S. Cl.
CPC ............ *A61K 31/353* (2013.01); *A61K 31/357* (2013.01)
USPC ........... 514/450; 514/452; 514/463; 514/349; 514/183

(58) Field of Classification Search
USPC .......... 514/450, 452, 463, 349, 183, 433, 360
See application file for complete search history.

(56) References Cited

U.S. PATENT DOCUMENTS

| | | |
|---|---|---|
| 2,527,861 A | 10/1950 | Walter |
| 3,143,549 A | 8/1964 | Lafferty et al. |
| 3,318,952 A | 5/1967 | Houlihan |
| 3,383,414 A | 5/1968 | Houlihan |
| 3,539,573 A | 11/1970 | Schmutz |
| 3,621,096 A | 11/1971 | Prange et al. |
| 4,513,006 A | 4/1985 | Maryanoff et al. |
| 4,539,413 A | 9/1985 | Mouzin et al. |
| 4,710,500 A | 12/1987 | Perregaard |
| 4,804,663 A | 2/1989 | Kennis et al. |
| 4,831,031 A | 5/1989 | Lowe, III et al. |
| 4,879,288 A | 11/1989 | Warawa et al. |
| 5,112,838 A | 5/1992 | Perregaard et al. |
| 5,158,952 A | 10/1992 | Janssen et al. |
| 5,192,785 A | 3/1993 | Lo et al. |
| 5,194,446 A | 3/1993 | Lo et al. |
| 5,212,326 A | 5/1993 | Meade |
| 5,229,382 A | 7/1993 | Chakrabarti et al. |
| 5,238,945 A | 8/1993 | Perregaard |
| 5,242,942 A | 9/1993 | Costanzo et al. |
| 5,258,402 A | 11/1993 | Maryanoff |
| 5,273,993 A | 12/1993 | Lo et al. |
| 5,312,925 A | 5/1994 | Allen et al. |
| 5,384,327 A | 1/1995 | Constanzo et al. |
| 5,387,700 A | 2/1995 | Maryanoff et al. |
| 5,731,348 A | 3/1998 | Gu et al. |
| 5,753,693 A | 5/1998 | Shank |
| 5,753,694 A | 5/1998 | Shank |
| 5,760,007 A | 6/1998 | Shank et al. |
| 5,780,650 A | 7/1998 | Furukawa et al. |
| 5,935,933 A | 8/1999 | Shank et al. |
| 5,998,380 A | 12/1999 | Ehrenberg et al. |
| 6,071,537 A | 6/2000 | Shank |
| 6,150,419 A | 11/2000 | Fairbanks et al. |
| 6,187,338 B1 | 2/2001 | Caruso et al. |
| 6,191,163 B1 | 2/2001 | Coltrell |
| 6,211,241 B1 | 4/2001 | Islam et al. |
| 6,319,903 B1 | 11/2001 | Carrazana et al. |
| 6,322,503 B1 | 11/2001 | Sparhawk, Jr. |
| 6,323,236 B2 | 11/2001 | McElroy |
| 6,391,877 B1 | 5/2002 | Islam et al. |
| 6,503,884 B1 | 1/2003 | Ehrenberg et al. |
| 6,559,293 B1 | 5/2003 | Almarsson et al. |
| 6,562,865 B1 | 5/2003 | Codd et al. |
| 6,583,172 B1 | 6/2003 | Shank |
| 6,627,653 B2 | 9/2003 | Plata-Salaman et al. |
| 6,852,701 B2 | 2/2005 | Plata-Salaman et al. |
| 6,852,738 B2 | 2/2005 | Jones et al. |
| 6,949,518 B1 | 9/2005 | Chu |
| 2001/0008889 A1 | 7/2001 | Caruso et al. |
| 2002/0015713 A1 | 2/2002 | Murdock et al. |

(Continued)

FOREIGN PATENT DOCUMENTS

| | | |
|---|---|---|
| CA | 2 416 647 A | 1/2003 |
| DE | 1211166 | 2/1966 |

(Continued)

OTHER PUBLICATIONS

MacDonald et al. (CNS Drugs, 2002, 16(8): 549-562).*
Walden et al. (Neuropsychobiology, 1998, 38: 181-84).*
Mula et al. ("Psycopharmacology of topiramate: from epilepsy to bipolar disorder" in Neuropsychiatric Disease and Treatment 2006:2(4) 475-488).*
Chengappa et al "Topiramate as add-on treatment for patients with bipolar mania" in Bipolar Disorders, vol. 1, Issue 1, 42-53, Sep. 1999), Abstract attached.*
U.S. Appl. No. 11/154,443, Maryanoff Bruce E.
U.S. Appl. No. 11/154,386, McComsey David F.
U.S. Appl. No. 11/209,122, Maryanoff Bruce E.
U.S. Appl. No. 11/611,938, Smith-Swintosky.

(Continued)

*Primary Examiner* — Blessing M Fubara
(74) *Attorney, Agent, or Firm* — Hal B. Woodrow

(57) ABSTRACT

The present invention is a method for the treatment of mania and/or bipolar disorder comprising administering to a subject in need thereof a therapeutically effective amount of one or more novel benzo-fused heterocycle sulfamide derivatives of formula (I) and formula (II) as herein defined.

25 Claims, No Drawings

(56) References Cited

U.S. PATENT DOCUMENTS

| | | | |
|---|---|---|---|
| 2004/0073037 A1 | 4/2004 | Jones et al. | |
| 2004/0192690 A1* | 9/2004 | Buxton et al. | 514/242 |
| 2004/0253223 A1 | 12/2004 | Rodriguez | |
| 2005/0148603 A1 | 7/2005 | Jimenez et al. | |
| 2005/0282887 A1* | 12/2005 | McComsey et al. | 514/450 |
| 2006/0047001 A1 | 3/2006 | Parker et al. | |
| 2006/0241172 A1 | 10/2006 | Zhou et al. | |
| 2006/0270856 A1 | 11/2006 | Abdel-Magid | |
| 2006/0276528 A1 | 12/2006 | Parker et al. | |
| 2007/0155826 A1 | 7/2007 | Smith-Swintosky et al. | |
| 2007/0293440 A1 | 12/2007 | Smith-Swintosky et al. | |
| 2007/0293476 A1 | 12/2007 | Smith-Swintosky et al. | |
| 2009/0182141 A1 | 7/2009 | Abdel-Magid et al. | |
| 2009/0209634 A1 | 8/2009 | Smith-Swintosky | |
| 2009/0247617 A1 | 10/2009 | Abdel-Magid et al. | |
| 2009/0247618 A1 | 10/2009 | Ballentine et al. | |
| 2009/0318544 A1 | 12/2009 | Mehrman et al. | |
| 2010/0063138 A1 | 3/2010 | McComsey et al. | |

FOREIGN PATENT DOCUMENTS

| | | |
|---|---|---|
| DE | 2022370 | 12/1971 |
| DK | 9800727 A | 5/1998 |
| EP | 0138441 B1 | 4/1985 |
| EP | 0483881 B1 | 5/1992 |
| EP | 490689 | 6/1992 |
| EP | 498770 | 8/1992 |
| EP | 503440 A1 | 9/1992 |
| EP | 478954 | 10/2000 |
| EP | 1056733 | 12/2000 |
| EP | 1118610 | 7/2001 |
| GB | 1087602 | 10/1967 |
| GB | 1111706 | 5/1968 |
| RU | 2246727 | 4/2004 |
| RU | 2226357 | 8/2004 |
| WO | WO 94/14827 A1 | 7/1994 |
| WO | WO 95/17406 A1 | 6/1995 |
| WO | WO 96/06822 A1 | 3/1996 |
| WO | WO 97/13510 A1 | 4/1997 |
| WO | WO 97/19682 A1 | 6/1997 |
| WO | WO 97/19919 | 6/1997 |
| WO | WO 97/35584 A1 | 10/1997 |
| WO | WO 98/00123 | 1/1998 |
| WO | WO 98/00124 A1 | 1/1998 |
| WO | WO 98/00130 A2 | 1/1998 |
| WO | WO 98/00131 A1 | 1/1998 |
| WO | WO 98/06708 A1 | 2/1998 |
| WO | WO 98/07447 A1 | 2/1998 |
| WO | WO 98/15270 | 4/1998 |
| WO | WO 99/44581 A2 | 9/1999 |
| WO | WO 99/62522 | 12/1999 |
| WO | WO 00/01376 A2 | 1/2000 |
| WO | WO 00/07583 A2 | 2/2000 |
| WO | WO 00/42995 A2 | 7/2000 |
| WO | WO 00/42996 A2 | 7/2000 |
| WO | WO 00/49017 | 8/2000 |
| WO | WO 00/50020 A2 | 8/2000 |
| WO | WO 00/54588 A1 | 9/2000 |
| WO | WO 00/61137 | 10/2000 |
| WO | WO 00/61139 A1 | 10/2000 |
| WO | WO 00/61140 A1 | 10/2000 |
| WO | WO 00/66109 A2 | 11/2000 |
| WO | WO 00/76493 A1 | 12/2000 |
| WO | WO 01/13904 A2 | 3/2001 |
| WO | WO 01/76576 A2 | 10/2001 |
| WO | WO 02/03984 | 1/2002 |
| WO | WO 02/07821 A | 1/2002 |
| WO | WO 02/09694 | 2/2002 |
| WO | WO 02/30881 | 4/2002 |
| WO | WO 02/089785 | 11/2002 |
| WO | WO 02/096424 A1 | 12/2002 |
| WO | WO 2004/014352 | 2/2004 |
| WO | WO 2004/093912 A1 | 4/2004 |
| WO | WO 2004/092116 A1 | 10/2004 |
| WO | WO 2004/096771 A1 | 11/2004 |
| WO | WO 2004/098584 A1 | 11/2004 |
| WO | WO 2005/020917 A2 | 3/2005 |
| WO | WO 2006/007435 | 1/2006 |
| WO | WO 2006/007436 | 1/2006 |
| WO | WO 2006/010008 A1 | 1/2006 |
| WO | WO 2006/010750 A1 | 2/2006 |
| WO | WO 2006/023861 A1 | 3/2006 |
| WO | WO 2006/127184 | 11/2006 |
| WO | WO 2007/075695 | 7/2007 |
| WO | WO 2007/075698 | 7/2007 |
| WO | WO 2007/075717 | 7/2007 |
| WO | WO 2007/075751 | 7/2007 |
| WO | WO 2007/075752 | 7/2007 |
| WO | WO 2007/075833 | 7/2007 |
| WO | WO 2007/075834 | 7/2007 |
| WO | WO 2007/092086 | 8/2007 |
| WO | WO 2007/095615 | 8/2007 |
| WO | WO 2007/095618 | 8/2007 |
| WO | WO 2007/098486 | 8/2007 |
| WO | WO 2007/137167 | 11/2007 |
| WO | WO 2009/089210 | 7/2009 |
| WO | WO 2009/120191 | 10/2009 |
| WO | WO 2009/120192 | 10/2009 |

OTHER PUBLICATIONS

U.S. Appl. No. 11/611,961, Reitz Allen B.
U.S. Appl. No. 11/612,071, Reitz Allen B.
U.S. Appl. No. 11/612,146, Reitz Allen B.
U.S. Appl. No. 11/612,174, Smith-Swintosky.
U.S. Appl. No. 11/612,202, Reitz Allen B.
U.S. Appl. No. 11/612,249, Reitz Allen B.
U.S. Appl. No. 11/673,705, Smith-Swintosky.
U.S. Appl. No. 11/673,709, Smith-Swintosky.
U.S. Appl. No. 11/673,713, Smith-Swintosky.
U.S. Appl. No. 11/673,723, Smith-Swintosky.
PCT International Search Report, PCT/US2005/029814, Nov. 9, 2005, U.S. Appl. No. 11/209,122.
PCT International Search Report, PCT/US2005/021513, Sep. 27, 2005, U.S. Appl. No. 11/154,443.
PCT International Search Report, PCT/US2005/021515, Jun. 16, 2005, U.S. Appl. No. 11/154,386.
PCT International Search Report, PCT/US2006/048681, Jul. 5, 2007, U.S. Appl. No. 11/611,938.
U.S. Appl. No. 11/673,977, Smith-Swintosky.
U.S. Appl. No. 11/673,987, Smith-Swintosky.
U.S. Appl. No. 11/673,998, Smith-Swintosky.
U.S. Appl. No. 11/674,011, Smith-Swintosky.
U.S. Appl. No. 11/674,021, Smith-Swintosky.
U.S. Appl. No. 11/677,717, Fawzy Nagy.
U.S. Appl. No. 60/883,442, Smith-Swintosky.
Maryanoff et al.: Anticonvulsant O-Alkyl Sulfamates 2,3:4,5-Bis-O-(1-methylethylidene)-betas-D-fructopyranose Sulfamate and Related Compounds, J.Med. Chem., vol. 30, No. 5, 1987, pp. 880-887.
Maryanoff et al.: "Comparison of Sulfamates and Sulfamide Groups for the Inhibition of Carbonci Anhydrase-II by Using Topiratmate as a Structural Platform", J. Med. Chem, vol. 48, No. 6, 2004, pp. 1941-1947.
Levy RH et al., eds. Antiepileptic Drugs. 3$^{rd}$ ed. New York: Raven Press, 1989:85-102.
CA 835894-69-4 Sulfamide (1,3-benzodioxo1-2-ylmethyl).
CA PLUS 835894-67-2 Sulfamic acid (1,3-benzodioxo1-2-ylmethyl ester).
CA PLUS 835894-65-0 Sulfamide [(3, 4-dihydro-2H-1-benzopyran-2-yl) methyl].
CA PLUS 835894-63-8 Sulfamic acid (3,4-dihydro-2H-1-benzopyran-2-yl)methyl ester.
Malatynska et al., "Submissive behavior in mice as a test for antidepressant drug activity", Neuroscience and Biobehavioral Review, 82 (2005) 306-313.
Malatynska et al., "Dominant-submissive behavior as models of mania and depression", Neuroscience and Biobehavioral Review, 29 (2005) 715-737.
Ghaemi et al., Soc. of Bio. Psychiatry, (1999) vol. 45, 137-144.

(56) References Cited

OTHER PUBLICATIONS

Stoll et al., Harvard Rev. Psychiatry, Jul./Aug. 1996, vol. 4, No. 2, 77-89.
Rygula et al., "Anhedonia and motivational deficits in rats: Impact of chronic social stress", Behavioral Brain Research, 162 (2005) 127-134.
Scozzafava A et al, "Modulaton of Carbonic Anhydrase Activity and Its Applications in Therapy", Expert Opinion on Therapeutic Patents 2003 United Kingdom, vol. 14, No. 5 (2004) pp. 667-702, XP002331413, ISSN:1354-3776.
Besag et al. "Behavioural Effects of the New Anticonvulsants" Drug Safety, Adis Press, Auckland, NZ, vol. 24, No. 7, 2001, pp. 513-536.
PCT International Search Report, PCT/US2006/048448 dated Jul. 11, 2007.
Aeberli, P. et al. "Neuropharmacological Investigation of N-Benzylsulfamides", Journal of Medicinal Chemistry, Jul. 1967, vol. 10, No. 4, pp. 636-642.
Ambrosini, P.J., Psychiatr. Serv. 2000, 51, 627-633.
American Diabetes Association, "Definition and Description of Diabetes Mellitus", Diabetes Care, Jan. 2006; p. S43-S48, vol. 29 Supplement 1.
Ananth, J., Psychother. Psychosom. 1998, 67, 61-70.
Angehagen, Mikael et al., "Does topiramate (TPM) have protective effects on astroglia cells and neurons in primary cortical cultures", Epilepsia, (1998) vol. 39, No. Suppl 6, pp. 44, XP000923162 abstract 2.050.
Ayata et al., "Suppression of cortical Spreading Depression in Migraine Prophylaxis", Ann Neurol 2006; 59:652-661.
Barry et al. Current status of the utilization of antiepipleptic treatments in mood, anxiety and aggression: drugs and devices, Jan. 2004, 35, 1.
Beck-Nielsen H., "In Vivo Glucose Metabolism, Insulin Secretion and, Insulin Action in Europids with Non-insulin-dependent Diabetes Mellitus (NIDDM) and Their First-degree Relatives", Diabet Med Sep. 1996;13(9 Suppl 6):S78-84.
Berman, R.M. et al., Depress. Anxiety 1997, 5, 154-164.
Breslau et al., "The impact of migraine. Epidemiology, risk factors, and co-morbidities" Neurology, 2001;56:S4-S12 (Abstract only).
Burton et al. Anti-epileptic drugs for pain management. Pain, Symptom, Control and Palliative Care, 2001, vol. 1, No. 2.
Ca 835894-69-4 Sulfamide (1,3-benzodioxo1-2-ylmethyl) (2005).
Cadieux, R.J., Am. Fam. Physician 1998, 58, 2059-2062.
Calabrese, J.R. et al., Eur. Neuropsychopharmacol. 1999, 9, S109-S112.
Calabresi et al., "Antiepileptic drugs in migraine: from clinical aspects to cellular mechanisms", Trends in Pharmacological Sciences, vol. 28, No. 4, 188-195 (2007).
Caumo A., "Insulin Sensitivity from Meal Tolerance Tests in Normal Subjects: A Minimal Model Index", J Clin Endocrinol Metab, 85(11):4396-402 2000.
Cavaletti G et al: "Experimental peripheral neuropathy induced in adult rats by repeated intraperitoneal administration of Taxal", Exper Neurol 133:64-72, 1995.
Chaplan SR et al: "Quantitative assessment of tactile allodynia in the rat paw". J Neurosci Meth, 53:55-63, 1994.
Crooke et al, Abstract, Topiramate Improves Glycemic Control Independent of Weight Loss in ob/ob Mice.diabetes. A Journal of the American Diabetes Association, Abstract Book 61st Scientific Sessions Friday, Jun. 22-Tuesday Jun. 26, 2001, 2158-PO, A513.
Demarest et al, Abstract, Topiramate Improves Glucose Tolerance and May Improve Insulin Sensitivity in Animal Models of Type 2 Diabetes Mellitus, diabetes, A Journal of the American Diabetes Association, Abstract Book 61st Scientific Sessions Friday, Jun. 22-Tuesday Jun. 26, 2001, 1254-P, A302.
Diamond et al, "Practical Approaches to Migraine Management", 2002, CNS Drugs, 16(6), pp. 385-403.
Dickenson et al. Neurobiology of neuropathic pain: mode of action of anticonvulsants. European Journal of Pain, 2002, 6 (Suppl. A): 51-60, 2002.

Dinneen S.F., "The Postprandial State: Mechanism of Glucose Intolerance", Diabet Med Aug. 1997;14 Suppl 3:S19-24.
Drach, B.S. et al.:"N-1,2,2,2,-tetra-chloroethyl-N',N'-dimethylsulphamide". Journal of Organic Chemistry of the USSR., vol. 13, No. 7, Jul. 1977, pp. 1289-1294, XP008067470.
Dressler et al., Benzodiazepine in geriatric patients . . . , Abstract, Anaesthesiologie und reanimation, 1996, vol. 21/5, pp. 136-138.
Drug Facts and Comparison (1995 Edition, pp. 1607).
Dursun, S.M. et al., "Accelerated weight loss after treating refractory depression with fluoxetine plus topiramate: possible mechanisms of action?", The Canadian Journal of Psychiatry, vol. 46, No. 3, pp. 287-288, 2001.
Edwards, K.R. et al, Efficacy and safety of topiramate in the treatment of painful diabetic neuropathy: a double-blind placebo-controlled study ADIS Title: Topiramate: therapeutic use: Neurogenic pain; In patients with diabetic neuropathy: Neurology 54 (Suppl. 3): 81 Apr. 11, 2000.
Edwards, et al., Evaluation of Topiramate in the Management of Painful Diabetic Neuropathy. Presented at: 18th Annual Meeting of the American Pain Society; 1998, Fort Lauderdale, FL.
Emancipator K., "Laboratory Diagnosis and Monitoring of Diabetes Mellitus", Am J Clin Pathol, 112(5):665-74 1999.
Erfurth, Andreas et al., "Bupropion as add-on strategy in difficult-to-treat bipolar depressive patients", Neuropsychobiology, vol. 45, No. Sup 1, pp. 33-36, 2002.
Fakhoury et al., Epilepsy Behay. Aug. 2007, abstract.
Flatters, SJL et al: "Acetyl-L-carnitine prevents and reduces paclitaxel-induced painful peripheralneuropathy", Neurosci Lett 397:219-223, 2006.
Gareri, P. et al, Progress in Neurobiology 61, 2000, 353-396.
Garonna, F. et al., "Topiramate in the treatment of overweight/obese binge eaters ADIS Title: Topiramate: therapeutic use; Obesity; In patient with binge eating disorders" International Journal of Neuropsychopharmacology 3(Suppl 1): 299: Jul. 2000 XP001030426 Bassano dG Vicenza Italy, whole document.
Goldberg R.G., "Prevention of Type 2 Diabetes", Med Clin North Am, Jul. 1998;82(4):805-21.
Gorelick D A, "Pharmacological treatment" Recent Developments in Alcoholism, vol. 11, 1993, p. 413-427, XP00913482 p. 417.
Gorelick et al., Drugs 2004: 64(14), pp. 1547-1573.
Grond et al., "Weak Opiods—an educational substitute for morphine?", Current Opinion in Anaesthesiology, vol. 11, No. 5, 1998, pp. 559-565 XP00982759.
Groop L., "Characterization of the Prediabetic State", Am J Hypertension; Sep. 1997;10(9 Pt 2):172S-180S.
Guillaume et al., "Glial contribution to seizure: Carbonic anhydrase activity in epileptic mammalian brain" Epilepsia, 1991, vol. 32, No. 1, 1991, pp. 10-15.
Haffner S.M., "Impaired Glucose Tolerance, Insulin Resistance and Cardiovascular Disease", Diabetic Medicine, Aug. 1977;14 Suppl 3:S12-8.
Haffner S.M., "The Prediabetic Problem: Development of Non-Insulin-Dependent Diabetes Mellitus and Related Abnormalities", J Diabetes Complications, Mar.-Apr. 1997; 11(2):69-76.
Harrison's Principles of Internal Medicine, Isselbacher et al. eds. McGraw-Hill, Inc., New York, 1994, p. 69.
Harrison's Principles of Internal Medicine, vol. 2, 23d ed., Ed by Isselbacher, Braunwald, Wilson, Martin, Fauci and Kasper, McGraw-Hill Inc New York City, 1994, p. 2275.
Hatzinger, M. et al., Wien. Med. Wochenschr. 1999, 149, 511-514.
Hauner H, "Managing type 2 diabetes mellitus in patients with obesity," Treatments in Endocrinology, 2004, 3(4), 223-232 (only abstract provided).
Headache Classification Committee of the International Headache Society. Cephalalgia 1988;8 Suppl 7:1-96.
Hering et al., "Sodium valproate in the treatment of cluster headache", Cephalalgia (Sep. 1989) 9(3) pp. 195-198.
Huisman, M. et al.:"Synthesis of N-(diemthylsulphamoyl)aldimines, a new type of aldimine derivative". Synthetic Communications, vol. 27, No. 6, 1997, pp. 945-952.
Jay et al., "Epilepsy, Migraine and EEG Abnormalities in Children: a Review & Hypothesis," Journal of Head and Face Pain, abstract, vol. 22, Issue 3, pp. 110-114, 1982.

(56) References Cited

OTHER PUBLICATIONS

Joffe, R.T. et al., Arch. Gen. Psychiatry 1993, 50, 397-393.
Johns Hopkins Clinical Trial of Topiramate for Cocaine Addiction (ClinicalTrials.gov), 2009.
Johnson, BA: "Progress in the development of topiramate for treating alcohol dependence: From a hypothesis to a proof-of-concept study" Alcoholism: Clinical and Experimental Research 2004 United States, vol. 28, No. 8, 2004, pp. 1137-1144.
Johnson, SA CNS Drugs, 2005. vol. 19, No. 1 0, pp. 873-896.
Kawasaki, "Structural and functional analysis of pancreatic islets preserved by pioglitazone in *db/db* mice", Am J Physiol Endocrinol Metab; 2004, p. E510-E518, doi 10.1152/ajpendo.00128.2004.
Keck, P et al, "Valproate and carbamazepine in the treatment of panic and post traumatic stress disorders, withdrawals states . . . " J Clin Psychopharm, vol. 12, No. 1, p. 36S-41S, 1992.
Kent, J.M., Lancet 2000, 355, 911-918.
Ketter, T.A. et al., J. Clin. Psychiatry 1995, 56, 471-475.
Keung W.M. et al, "Daidzin and daidzein suppress free-choice ethanol intake by Syrian golden hamsters" Proc Natl Acad Sci, vol. 90, p. 1008-10012, Nov. 1993.
Klinger et al., "Inhibition of carbonic anhydrase-II by sulfamate and sulfamide groups: An investigation involving direct thermodynamic binding measurements" Journal of Medicinal Chemistry, vol. 49, No. 12, Jun. 15, 2006, pp. 3496-3500.
Kohno, H. et al.: "A Novel Synthesis of Isoquinolines Containing an Electron Withdrawing Substitute". Heterocycles, vol. 51, No. 1, 1999, pp. 103-117, XP008052600.
Kralinsky E.A. Tramal in the treatment of pain in children with malignancies, Klinicka Onkologie, vol. 7, No. 6, 1994, pp. 182-185 (See English Abstract provided).
Kunkler et al., "Hippocampal Spreading Depression Bilaterally Activates the Caudal Trigeminal Nucleus in Roadent", Hippocampus 13:835-844 (2003).
Kuzniecky et al., "Topiramate increases cerebral GABA in healthy humans", Neurology (Aug. 1998) 51(2) pp. 627-629.
Kyowa Hakko, "Topiramate" Drugs of the Future, ES, Barcelona, vol. 21, No. 4, Jan. 1, 1996; p. 463-465.
Langtry H.D. et al, "Topiramate, A review of its pharmacodynamic and pharmacokinetic properties and clinical efficacy in the management of epilepsy" Drugs, (1997) 54/5 pp. 752-773, XP002179441.
Lydiard, R.B. et al., J. Clin. Psychiatry 1998, 59, Suppl. 18, 10-17.
Maryanoff, B.E.et al.: "Structure-Activity Studies on Anticonvulsant Sugar Sulphmates Related to Topiramate. Enhanced Potency with Cyclic Sulphate Derivatives". Journal of Medicinal Chemistry, vol. 41, No. 8, 1998, pp. 1315-1343.
Mathew, Ninan T., MD, et al, "Prophylaxis of Migraine, Transformed Migraine, and Cluster Headache with Topiramate" Headache (2002), (42)796-803.
Mathew, N. T. "Antiepileptic Drugs in Migraine Prevention", 2001, Headache, Nov./Dec. Suppl 2001, pp. S18-S24.
Mazzotta et al., J Headache Pain, 2004 5:S67-S70.
McElroy, S.L. et al., "A pilot trial of adjunctive topiramate in the treatment of bipolar disorder ADIS Title: Topiramate: therapeutic use; Bipolar disorder: A pilot trial of adjunctive treatment" retrieved from STN Database Accession No. 1998:39968 XP00217779443 Abstract & XXIST CINP Congress (Jul. 12, 1998) pp. 281 (Poster) University of Cincinnati College of Medicine, Cincinnati, OH.
Meldrum B. et al., "Excitatory amino acid neurotoxicity and neurodegenerative disease" TIPS, vol. 11, 1990, pp. 379-387, XP000915223.
Migraine: Treatments and drugs, by Mayo Clinic Staff, http://www.mayoclinic.com/health/migraineheadache/DS00120/DSECTION=treatments-and-drugs, 2009.
Moller, H.J. et al., Eur. Arch. Psychiatry Clin. Neurosci. 2000, 250, 57-68.
Moskowitz, M.A., "The Neurobiology of Vascular Head Pain", Annals of Neurology, vol. 16, Issue 2, pp. 157-168, 1984.
Mueller T I, "A double-blind, placebo-controlled pilot study of carbamazepine for the treatment of alcohol dependence", Alcoholism Clin Exp Res, vol. 21, No. 1, 1997, p. 86-92.
Mula et al., "The role of anticonvulsant drugs in anxiety disorders: a critical review of the evidence" Journal of Clinical Psychopharmacology, Williams and Wilkins, vol. 1. 27, No. 3, 2007, pp. 263-272.
Myers, R.D., "New Drugs for the Treatment of Experimental Alcoholism", Alcohol, vol. 11, No. 6, 1994, p. 439-451.
Nemeroff, C.B., Depress. Anxiety 1996-1997, 4, 169-181.
Nickel et al., Journal of Affective Disorders, vol. 87(2-3), 2005, pp. 243-252.
Nies et al., Goodman & Gilman's The Pharmacological Basis of Therapeutics, 9th Edition, pp. 43-62, 1996.
Olesen et al., "Spreading Cerebral Oligemia in Classical- and Normal Cerebral Blood Flow in Common Migraine", Department of Neuromedicine, Rigshospitalet 2100 Copenhagen, Denmark, Jan. 28, 1982 (Headache 22:242-248, 1982).
Olson et al [Editors]. Remington's Pharmaceutical Sciences, pp. 420-425, 1980.
Osborne et al, Abstract, Topiramate Improves Glycemic Control and Triglycerides in Animal Models 1 page The Posters were presented at the American Diabetes Association Conference held Jun. 22-26 in Philadelphia, diabetes, A Journal of the American Diabetes Association, Abstract Book 61st Scientific Sessions Friday, Jun. 22-Tuesday Jun. 26, 2001, 1255-P, A302.
Ottman et al., "Comorbidity of migraine and epilepsy", Neurology, 1994;44: 2105 (Abstract only).
Pansare, S.V. et al.: "Intramolecular Imine Cross-Coupling in Dibenzylidine Sulphamides; synthesis of unsymmetrical 1,2-diaryl ethanediamines". Tetrahedron Letters, vol. 37, No. 16, Apr. 15, 1006, pp. 2859-2862 (2005).
Pascual D et al: "A cannabinoid agonist, WIN55,212-2, reduces neuropathic nocicipetion induced by paclitaxel in rats" Pain 118:23-34, 2005.
Penovich et al., "Weight Loss in Patients Receiving Topiramate for Intractable Epilepsy", 1994, Neurology 44 (Suppl. 2) Abstract 309P, 46th Annual Meeting of the American Academy of Neurology, Washington, D.C.
Perry et al. "Sumatriptan: An Updated Review of its Use in Migraine", 1998, Drugs, vol. 55, No. 6, pp. 889-922.
Pini et al., "Anti-Epileptic Drugs in the Preventive Treatment of Migraine Headache: a Brief Review", (J. Headache Pain, 2001, 2:13-19.
Polomano et al: "A painful peripheral neuropathy in the rat produced by the chemotherapeutic drug, paclitaxel", Pain, 94:293-304, 2001.
Prado Lima, P.A.S. et al., "Topiramate in treatment-refractory depression" retrieved from STN Database accession No. 1999:61852 XP002179442 Abstract & 11th World Congress of Psychiatry (Aug. 6, 1999), vol. 2,00.126.
Raguraman, et al., "Effects of topiramate in alcohol dependence [2]" Australian and New Zealand Journal of Psychiatry, 2005 Australia, vol. 39, No. 8, 2005, pp. 736-737.
Ramlo-Halsted BA, "The Natural History of Type 2 Diabetes", Primary Care Dec. 1999;26(4):771-89.
Reis et al. Craving decrease with topiramate in outpatient treatment for cocaine dependence: an open label trial, Rev Bras Psiquiatr 2008;30(2):132-5.
Rogaswki et al., Nature Medicine, vol. 10, No. 7, Jul. 2004, pp. 685-692.
Rogawski et al., Nature Reviews Neuroscience, vol. 5 (1), 2004, pp. 553-564.
Rost et al., The effect of tramadol and other analgesics on the pain . . . , Abstract, Arzneim-Forsch. 1978, vol. 28 (1a0 pp. . . 181-183).
Rouillon, F., Eur. Neuropsychopharmacol 1999, 9 Suppl. 3, S87-S92.
Sanacora, G. et al., "Impairment of GAB Aergic transmission in depression: New Insights from neuroimaging studies", Critical Reviews in Neurobiology, (2000) 14/1 pp. 23-45, XP001029967, whole document.
Shank et al., "Examination of two independent kinetic assays for determining the inhibition of carbonic anhydrases I and II: Structure-activity comparison of sulfamates and sulfamides" Chemical Biology and Drug Design, vol. 68, No. 2, 2006, pp. 113-119.
Sharma K, McCue P, Dunn SR. Am J Physiol Renal Physiol. Jun. 2003;284(6):F1138-44.

(56) References Cited

OTHER PUBLICATIONS

Silberstein et al., "Migraine & Epilepsy", www.myepilepsy.com, 2002.
Sofuoglu et al., CNS Drugs 2005: 19(1), pp. 13-25.
Soledade et al.:"Toward the control of *Leptosphaeria maculans* Design, Synthesis, biological activity, and metabolism of potential detoxification inhibitors of the crucifer phytoalexin brassinin". Bioorganic & Medicinal Chemistry, vol. 14, No. 14, Apr. 17, 2006, pp. 4958-4979, XP005458688.
Stephen, Linda J. et al., "Lamotrigine and topiramate may be a useful combination", The Lancet, vol. 351, No. 9107, pp. 958-959, 1998.
Stephen, Linda J. et al., "Topiramate in Refractory Epilepsy: A Prospective Observational Study", Epilepsia, vol. 41, No. 8, pp. 977-980, 2000.
Storey et al, "Topiramate in Migraine Prevention: A Double Blind, Placebo-Controlled Study", 2001, Headache, 41, pp. 968-975.
Ten Have, R. et al.:"Novel Synthesis of 4(5)-monosubstituted imidazoles via cycloaddition of tosylmethyl isocyanide to aldimines". Tetrahedron, vol. 53, No. 33, Aug. 18, 1997, pp. 11355-11368, XP004106007.
Tenovuo, O. "Central Acetylcholinesterase Inhibitors in the Treatment of Chronic Traumatic Brain Injury—Clinical Experience in 111 Patients". Progress in Neuro-Psychopharmacology and Biological Psychiatry 2005 US, vol. 29, No. 1, Jan. 2005, pp. 61067. XP002431412.
The Merck Manual (1987), Merck Sharp & Dohme Research Laboratories, Rahway, NJ XP002144176, pp. 1351-1356.
The Merck Manual, 1999, Merck Research, Whitehouse Station, NJ XP002224345, Diabetes Mellitus, pp. 165-177.
Topiramate retrieved from STN Database Accession No. 1998:2562 XP002179444 Abstract & R&D Focus Drug News, Jul. 27, 1998.
Traube, W. et al.:"Zur Kenntnis des Sulfamids". Berichte der Deutschen Chemischen Gesellschaft, vol. 56, 1923, pp. 1656-1663, XP002393747.
Uhart et al., Addiction Biology, 14, pp. 43-64, 2008.
Uys et al., CNS Neurol Disord Drug Targets, 7(5), 2008, pp. 482-491.
Van Amerigen et al. Antiepileptic drugs in the treatment of anxiety disorders: Role in Therapy, Drugs, 2004, 64(19), 2199-2220.
Vandi, A., et al.: "Synthesis and Properties of Some N-Substituted Sulphamides", Journal of Organic Chemistry, vol. 26, No. 4, Apr. 1961, pp. 1136-1138, XP002394144.
Von Seggern, Randal L., et al, "Efficacy of Topiramate in Migraine Prophylaxis: A Retrospective Chart Analysis" Headache (2002), (42)804-809.
Waugh et al., "Topiramate: As Monotherapy in Newly Diagnosed Epilepsy" CNS Drugs, vol. 17, No. 13, 2003, pp. 985-992.
Wauquier A et al, "Topiramate: A potent anticonvulsant I the Amygdala-Kindled Rat" Epilepsy Research, NJ, Elsevier Science Publishers, Amsterdam, vol. 24, No. 2, Jun. 1, 1996, p. 73-77, XP002042953.
WebMD Medical News Epilepsy Drugs Fights Migraine, 2002, www.webmd.com/migraine-headaches/news/20020923/epilepsydruq-fights-migraine.
Weib, G. et al.: "Herstellung und Reaktionen von N-Monoalkylamidosulfonylchloriden" Liebigs Annalen Der Chemie, vol. 729, Dec. 1969, pp. 40-51, XP002187581 (see English Abstract provided).
Wheeler et al., "Topiramate-treated cluster headache", Neurology (Jul. 1999) vol. 53, No. 1 pp. 234-236.
Wheeler S.D., "Antiepileptic Drug therapy in Migraine Headache", Current Treatment Options Neurology, Sep. 2002; 4(5):383-394.
Wheeler, "Significance of migrainous features in cluster headache", Headache (1998) 38/7 pp. 547-551.
Whitehead, C.W. et al.: "Diuretics. II. Alkoxymercuration oby mixed anion sales of mercury". Journal of the American Chemical Society, vol. 80, No. 9, May 5, 1958, pp. 2182-2185, XP002393746.
Williams, Jr., J.W., et al., Ann. Intern. Med. 2000, 132, 743-756.
Winhusen et al. Drug and Alcohol Dependence 91 (207) 131-148, 2007.
Yang Y. et al., "Neuroprotection by delayed administration of topiratmate in rat model of middle cerebral artery embolization", Brain Research, vol. 804, No. 2, 1998, pp. 169-176, XP000921218.
York, DA et al, "Effects of Topirament on High Fat Diet-Induced Obesity", FASEB journal, Fed. of America Soc. For Experimental Biology, Bethesda, MD, US., vol. 14, No. 4, Apr. 2000. p. A431, XP000915192.
Young, WB et al, "Topiramate: a case series study in migraine prophylaxis" Cephalalgia (2002), (22)659-663.
Ziegler. E., et al.:"Zur Reaktivitat von C=Ndoppelbindungssytemen, VI. Reaktionen mit Sulfonamiden und Sulfamiden". Zeitschrift Fur Naturforschung, vol. 30B, 1975, pp. 951-953, XP008067475.
Alcaraz et al., Org. Lett., 2004, 6(16), pp. 2705-2708.
Beaudoin et al., J. Org. Chem., 2003, 68, pp. 115-119.
Birch et al., J. Med. Chem., 1999, 42, pp. 3342-3355.
Delgado et al., Tet Lett, 1988, 29(3), pp. 3671-3676.
Estave et al., Tet Lett, 2002, 43, pp. 1019-1021.
Gavernet et al., Bioorg & Med Chem., 2007, 15, pp. 5604-4516.
Hedayatullah et al., Phosphorus and Sulfur, 1985, 25(1), pp. 33-38.
Hirayama et al., Bioorg & Med Chem., 2002, 10, pp. 1509-1523.
Kim et al., Tet Lett, 23(14), pp. 1505-1508, 1982.
Kubicki et al., J Mol Struct., 2001, 531(1-3), p. 65-70.
Lee et al., Org. Chem 1990 55(25) pp. 6098-6104.
Muniz et al., SYNLETT, 2005, 1, pp. 149-151.
Nelson et al., J. Med. Chem., 1977, 20(7), pp. 880-885.
Nelson et al., J. Med. Chem., 1979, 22(9), pp. 1125-1127.
Nicolaou et al., Chem. Eur. J., 2004, 10, pp. 5581-5606.
Okada et al., Tet Lett, 2000, 41, pp. 7047-7051.
Park et al., J. Med. Chem., 2002, 45, pp. 5295-5302.
Winum et al., Org. Lett., 2001, 3(14), pp. 2241-2243.
Xu et al., SYNLETT, 2004, 11, pp. 1901-1904.
Zhong et al., J. Comb. Chem., 2004, 6, pp. 556-563.
Chemische Berichte 1959 92 pp. 509-513 (See English translation provided).
Agrawal et al., Bioorganic and Medicinal Chemistry, 11(2003), pp. 5353-5362.
Casini et al., Bioorganic and Medicinal Chemistry Letters, 13(2003), pp. 841-845.
Pasorekova et al., Journal of Enzyme Inhibition and Medicinal Chemistry, Jun. 2004, vol. 19(3), pp. 199-229.
Supuran et al., Curr. Med. Chem.—Cardiovascular and Hematological Agents, 2004, 2, pp. 49-68.
Supuran et al., Curr. Med. Chem.—Imm., Endoc. & Metab Agents, 2001, 1, 61-97.
Supuran et al., Exp. Opin. Ther. Patents, (2000), 10(5), pp. 575-600.
Supuran et al., Exp. Opin. Ther. Patents, (2002), 12(2), pp. 217-242.
Supuran et al., Medicinal Research Reviews, vol. 23, No. 2, pp. 146-189, 2003.
Thakur at al., Bioorganic and Medicinal Chemistry, 12(2004), pp. 789-793.
Behl et al., Endocrinology, vol. 138, No. 1, pp. 101-106, 1997.
Coyle et al., Science, vol. 262, Issue 5134, pp. 689-695, 1993.
Desagher et al., The Journal of Neuroscience, 1996, 16(8), pp. 2553-2562.
Tabner et al., The Journal of Biological Chemistry, vol. 280, No. 43, pp. 35789-35792, Oct. 28, 2005.
Taylor et al., Science, vol. 296, pp. 1991-1995 (2002).
New England Journal of Medicine, vol. 342:505-507, 2001.
Merck Manuals Online Medical Library, www.merck.com, 2007.
Cleeves et al., "Trazodone is ineffective in essential tremor", J. Neurol Nerusurg Psychiatry, 1990, 53:268-269.
Koller et al., "Essential Tremor Variants: Effect of Treatment", abstract, Clinical Pharmacology, 1987.
Robinson et al. "Pregablin not Effective for Essential Tremor", www.medpagetoday.com, 2009.
Handley and Mithani, Naunyn. Schmied. Arch. Pharmacol., 327, 1-5, 1984.
Aron et al., Neuropharmacology, 10, 459-469, 1971.
Meert et al., Pharmacol. Biochem. Behav.; 2005, 80(2), pp. 309-326.
Byrn et al., Pharmaceutical Research, Kluwer Academic Publishers, New York, NY, US, vol. 12, No. 7, 1995, pp. 945-954.

(56) References Cited

OTHER PUBLICATIONS

Jones et al. "Screening for Major Depression in Epilepsy with Common Self-Report Depression Inventories", Epilepsia, May 2005; 46(5):731-735.
Bernando, L., Prevention of epilepsy after head trauma: do we need drugs or a new approach?, 2003, Epilepsia, 44, (Suppl. 10), 27-33.
D'Ambrosio et al., Curr. Opin. Neurol. Dec. 2004; 17(6): 731-735.
Kane et al., Psychopharmacological Bulletin, vol. 24, pp. 62-67 (1988).
Kaplan & Sadock's Comprehensive Textbook of Psychiatry, Seventh Edition, vol. II, Lippincott Williams & Wilkins: Philadelphia, pp. 2467-2468, 2000.
Kaplan & Sadock's Comprehensive Textbook of Psychiatry, Seventh Edition, vol. II, Lippincott Williams & Wilkins: Philadelphia, pp. 2470-2471, 2000.
Physician's Desk Reference; Kaplan & Sadock's Comprehensive Textbook of Psychiatry, Seventh Edition, vol. II, Lippincott Williams & Wilkins: Philadelphia, pp. 2466-2467, 2000 (olanzapine).
Physician's Desk Reference; Kaplan & Sadock's Comprehensive Textbook of Psychiatry, Seventh Edition, vol. II, Lippincott Williams & Wilkins: Philadelphia, pp. 2456-2463, 2000 (clozapine).
Physician's Desk Reference; Kaplan & Sadock's Comprehensive Textbook of Psychiatry, Seventh Edition, vol. II, Lippincott Williams & Wilkins: Philadelphia, pp. 2463-2466, 2000 (risperidone).
Physician's Desk Reference; Kaplan & Sadock's Comprehensive Textbook of Psychiatry, Seventh Edition, vol. II, Lippincott Williams & Wilkins: Philadelphia, pp. 2469-2470, 2000 (quetiapine).
Harwood, AJ, Molecular Psychiatry (2005) 10,117-126.
Goodman and Gilman's The Pharmacological Basis of Therapeutics, Eleventh Edition, McGraw Hill, Hypnotics and Sedatives, Chapter 16, pp. 401-427 (2006).
Goodman and Gilman's The Pharmacological Basis of Therapeutics, Eleventh Edition, McGraw Hill, Hypnotics and Sedatives, Chapter 17, pp. 429-459 (2006).
Goodman and Gilman's The Pharmacological Basis of Therapeutics, Eleventh Edition, McGraw Hill, Hypnotics and Sedatives, Chapter 19, pp. 429-459 (2006).
Sullivan, P., Epilepsy & Behavior 7 (2005) S12-S17.
Notice of Allowance dated Mar. 20, 2012 in U.S. Appl. No. 11/209,122.
Notice of Allowance dated May 10, 2012 in U.S. Appl. No. 11/406,794.
Notice of Allowance dated Feb. 6, 2012 in U.S. Appl. No. 11/611,961.
Notice of Allowance dated May 23, 2012 in U.S. Appl. No. 11/611,961.
Notice of Allowance mailed Mar. 9, 2012 in U.S. Appl. No. 11/612,071.
Notice of Allowance mailed Apr. 25, 2012 in U.S. Appl. No. 11/612,146.
Interview Summary mailed Mar. 26, 2012 in U.S. Appl. No. 12/431,141.
Notice of Allowance mailed Apr. 16, 2012 in U.S. Appl. No. 11/612,202.
Notice of Allowance dated May 11, 2012 in U.S. Appl. No. 13/301,109.
Office Action mailed Mar. 30, 2012 in U.S. Appl. No. 11/750,600.
Interview Summary mailed Apr. 4, 2012 in U.S. Appl. No. 12/055,433.
Notice of Allowance dated May 11, 2012 in U.S. Appl. No. 12/349,184.
Notice of Allowance mailed Mar. 1, 2012 in U.S. Appl. No. 12/488,079.
Notice of Allowance mailed Mar. 28, 2012 in U.S. Appl. No. 12/502,472.
Brodie, M.S.; Pesold, C; Appel, S.B. Alcohol Clin Exp Res 1999, 23, pp. 1848-1852.
Edeh et al, (1987) Relationship between interictal psychopathology and the type of epilepsy. Results of a survey in general practice. Br J Psychiatry 151:95-101.
Ettinger et al., (2004) Depression and comorbidity in community-based patients with epilepsy or asthma. Neurology 63:1008-1014.
Forsgren et al., (1990) An incident case-referent study of epileptic seizures in adults. Epilepsy Res 6:66-81.
Hesdorffer et al. (2006) Depression and suicide attempt as risk factors for incident unprovoked seizures. Ann Neurol 59:35-41.
Hesdorffer et al. (2000) Major depression is a risk factor for seizures in older adults. Ann Neurol 47:246-249.
Jacoby et al. (1996) The clinical course of epilepsy and its psychosocial correlates: findings from a U.K. Community study. Epilepsia 37:148-161.
Kanner, AM., (2006) Epilepsy, suicidal behaviour, and depression: do they share common pathogenic mechanisms? Lancet Neurol 5:107-108.
Krampfl et al., The European Journal of Neuroscience; vol. 22, Issue: 1, pp. 10-20, 2005.
Ottman et al., Epilepsia, 52(2):308-315, 2011.
Scimemi et al., The Journal of Neuroscience: the official journal of Society for Neuroscience; vol. 25; Issue: 43, pp. 10016-10024, 2005.
Wise RA, Drug Alcohol Depend, 1998, 51, pp. 13-22.
Wise RA, NIDA Res Mono, 1984,50,pp. 15-33.
Office Action mailed Mar. 26, 2008 in U.S. Appl. No. 11/154,443.
Notice of Allowance mailed Dec. 31, 2008 in U.S. Appl. No. 11/154,443.
Notice of Allowance mailed Jun. 8, 2009 in U.S. Appl. No. 11/154,443.
Notice of Allowance mailed Oct. 9, 2009 in U.S. Appl. No. 11/154,443.
Notice of Allowance dated Feb. 9, 2010 in U.S. Appl. No. 11/154,443.
Notice of Allowance dated May 25, 2010 in U.S. Appl. No. 11/154,443.
Notice of Allowance dated Sep. 20, 2010 in U.S. Appl. No. 11/154,443.
Notice of Allowance dated Jan. 25, 2011 in U.S. Appl. No. 11/154,443.
Notice of Allowance dated May 4, 2011 in U.S. Appl. No. 11/154,443.
Notice of Allowance dated Aug. 12, 2011 in U.S. Appl. No. 11/154,443.
Office Action mailed Oct. 3, 2007 in U.S. Appl. No. 11/154,386.
Office Action mailed Jul. 9, 2008 in U.S. Appl. No. 11/154,386.
Notice of Allowance mailed Mar. 6, 2009 in U.S. Appl. No. 11/154,386.
Notice of Allowance mailed Sep. 10, 2009 in U.S. Appl. No. 11/154,386.
Notice of Allowance dated Feb. 23, 2010 in U.S. Appl. No. 11/154,386.
Notice of Allowance dated Oct. 22, 2010 in U.S. Appl. No. 11/154,386.
Office Action mailed Apr. 14, 2008 in U.S. Appl. No. 11/209,122.
Notice of Allowance mailed Oct. 30, 2008 in U.S. Appl. No. 11/209,122.
Office Action mailed Mar. 20, 2009 in U.S. Appl. No. 11/209,122.
Notice of Allowance mailed Sep. 24, 2009 in U.S. Appl. No. 11/209,122.
Notice of Allowance mailed Jan. 13, 2010 in U.S. Appl. No. 11/209,122.
Notice of Allowance mailed Jan. 11, 2011 in U.S. Appl. No. 11/209,122.
Notice of Allowance mailed Jun. 1, 2011 in U.S. Appl. No. 11/209,122.
Notice of Allowance mailed Oct. 18, 2011 in U.S. Appl. No. 11/209,122.
Office Action mailed Sep. 10, 2008 in U.S. Appl. No. 11/406,794.
Notice of Allowance dated Mar. 13, 2009 in U.S. Appl. No. 11/406,794.
Notice of Allowance dated Jul. 17, 2009 in U.S. Appl. No. 11/406,794.
Office Action mailed Nov. 2, 2009 in U.S. Appl. No. 11/406,794.
Notice of Allowance dated Mar. 17, 2010 in U.S. Appl. No. 11/406,794.
Notice of Allowance dated Jul. 1, 2010 in U.S. Appl. No. 11/406,794.

(56) References Cited

OTHER PUBLICATIONS

Notice of Allowance dated Nov. 29, 2010 in U.S. Appl. No. 11/406,794.
Notice of Allowance dated Mar. 14, 2011 in U.S. Appl. No. 11/406,794.
Notice of Allowance dated Jun. 30, 2011 in U.S. Appl. No. 11/406,794.
Corrected Notice of Allowance dated Jul. 20, 2011 in U.S. Appl. No. 11/406,794.
Notice of Allowance dated Oct. 4, 2011 in U.S. Appl. No. 11/406,794.
Notice of Allowance dated Jan. 17, 2012 in U.S. Appl. No. 11/406,794.
Office Action mailed Aug. 17, 2009 in U.S. Appl. No. 11/611,938.
Final Office Action mailed Feb. 25, 2010 in U.S. Appl. No. 11/611,938.
Office Action mailed May 2, 2008 in U.S. Appl. No. 11/611,961.
Final Office Action mailed Jan. 29, 2009 in U.S. Appl. No. 11/611,961.
Notice of Allowance dated Jun. 2, 2009 in U.S. Appl. No. 11/611,961.
Notice of Allowance dated Jan. 6, 2010 in U.S. Appl. No. 11/611,961.
Notice of Allowance dated Apr. 30, 2010 in U.S. Appl. No. 11/611,961.
Notice of Allowance dated Aug. 12, 2010 in U.S. Appl. No. 11/611,961.
Notice of Allowance dated Nov. 30, 2010 in U.S. Appl. No. 11/611,961.
Notice of Allowance dated Mar. 14, 2011 in U.S. Appl. No. 11/611,961.
Notice of Allowance dated Jul. 18, 2011 in U.S. Appl. No. 11/611,961.
Notice of Allowance dated Oct. 26, 2011 in U.S. Appl. No. 11/611,961.
Office Action mailed Nov. 26, 2008 in U.S. Appl. No. 11/612,071.
Final Office Action mailed Jun. 8, 2009 in U.S. Appl. No. 11/612,071.
Notice of Allowance mailed Oct. 11, 2011 in U.S. Appl. No. 11/612,071.
Final Office Action mailed Aug. 5, 2008 in U.S. Appl. No. 11/612,146.
Final Office Action mailed Oct. 29, 2009 in U.S. Appl. No. 11/612,146.
Office Action mailed Jan. 29, 2009 in U.S. Appl. No. 11/612,174.
Office Action mailed Jul. 11, 2011 in U.S. Appl. No. 12/431,141.
Final Office Action mailed Dec. 15, 2011 in U.S. Appl. No. 12/431,141.
Office Action mailed Mar. 30, 2009 in U.S. Appl. No. 11/612,202.
Office Action mailed Jan. 14, 2010 in U.S. Appl. No. 11/612,202.
Notice of Allowance mailed Jul. 29, 2010 in U.S. Appl. No. 11/612,202.
Notice of Allowance mailed Nov. 15, 2010 in U.S. Appl. No. 11/612,202.
Notice of Allowance mailed Mar. 4, 2011 in U.S. Appl. No. 11/612,202.
Notice of Allowance dated Sep. 19, 2011 in U.S. Appl. No. 11/612,202.
Notice of Allowance dated Jan. 4, 2012 in U.S. Appl. No. 11/612,202.
Office Action mailed Jul. 21, 2009 in U.S. Appl. No. 11/612,249.
Final Office Action mailed Jan. 28, 2010 in U.S. Appl. No. 11/612,249.
Office Action mailed Oct. 15, 2010 in U.S. Appl. No. 11/612,249.
Office Action mailed Apr. 22, 2011 in U.S. Appl. No. 11/612,249.
Office Action mailed Oct. 6, 2011 in U.S. Appl. No. 10/612,249.
Office Action mailed May 21, 2008 in U.S. Appl. No. 11/674,021.
Final Office Action mailed Jul. 31, 2009 in U.S. Appl. No. 11/674,021.
Notice of Allowance mailed Jun. 16, 2010 in U.S. Appl. No. 11/674,021.
Notice of Allowance mailed Dec. 15, 2010 in U.S. Appl. No. 11/674,021.
Notice of Allowance dated Aug. 22, 2011 in U.S. Appl. No. 11/674,021.
Office Action mailed Apr. 29, 2009 in U.S. Appl. No. 11/750,600.
Final Office Action mailed Dec. 16, 2009 in U.S. Appl. No. 11/750,600.
Final Office Action mailed Mar. 11, 2010 in U.S. Appl. No. 11/750,600.
Notice of Allowance mailed May 28, 2010 in U.S. Appl. No. 11/750,600.
Notice of Allowance mailed Dec. 15, 2010 in U.S. Appl. No. 11/750,600.
Office Action/Interview Summary dated Sep. 1, 2011 in U.S. Appl. No. 11/750,600.
Notice of Allowance dated Sep. 12, 2011 in U.S. Appl. No. 11/750,600.
Notice of Allowance dated Dec. 22, 2011 in U.S. Appl. No. 11/750,600.
Office Action mailed Jun. 24, 2009 in U.S. Appl. No. 12/055,433.
Final Office Action mailed Feb. 23, 2010 in U.S. Appl. No. 12/055,433.
Office Action mailed Sep. 22, 2010 in U.S. Appl. No. 12/055,433.
Office Action mailed Jun. 8, 2011 in U.S. Appl. No. 12/055,433.
Office Action mailed Dec. 22, 2011 in U.S. Appl. No. 12/055,433.
Office Action mailed May 26, 2011 in U.S. Appl. No. 12/055,695.
Office Action mailed Jul. 15, 2011 in U.S. Appl. No. 12/055,695.
Final Office Action mailed Nov. 21, 2011 in U.S. Appl. No. 12/055,695.
Office Action mailed Nov. 15, 2010 in U.S. Appl. No. 12/055,924.
Notice of Allowance mailed Apr. 12, 2011 in U.S. Appl. No. 12/055,924.
Office Action mailed Oct. 6, 2011 in U.S. Appl. No. 12/349,184.
Office Action mailed Jun. 1, 2010 in U.S. Appl. No. 12/488,079.
Notice of Allowance mailed Dec. 14, 2010 in U.S. Appl. No. 12/488,079.
Notice of Allowance mailed Jun. 21, 2011 in U.S. Appl. No. 12/488,079.
Notice of Allowance dated Nov. 1, 2011 in U.S. Appl. No. 12/488,079.
Office Action mailed Jul. 8, 2011 in U.S. Appl. No. 12/502,472.
Notice of Allowance dated Nov. 28, 2011 in U.S. Appl. No. 12/502,472.
O'Donnell et al., Chapter 15, "Drug Therapy of Depression and Anxiety Disorders", Goodman & Gilman's The Pharmacological Basis of Therapeutics, 12th Edition, 2011, pp. 397-415.
McNamara, J., Chapter 21, "Pharmacotherapy of the Epilepsies", Goodman & Gilman's The Pharmacological Basis of Therapeutics, 12th Edition, 2011, pp. 583-607.
Notice of Allowance dated Jul. 19, 2012 in U.S. Appl. No. 11/154,386.
Notice of Allowance dated Nov. 20, 2012 in U.S. Appl. No. 11/154,386.
Notice of Allowance dated May 8, 2013 in U.S. Appl. No. 11/154,386.
Notice of Allowance dated Aug. 29, 2013 in U.S. Appl. No. 11/154,386.
Notice of Allowance dated May 10, 2013 in U.S. Appl. No. 11/209,122.
Notice of Allowance dated Sep. 16, 2013 in U.S. Appl. No. 11/209,122.
Notice of Allowance mailed Dec. 24, 2012 in U.S. Appl. No. 11/611,938.
Notice of Allowance mailed Mar. 27, 2013 in U.S. Appl. No. 11/611,938.
Notice of Allowance dated Aug. 27, 2012 in U.S. Appl. No. 11/611,961.
Notice of Allowance dated Dec. 10, 2012 in U.S. Appl. No. 11/611,961.
Notice of Allowance dated Apr. 2, 2013 in U.S. Appl. No. 11/611,961.
Notice of Allowance mailed Jan. 22, 2013 in U.S. Appl. No. 11/612,071.
Notice of Allowance mailed Aug. 9, 2012 in U.S. Appl. No. 11/612,202.
Notice of Allowance mailed Nov. 26, 2012 in U.S. Appl. No. 11/612,202.

(56) References Cited

OTHER PUBLICATIONS

Notice of Allowance mailed Mar. 18, 2013 in U.S. Appl. No. 11/612,202.
Notice of Allowance mailed Jul. 9, 2013 in U.S. Appl. No. 11/612,202.
Notice of Allowance mailed Oct. 25, 2013 in U.S. Appl. No. 11/612,202.
Notice of Allowance mailed Oct. 16, 2013 in U.S. Appl. No. 13/301,109.
Final Office Action mailed Sep. 10, 2012 in U.S. Appl. No. 11/750,600.
Office Action mailed Mar. 14, 2013 in U.S. Appl. No. 11/750,600.
Final Office Action mailed Aug. 13, 2013 in U.S. Appl. No. 11/750,600.
Notice of Allowance mailed Jul. 8, 2013 in U.S. Appl. No. 11/612,071.
Notice of Allowance mailed Sep. 23, 2013 in U.S. Appl. No. 11/612,146.
Office Action mailed Jul. 19, 2013 in U.S. Appl. No. 12/431,141.
Office Action mailed May 23, 2013 in U.S. Appl. No. 12/055,433.
Notice of Allowance mailed Jun. 18, 2012 in U.S. Appl. No. 12/488,079.
Notice of Allowance mailed Oct. 10, 2012 in U.S. Appl. No. 12/488,079.
Notice of Allowance mailed Feb. 7, 2013 in U.S. Appl. No. 12/488,079.
Notice of Allowance mailed Mar. 27, 2013 in U.S. Appl. No. 12/488,079.
Notice of Allowance mailed Aug. 9, 2013 in U.S. Appl. No. 12/488,079.
Notice of Allowance mailed Jul. 16, 2012 in U.S. Appl. No. 12/502,472.
Notice of Allowance mailed Apr. 29, 2013 in U.S. Appl. No. 12/502,472.
Dib, Jean G., Current Medical Research and Opinion, 2004, 20, 12, p. 1857-1861.
Thienel et al., Acta Neurologica Scandinavica, 2004, 110, 4, p. 221-231.
Brandt et al., Neuropsychobiology, 1998, 38, pp. 202 to 203.
Tanimukai et al., International Pharmacopsychiatry, 1970, vol. 5, No. 1, pp. 35 to 43.
Keck et al., J. Clin. Psychiatry, 2002, 63 (suppl 4).
Remington's The Science and Practice of Pharmacy, 19th Edition, Published 1998, vol. I, pp. 371-375.
Remington's The Science and Practice of Pharmacy, 19th Edition, Published 1998, vol. II, pp. 2226-2241, see attached translation as provided from foreign agent in Colombia, detailing only portions of the article as cited by the Colombian examiner containing indications regarding the general procedures for manufacturing, isolating and purifying crystals and polymorphs.
Stella et al., Drugs, 29: 455-473 (1985).
Benjamin et al. J Biomol Screening, 2006, vol. 11, pp. 29-39.
Brown et al. Tetrahedron, 1987, vol. 43, pp. 4071-4078.
Dunham et al. J Am Pharm Assoc Sci Ed, 1957, vol. 46, pp. 208-209.
Ettinger et al. Neurotherapeutics, 2007, vol. 4, pp. 75-83.
Gavernet et al. Bioorg Med Chem 2007, vol. 15, pp. 1556-1567.
Gavernet et al. J Med Chem, 2009, vol. 52, pp. 1592-1601.
Gribkoff, V., Expert Opin Ther Pat., 2003 vol. 7, pp. 737-748.
Kohling, R., Epilepsia, 2002, vol. 43, pp. 1278-1295.
Kuzimski et al., Epilepsia, 2005, vol. 46, pp. 481-489.
Landmark, C., CNS Drugs, 2008, vol. 22, pp. 27-47.
Liu et al., Epilepsy Res, 2006, vol. 70, pp. 263-268.
Liu et al., Neuropharmacology, 2003, vol. 44, pp. 413-422.
Lombardo et al., Mol Brain Res, 1996, vol. 35, pp. 84-90.
Lothman et al., Epilepsy Res, 1988, vol. 2, pp. 356-366.
Lothman et al., Epilepsy Res, 1988, vol. 2, pp. 367-379.
Lukyanetz et al., Epilepsia, 2002, vol. 43, pp. 9-18.
Maryanoff et al, Drugs Future, 1989, vol. 14, pp. 342-344.
Maryanoff et al, J Med Chem, 2008, vol. 51, pp. 2518-2521.
Maryanoff et al., Curr Top Med Chem, 2009, vol. 9, pp. 1049-1062.
Maryanoff, B., J Med Chem, 2009, vol. 52, pp. 3431-3440.
Orloff et al., Proc Soc Exp Biol Med, 1949, vol. 70, pp. 254-257.
Parker et al., J Med Chem, 2009, vol. 52, pp. 7528-7536.
Rogawski et al., Nat Med, 2004, vol. 10, pp. 685-692.
Rogawski, M., Epilepsy Res, 2006, vol. 69, pp. 273-294.
Shank et al., CNS Neurosci Ther, 2008, vol. 14, pp. 120-142.
Shank et al., Epilepsia, 1994, vol. 35, pp. 450-460.
Shank et al., J Enzym Inh Med Chem, 2008, vol. 23, pp. 271-276.
Shingles et al., Anal Biochem, 1997, vol. 252, pp. 190-197.
Soderpalm, B., Eur J Pain, 2002, vol. 6, Suppl A, p. 3-9.
Swinyard et al., J Pharmacol Exp Ther, 1952, vol. 106, pp. 319-330.
Swinyard, E., Epilepsia, 1969, vol. 10, pp. 107-119.
Wang et al., Science, 1998 vol. 282, pp. 1890-1893.
White et al., Antiepileptic Drugs, 5th Ed., 2002, pp. 36-48.
White et al., Epilepsy Res, 1992, vol. 12, pp. 217-226.
White et al., Int Rev Neurobiol, 2007, vol. 81, pp. 85-110.
Winum et al., Expert Opin Ther Pat, 2006, vol. 16, pp. 27-47.
Zaremba et al., Pharmacol Rep, 2006, vol. 58, pp. 1-12.
Loscher, et al., Pharma. Rev., 62, 668-700 (2010).
Walker, et al., Brain, 125, 1937-1950 (2002).
McNamara et al. Analyses of the molecular basis of kindling development. Psychiatry and Clinical Neurosciences, 1995, 49, S175-S178.
Loscher et al. Antiepileptogenic effects of the novel anticonvulsant levetiracetam (ucb L059) in the kindling model of temporal lobe epilepsy. The Journal of Pharmacology and Experimental Therapeutics, vol. 284, No. 2, 1998, pp. 474-479.
Kinrys, G et al. Levetiracetam as Adjunctive Therapy for Refractory Anxiety Disorders. J. Clin. Psychiatry 68; Jul. 7, 2007: 1010-1013.
Kinrys, G et al. Leetiracetam or Treatment-Refractory Posttraumatic Stress Disorder J. Clin. Psychiatry 67:Feb. 2, 2006:211-214.
Zhang, W et al. Levetiracetam in social phobia: a placebo controlled pilot study. J. Psychopharm. 19(5) (2005) 551-553.
Nowack et al., Am J Physiol Cell Physiol, 299 C960-C967, 2010.
Otagiri et al., "Prodrug' in The New Drug Delivery System" (2000), CMC Publishing Co., Ltd., pp. 123-135 [translation of extracted portions from p. 124—subsection "2.2 Design of Prodrugs" and Table 1].
Polymorphism in pharmaceutical solids, 1999, edited by H.G. Brittain, Mercel Decker; Grant (chapter 1), p. 1-10 and Guillory (chapter 5), p. 183-226.
Caira, Topics in Current Chemistry 1998, 198, 163-208.
Notice of Allowance dated Dec. 16, 2013 in U.S. Appl. No. 11/154,386.
Notice of Allowance mailed May 7, 2014 in U.S. Appl. No. 11/154,386.
Notice of Allowance dated Feb. 20, 2014 in U.S. Appl. No. 11/209,122.
Notice of Allowance mailed Dec. 20, 2013 in U.S. Appl. No. 11/612,071.
Notice of Allowance mailed Mar. 31, 2014 in U.S. Appl. No. 11/612,146.
Final Office Action mailed Dec. 30, 3013 in U.S. Appl. No. 12/431,141.
Office Action mailed Feb. 4, 2014 in U.S. Appl. No. 11/612,249.
Final Office Action mailed Aug. 19, 2014 in U.S. Appl. No. 11/612,249.
Notice of Allowance mailed Mar. 18, 2014 in U.S. Appl. No. 13/301,109.
Office Action mailed Feb. 25, 2014 in U.S. Appl. No. 11/750,600.
Notice of Allowance mailed Jun. 10, 2014 in U.S. Appl. No. 11/750,600.
Final Office Action mailed Nov. 14, 2013 in U.S. Appl. No. 12/055,433.
Notice of Allowance mailed Nov. 8, 2013 in U.S. Appl. No. 12/488,079.
Notice of Allowance mailed Dec. 23, 2013 in U.S. Appl. No. 12/502,472.
Notice of Allowance mailed Apr. 24, 2014 in U.S. Appl. No. 12/502,472.

* cited by examiner

USE OF BENZO-FUSED HETEROCYLE SULFAMIDE DERIVATIVES FOR THE TREATMENT OF MANIA AND BIPOLAR DISORDER

CROSS REFERENCE TO RELATED APPLICATIONS

This application claims the benefit of U.S. Provisional Application 60/751,493, filed on Dec. 19, 2005, which is incorporated by reference herein in its entirety.

FIELD OF THE INVENTION

The present invention is directed to the use of benzo-fused heterocycle sulfamide derivatives for the treatment of mania and bipolar disorder.

BACKGROUND OF THE INVENTION

Bipolar disorder is psychiatric disorder characterized by unpredictable swings in mood from mania (or hypomania) to depression. Some patients suffer only from recurrent attacks of mania, which in its pure form is associated with increased psychomotor activity; excessive social extroversion; decreased need for sleep; impulsivity and impairment in judgment; and expansive, grandiose, and sometimes irritable mood. In severe mania, patients may experience delusions and paranoid thinking indistinguishable from schizophrenia. Half of patients with bipolar disorder present with a mixture of psychomotor agitation and activation with dysphoria, anxiety, and irritability. It may be difficult to distinguish mixed mania from agitated depression. In some bipolar patients (bipolar II disorder), the full criteria for mania are lacking, and the requisite recurrent depressions are separated by periods of mild activation and increased energy (hypomania). In cyclothymic disorder, there are numerous hypomanic periods, usually of relatively short duration, alternating with clusters of depressive symptoms that fail, either in severity or duration, to meet the criteria of major depression. The mood fluctuations are chronic and should be present for at least 2 years before the diagnosis is made.

Manic episodes typically emerge over a period of days to weeks, but onset within hours is possible, usually in the early morning hours. An untreated episode of either depression or mania can be as short as several weeks or last as long as 8 to 12 months, and rare patients have an unremitting chronic course. The term rapid cycling is used for patients who have four or more episodes of either depression or mania in a given year. This pattern occurs in 15% of all patients, almost all of whom are women. In some cases, rapid cycling is linked to an underlying thyroid dysfunction and, in others, it is iatrogenically triggered by prolonged antidepressant treatment. Approximately half of patients have sustained difficulties in work performance and psychosocial functioning.

Patients suffering from bipolar disorder typically complain of the following types of symptoms, depending on whether they are in a "manic" or "high" phase versus a "depressed" or "low" phase. In the manic phase symptoms include, but are not limited to (a) increased physical and mental activity and energy (b) heightened mood, exaggerated optimism and self-confidence; (c) excessive irritability, aggressive behavior; (d) decreased need for sleep without experiencing fatigue; (e) grandiose delusions, inflated sense of self-importance; (h) racing speech, racing thoughts, flight of ideas; (i) impulsiveness, poor judgment, distractibility; (j) reckless behavior and In the most severe cases, (k) delusions and hallucinations. In the manic phase symptoms include, but are not limited to (a) prolonged sadness or unexplained crying spells; (b) significant changes in appetite and sleep patterns; (c) irritability, anger, worry, agitation, anxiety; (d) pessimism, indifference; (e) loss of energy, persistent lethargy; (f) feelings of guilt, worthlessness; (g) inability to concentrate, indecisiveness; (h) inability to take pleasure in former interests, social withdrawal; (i) unexplained aches and pains and (j) recurring thoughts of death or suicide.

Bipolar disorder is common, affecting ~1% of the population in the United States. Onset is typically between 20 and 30 years of age, but many individuals report premorbid symptoms in late childhood or early adolescence. The prevalence is similar for men and women; women are likely to have more depressive and men more manic episodes over a lifetime.

Lithium carbonate is the mainstay of treatment in bipolar disorder, although sodium valproate and olanzapine are equally effective in acute mania, as is lamotrigine in the depressed phase. The response rate to lithium carbonate is 70 to 80% in acute mania, with beneficial effects appearing in 1 to 2 weeks. Lithium also has a prophylactic effect in prevention of recurrent mania and, to a lesser extent, in the prevention of recurrent depression. Serious side effects from lithium administration are rare, but minor complaints such as gastrointestinal discomfort, nausea, diarrhea, polyuria, weight gain, skin eruptions, alopecia, and edema are common.

In the treatment of acute mania, lithium is initiated at 300 mg bid or tid, and the dose is then increased by 300 mg every 2 to 3 days to achieve blood levels of 0.8 to 1.2 meq/L. Because the therapeutic effect of lithium may not appear until after 7 to 10 days of treatment, adjunctive usage of lorazepam (1 to 2 mg every 4 h) or clozepam (0.5 to 1 mg every 4 h) may be beneficial to control agitation. Antipsychotics are indicated in patients with severe agitation who respond only partially to benzodiazepines.

Valproic acid is an alternative in patients who cannot tolerate lithium or respond poorly to it. Valproic acid may be better than lithium for patients who experience rapid cycling (i.e., more than four episodes a year) or who present with a mixed or dysphoric mania. Tremor and weight gain are the most common side effects; hepatotoxicity and pancreatitis are rare toxicities. Carbamazepine and oxcarbazepine, although not formally approved by the U.S. Food and Drug Administration (FDA) for bipolar disorder, have clinical efficacy in the treatment of acute mania. Preliminary evidence also suggests that other anticonvulsant agents such as levtiracetam, zonisamide and topiramate may possess some therapeutic benefit.

The recurrent nature of bipolar mood disorder necessitates maintenance treatment. Compliance is frequently an issue and often requires enlistment and education of concerned family members. Efforts to identify and modify psychosocial factors that may trigger episodes are important, as is an emphasis on lifestyle regularity. Antidepressant medications are sometimes required for the treatment of severe breakthrough depressions, but their use should generally be avoided during maintenance treatment because of the risk of precipitating mania or accelerating the cycle frequency. Loss of efficacy over time may be observed with any of the mood-stabilizing agents. In such situations, an alternative agent or therapy is usually helpful.

There remains a need to provide an effective treatment for mania and/or for bipolar disorder. Preferably, the treatment of bipolar disorder comprises treatment of the depression and the mania. More preferably, the treatment of bipolar disorder comprises treatment of the depression, the mania and the cycling that are characteristic of the disorder.

SUMMARY OF THE INVENTION

The present invention is directed to a method for the treatment of mania and/or bipolar disorder comprising administering to a subject in need thereof a therapeutically effective amount of a compound of formula (I)

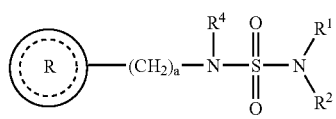

(I)

wherein
$R^1$ and $R^2$ are each independently selected from the group consisting of hydrogen and lower alkyl;
$R^4$ is selected from the group consisting of hydrogen and lower alkyl;
a is an integer from 1 to 2;

is selected from the group consisting of

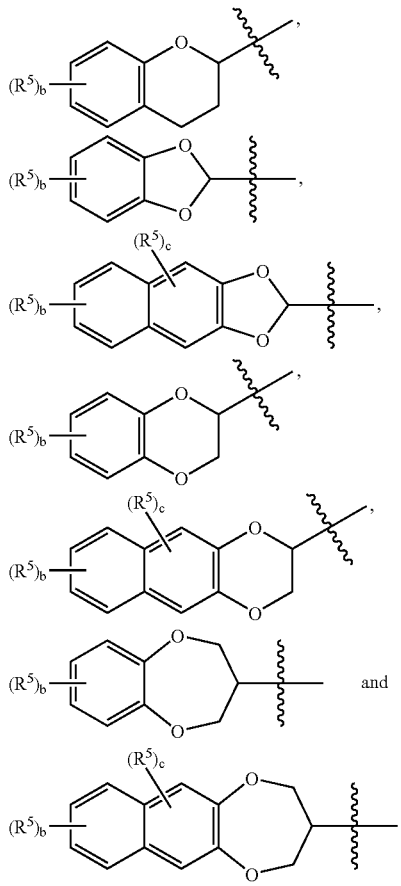

wherein b is an integer from 0 to 4; and wherein c is an integer from 0 to 2;

each $R^5$ is independently selected from the group consisting of halogen, lower alkyl and nitro;
provided that when

is

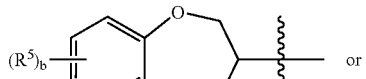 or

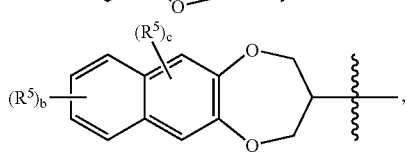, then a is 1;
or a pharmaceutically acceptable salt thereof.

The present invention is further directed to a method for the treatment of mania and/or bipolar disorder comprising administering to a subject in need thereof a therapeutically effective amount of compound of formula (II)

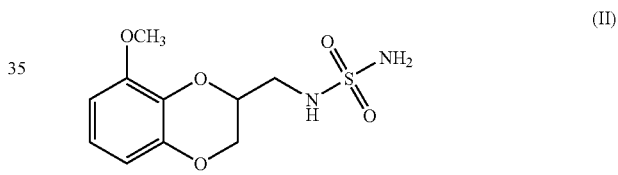

(II)

or a pharmaceutically acceptable salt thereof.

The present invention is further directed to a method for the treatment of mania comprising co-therapy with a therapeutically effective amount of at least one antipsychotic and a compound of formula (I) or formula (II) as described herein. The present invention is further directed to a method for the treatment of bipolar disorder comprising co-therapy with a therapeutically effective amount of at least one antidepressant and/or at least one antipsychotic and a compound of formula (I) or formula (II) as described herein. The present invention is further directed to a method for the treatment of bipolar disorder comprising co-therapy with a therapeutically effective amount of at least one mood stabilizer and a compound of formula (I) or formula (II) as described herein.

Exemplifying the invention is a method of treating mania comprising administering to a subject in need thereof a therapeutically effective amount of any of the compounds described above. Exemplifying the invention is a method of treating bipolar disorder comprising administering to a subject in need thereof a therapeutically effective amount of any of the compounds described above.

In an embodiment, the present invention is directed to the treatment of mania. In another embodiment, the present invention is directed to the treatment of bipolar mania. In another embodiment, the present invention is directed to the treatment of bipolar depression. In another embodiment, the present invention is directed to the treatment of bipolar disorder. In another embodiment, the present invention is directed to the treatment of the bipolar cycling. In another embodiment, the present invention is directed to the treatment of the depression and the mania associated with bipolar disorder. In yet another embodiment, the present invention is directed to the treatment of the depression, the mania and the cycling associated with bipolar disorder. In yet another embodiment, the present invention is directed to a method for treating bipolar disorder comprising stabilization of cycling. Thus, in an embodiment, the present invention is directed to a method of stabilizing bipolar cycling.

DETAILED DESCRIPTION OF THE INVENTION

The present invention is directed to a method for the treatment of mania and/or bipolar disorder comprising administering to a subject in need thereof a therapeutically effective amount of a compound of formula (I)

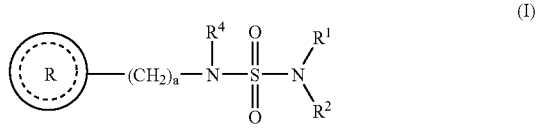

or a pharmaceutically acceptable salt thereof, wherein

a, $R^1$, $R^2$ and $R^4$ are as herein defined. More specifically, the compounds of the present invention are useful for the treatment of the mania, regardless of cause. Further, the compounds of the present invention are useful for the treatment of depression, mania and/or the cycling that are characteristic of, symptomatic of or associated with bipolar disorder.

The present invention is further directed to methods for the treatment of mania, bipolar depression, bipolar mania, bipolar cycling and/or bipolar disorder comprising administering to a subject in need thereof co-therapy with at least one antidepressant and/or at least one antipsychotic agent and/or at least one mood stabilizer and a compound of formula (I) or formula (II) as described herein.

Bipolar disorder is psychiatric disorder characterized by unpredictable swings in mood from mania (or hypomania) to depression. As used herein, the term "bipolar disorder" shall include bipolar disorder I (e.g. single manic episode, most recent episode hypomanic, most recent episode manic, most recent episode mixed, most recent episode depressed and most recent episode unspecified), bipolar disorder II, cyclothymic disorder and bipolar disorder not otherwise specified (as these terms are defined by their diagnostic criteria, in the *Diagnostic and Statistical Manual of Mental Disorders*, $4^{th}$ Edition, Text Revision, American Psychiatric Association, 2000 (DSM-IV-TR)). Preferably, the bipolar disorder is characterized by depressive and manic (or hypomanic) phases, wherein the phases cycle. Preferably, the bipolar disorder is bipolar disorder I or bipolar disorder II.

As used herein, the term "mania" shall include mania or a manic mood phase, regardless of underlying cause. As used herein, the term "bipolar mania" is intended to mean the mania associated with, characteristic of or symptomatic of a bipolar disorder. Thus, methods of treating bipolar mania of the present invention are directed to methods which treat the mania and/or manic phase of bipolar disorders.

As used herein, the term "bipolar depression" is intended to mean the depression associated with, characteristic of or symptomatic of a bipolar disorder. Thus, methods of treating bipolar depression of the present invention are directed to methods which treat the depression and/or depressed phase of bipolar disorders.

As used herein, unless otherwise noted the terms "cycling" or "bipolar cycling" shall refer to the alternation of mood between depressive and manic phases characteristic of bipolar disorders. Thus, the present invention includes methods for the stabilization of said cycling, including, but not limited to, decreasing the frequency of the cycling and/or decreasing the magnitude of the manic and/or depressive phases.

As used herein, the term "mood stabilizer" shall include any pharmaceutical agent which controls mood including, but not limited to, lithium, valproic acid, sodium valproate, carbamazepine, lamotrigine, topiramate, and the like. More specifically, a mood stabilizer is any pharmaceutical agent which stabilizes the patients mood may act as an antidepressant, an antimanic or both and biases the patient mood toward euthymia.

As used herein, unless otherwise noted, the term "antidepressant" shall mean any pharmaceutical agent which treats depression. Suitable examples include, but are not limited to mono-amine oxidase inhibitors such as pheneizine, tranylcypromine, moclobemide, and the like; tricyclics such as imipramine, amitriptyline, desipramine, nortriptyline, doxepin, protriptyline, trimipramine, chlomipramine, amoxapine, and the like; tetracyclics such as maprotiline, and the like; non-cyclics such as nomifensine, and the like; triazolopyridines such as trazodone, and the like; serotonin reuptake inhibitors such as fluoxetine, sertraline, paroxetine, citalopram, fluvoxamine, and the like; serotonin receptor antagonists such as nefazadone, and the like; serotonin noradrenergic reuptake inhibitors such as venlafaxine, milnacipran and the like; noradrenergic and specific serotonergic agents such as mirtazapine, and the like; noradrenaline reuptake inhibitors such as reboxetine, and the like; atypical antidepressants such as bupropion, and the like; natural products such as Kava-Kava, St. John's Wort, and the like; dietary supplements such as s-adenosylmethionine, and the like; and neuropeptides such as thyrotropin-releasing hormone and the like, and the like; compounds targeting neuropeptide receptors such as neurokinin receptor antagonists and the like; and hormones such as triiodothyronine, and the like. Preferably, the antidepressant is selected from the group consisting of fluoxetine, imipramine, bupropion, venlafaxine and sertaline.

As used herein the term "antipsychotic" is intended to includes, but are is not limited to (a) typical or traditional antipsychotics, such as phenothiazines (e.g., chlorpromazine, thioridazine, fluphenazine, perphenazine, trifluoperazine, levomepromazin), thioxanthenes (eg, thiothixene, flupentixol), butyrophenones (e.g., haloperidol), dibenzoxazepines (e.g., loxapine), dihydroindolones (e.g., molindone), substituted benzamides (e.g., sulpride, amisulpride), and the like; and (b) atypical antipsychotics, such as divalproate sodium, paliperidone, clozapine, risperidone, olanzapine, quetiapine, zotepine, ziprasidone, iloperidone, perospirone, blonanserin, sertindole, ORG-5222 (Organon), and the like; and others such as sonepiprazole, aripiprazole, nemonapride, SR-31742 (Sanofi), CX-516 (Cortex), SC-111 (Scotia), NE-100 (Taisho), and the like.

More specifically, atypical antipsychotics include, but are not limited to:

2-methyl-4-(4-methyl-1-piperazinyl)-10H-thieno[2,3-b] benzodiazepine, known as olanzapine and described in U.S. Pat. No. 5,229,382 as useful for the treatment of schizophrenia, schizophreniform disorder, acute mania, mild anxiety states and psychosis; with a recommended dosage of 5-30 mg/day, preferably 5-10 mg/day (Physician's Desk Reference; Kaplan & Sadock's Comprehensive Textbook of Psychiatry, Seventh Edition, Volume II, Lippincott Williams & Wilkins: Philadelphia, 2000);

8-chloro-11-(4-methyl-1-piperazinyl)-5H-dibenzo[b,e][1,4]diazepine, known as clozapine and disclosed in U.S. Pat. No. 3,539,573, with clinical efficacy in the treatment of schizophrenia described in Hanes, et al., Psychopharmacological Bulletin, 24, 62 (1988)); with a recommended dosage of 12.5-600 mg/day, preferably 250-450 mg/day (Physician's Desk Reference; Kaplan & Sadock's Comprehensive Textbook of Psychiatry, Seventh Edition, Volume II, Lippincott Williams & Wilkins: Philadelphia, 2000);

3-[2-[4-(6-fluoro-1,2-benzisoxazol-3-yl)piperidino] ethyl]-2-methyl-6,7,8,9-tetrahydro-4H-pyrido-[1,2-a]pyrimidin-4-one, known as risperidone and described in U.S. Pat. No. 4,804,663 as useful for the treatment of psychotic diseases; with a recommended dosage of 0.25-16 mg/day, preferably 1-16 mg/day, more preferably 2-8 mg/day (Physician's Desk Reference; Kaplan & Sadock's Comprehensive Textbook of Psychiatry, Seventh Edition, Volume II, Lippincott Williams & Wilkins: Philadelphia, 2000);

3-[2-[4-(6-fluoro-1,2-benzisoxazol-3-yl)-1-piperidinyl] ethyl]-6,7,8,9-tetrahydro-9-hydroxy-2-methyl-H-Pyrido[1,2-a]pyrimidin-4-one, known as paliperidone, also known as 9-hydroxy-risperidone, described in U.S. Pat. No. 5,158,952, useful for the treatment of psychotic disorders, with contemplated dosages in the range of 0.01 mg/kg to about 2 mg/kg body weight per day;

1-[2-[3-[5-chloro-1-(4-fluorophenyl)-1H-indol-3-yl]-1-piperidinyl]ethyl]imidazolidin-2-one, known as sertindole and disclosed in U.S. Pat. No. 4,710,500, with U.S. Pat. No. 5,112,838 and U.S. Pat. No. 5,238,945 disclosing the use of sertindole for the treatment of schizophrenia; with a starting dose of 4 mg/day, with increases of 4 mg every other day up to 24 mg/day, with final recommended dosage range of 12 to 20 mg/day (Kaplan & Sadock's Comprehensive Textbook of Psychiatry, Seventh Edition, Volume II, Lippincott Williams & Wilkins: Philadelphia, pp. 2467-2468, 2000);

5-[2-(4-dibenzo[b,f][1,4]thiazepin-11-yl-1-piperazinyl) ethoxy]ethanol, known as quetiapine and disclosed in U.S. Pat. No. 4,879,288 for the treatment of schizophrenia; with a recommended dosage of 25-800 mg/day, preferably 150-750 mg/day (Physician's Desk Reference; Kaplan & Sadock's Comprehensive Textbook of Psychiatry, Seventh Edition, Volume II, Lippincott Williams & Wilkins: Philadelphia, 2000);

5-[2-[4-(1,2-dibenzoisothiazol-3-yl)-1-piperazinyl] ethyl]-6-chloro-1,3-dihydro-2H-indol-2-one, known as ziprasidone and disclosed in U.S. Pat. No. 4,831,031 and U.S. Pat. No. 5,312,925, with its utility in the treatment of schizophrenia disclosed in U.S. Pat. No. 4,831,031; with a recommended dosage of 40-160 mg/day, with a preferred dosage for maintenance treatment and prevention of relapse of 40 to 60 mg twice a day (Kaplan & Sadock's Comprehensive Textbook of Psychiatry, Seventh Edition, Volume II, Lippincott Williams & Wilkins: Philadelphia, pp. 2470-2471, 2000); and sodium hydrogen bis(2-propylpentanoate), also known as divalproex sodium, described in U.S. Pat. No. 5,212,326, with a recommended dosage for the treatment of mania at an initial 750 mg/day with a maximum recommended dosage of 60 mg/kg/day (Physicians Desk Reference).

The term "subject" as used herein, refers to an animal, preferably a mammal, most preferably a human, who has been the object of treatment, observation or experiment.

The term "therapeutically effective amount" as used herein, means that amount of active compound or pharmaceutical agent that elicits the biological or medicinal response in a tissue system, animal or human that is being sought by a researcher, veterinarian, medical doctor or other clinician, which includes alleviation of the symptoms of the disease or disorder being treated.

Wherein the present invention is directed to co-therapy or combination therapy, comprising administration of one or more compound(s) of formula (I) or formula (II) and one or more antipsychotic and/or antidepressant, "therapeutically effective amount" shall mean that amount of the combination of agents taken together so that the combined effect elicits the desired biological or medicinal response. For example, the therapeutically effective amount of co-therapy comprising administration of a compound of formula (I) or formula (II) and at least on antidepressant and/or at least one antipsychotic would be the amount of the compound of formula (I) or formula (II) and the amount of the antidepressant and/or antipsychotic that when taken together or sequentially have a combined effect that is therapeutically effective. Further, it will be recognized by one skilled in the art that in the case of co-therapy with a therapeutically effective amount, as in the example above, the amount of the compound of formula (I) or formula (II) and/or the amount of the antidepressant and/or antipsychotic individually may or may not be therapeutically effective.

As used herein, the terms "co-therapy" and "combination therapy" shall mean treatment of a subject in need thereof by administering one or more compounds of formula (I) or formula (II) in combination with one or more antidepressant(s) and/or antipsychotic(s), wherein the compound(s) of formula (I) or formula (II) and the antidepressant(s) and/or antipsychotic(s) are administered by any suitable means, simultaneously, sequentially, separately or in a single pharmaceutical formulation. Where the compound(s) of formula (I) or formula (II) and the antidepressant(s) and/or antipsychotic(s) are administered in separate dosage forms, the number of dosages administered per day for each compound may be the same or different. The compound(s) of formula (I) or formula (II) and the antidepressant(s) and/or antipsychotic(s) may be administered via the same or different routes of administration. Examples of suitable methods of administration include, but are not limited to, oral, intravenous (iv), intramuscular (im), subcutaneous (sc), transdermal, and rectal. Compounds may also be administered directly to the nervous system including, but not limited to, intracerebral, intraventricular, intracerebroventricular, intrathecal, intracisternal, intraspinal and/or peri-spinal routes of administration by delivery via intracranial or intravertebral needles and/or catheters with or without pump devices. The compound(s) of formula (I) or formula (II) and the antidepressant(s) and/or antipsychotic(s) may be administered according to simultaneous or alternating regimens, at the same or different times during the course of the therapy, concurrently in divided or single forms.

In an embodiment, the present invention is directed to a method for the treatment of depression associated with or characteristic of or symptomatic of bipolar disorder. In another embodiment, the present invention is directed to a method for the treatment of mania associated with or characteristic of or symptomatic of bipolar disorder. In yet another embodiment, the present invention is directed to a method for the treatment of cycling (between depression and mania or the depressive and manic phases) associated with or characteristic of or symptomatic of bipolar disorder.

In an embodiment of the present invention $R^1$ is selected from the group consisting of hydrogen and methyl. In another embodiment of the present invention $R^2$ is selected from the group consisting of hydrogen and methyl. In yet another embodiment of the present invention $R^1$ and $R^2$ are each hydrogen or $R^1$ and $R^2$ are each methyl.

In an embodiment of the present invention —$(CH_2)_a$— is selected from the group consisting of —$CH_2$— and —$CH_2$—$CH_2$—. In another embodiment of the present invention —$(CH_2)_a$— is —$CH_2$—.

In an embodiment of the present $R^4$ is selected from the group consisting of hydrogen and methyl, preferably, $R^4$ is hydrogen.

In an embodiment of the present invention a is 1.

In an embodiment of the present invention b is an integer from 0 to 2. In another embodiment of the present invention c is an integer from 0 to 2. In another embodiment of the present invention b is an integer from 0 to 1. In another embodiment of the present invention c is an integer from 0 to 1. In yet another embodiment of the present invention the sum of b and c is an integer form 0 to 2, preferably an integer form 0 to 1. In yet another embodiment of the present invention b is an integer from 0 to 2 and c is 0.

In an embodiment of the present invention,

is selected from the group consisting of

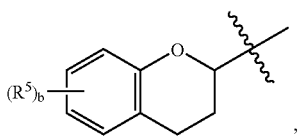,

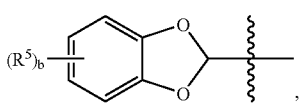,

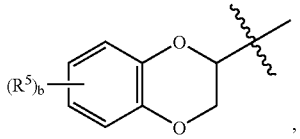,

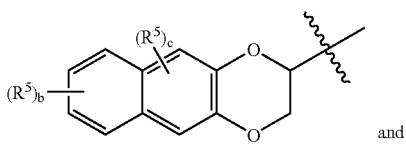 and

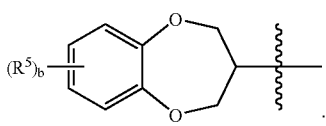.

In another embodiment of the present invention,

is selected from the group consisting of

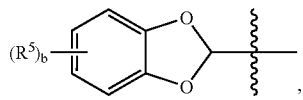,

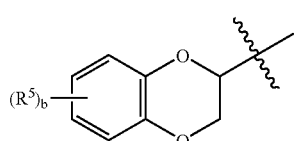 and

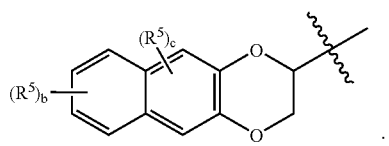.

In an embodiment of the present invention,

is selected from the group consisting of 2-(2,3-dihydro-benzo[1,4]dioxinyl), 2-(benzo[1,3]dioxolyl), 3-(3,4-dihydro-benzo[1,4]dioxepinyl), 2-(6-chloro-2,3-dihydro-benzo[1,4]dioxinyl), 2-(6-fluoro-2,3-dihydro-benzo[1,4]dioxinyl), 2-(chromanyl), 2-(5-fluoro-2,3-dihydro-benzo[1,4]dioxinyl), 2-(7-chloro-2,3-dihydro-benzo[1,4]dioxinyl), 2-(6-chloro-benzo[1,3]dioxolyl), 2-(7-nitro-2,3-dihydro-benzo[1,4]dioxinyl), 2-(7-methyl-2,3-dihydro-benzo[1,4]dioxinyl), 2-(5-chloro-2,3-dihydro-benzo[1,4]dioxinyl), 2-(6-bromo-2,3-dihydro-benzo[1,4]dioxinyl), 2-(6,7-dichloro-2,3-dihydro-benzo[1,4]dioxinyl), 2-(8-chloro-2,3-dihydro-benzo[1,4]dioxinyl), 2-(2,3-dihydro-naphtho[2,3-b][1,4]dioxinyl) and 2-(4-methyl-benzo[1,3]dioxolyl).

In another embodiment of the present invention,

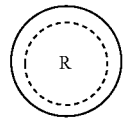

is selected from the group consisting 2-(benzo[1,3]dioxolyl), 2-(2,3-dihydro-benzo[1,4]dioxinyl), 2-(6-chloro-2,3-dihydro-benzo[1,4]dioxinyl), 2-(7-chloro-2,3-dihydro-benzo[1,4]dioxinyl), 2-(7-methyl-2,3-dihydro-benzo[1,4]dioxinyl), 2-(6-bromo-2,3-dihydro-benzo[1,4]dioxinyl) and 2-(6,7-dichloro-2,3-dihydro-benzo[1,4]dioxinyl). In another embodiment of the present invention,

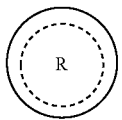

is selected from the group consisting of 2-(2,3-dihydro-benzo[1,4]dioxinyl), 2-(7-methyl-2,3-dihydro-benzo[1,4]dioxinyl) and 2-(6-bromo-2,3-dihydro-benzo[1,4]dioxinyl).

subset of substituents selected from the complete list as defined herein.

Representative compounds of the present invention, are as listed in Tables 1 below. Additional compounds of the present invention are as listed in Table 3. In Tables 1 and 2 below, the column headed "stereo" defines the stereo-configuration at the carbon atom of the heterocycle attached at the starred bond. Where no designation is listed, the compound was prepared as a mixture of stereo-configurations. Where an "R" or "S" designation is listed, the stereo-configuration was based on the enantiomerically enriched starting material.

TABLE 1

Representative Compounds of Formula (I)

| ID No. | R | Stereo | $(CH_2)_a$ | $NR^4$ | $R^1$ | $R^2$ |
|---|---|---|---|---|---|---|
| 1 | 2-(2,3-dihydro-benzo[1,4]dioxinyl) | | $CH_2$ | NH | H | H |
| 2 | 2-(benzo[1,3]dioxolyl) | | $CH_2$ | NH | H | H |
| 3 | 3-(3,4-dihydro-2H-benzo[1,4]dioxepinyl) | | $CH_2$ | NH | H | H |
| 4 | 2-(2,3-dihydro-benzo[1,4]dioxinyl) | S | $CH_2$ | NH | H | H |
| 5 | 2-(2,3-dihydro-benzo[1,4]dioxinyl) | R | $CH_2$ | NH | H | H |
| 6 | 2-(2,3-dihydro-benzo[1,4]dioxinyl) | | $CH_2$ | NH | methyl | methyl |
| 7 | 2-(2,3-dihydro-benzo[1,4]dioxinyl) | | $CH_2$ | $N(CH_3)$ | H | H |
| 8 | 2-(6-chloro-2,3-dihydro-benzo[1,4]dioxinyl) | S | $CH_2$ | NH | H | H |
| 9 | 2-(6-fluoro-2,3-dihydro-benzo[1,4]dioxinyl) | S | $CH_2$ | NH | H | H |
| 10 | 2-(chromanyl) | | $CH_2$ | NH | H | H |
| 13 | 2-(5-fluoro-2,3-dihydro-benzo[1,4]dioxinyl) | S | $CH_2$ | NH | H | H |
| 14 | 2-(7-chloro-2,3-dihydro-benzo[1,4]dioxinyl) | S | $CH_2$ | NH | H | H |
| 15 | 2-(6-chloro-benzo[1,3]dioxolyl) | | $CH_2$ | NH | H | H |
| 16 | 2-(2,3-dihydro-benzo[1,4]dioxinyl) | | $CH_2CH_2$ | NH | H | H |
| 18 | 2-(7-nitro-2,3-dihydro-benzo[1,4]dioxinyl) | S | $CH_2$ | NH | H | H |
| 19 | 2-(7-methyl-2,3-dihydro-benzo[1,4]dioxinyl) | S | $CH_2$ | NH | H | H |
| 20 | 2-(5-chloro-2,3-dihydro-benzo[1,4]dioxinyl) | S | $CH_2$ | NH | H | H |
| 22 | 2-(8-methoxy-2,3-dihydro-benzo[1,4]dioxinyl) | S | $CH_2$ | NH | H | H |
| 24 | 2-(6-bromo-2,3-dihydro-benzo[1,4]dioxinyl) | S | $CH_2$ | NH | H | H |
| 29 | 2-(6,7-dichloro-2,3-dihydro-benzo[1,4]dioxinyl) | S | $CH_2$ | NH | H | H |
| 30 | 2-(8-chloro-2,3-dihydro-benzo[1,4]dioxinyl) | S | $CH_2$ | NH | H | H |
| 33 | 2-(2,3-dihydro-naphtho[2,3-b][1,4]dioxinyl) | S | $CH_2$ | NH | H | H |
| 35 | 2-(4-methyl-benzo[1,3]dioxolyl) | | $CH_2$ | NH | H | H |

In an embodiment of the present invention $R^5$ is selected from the group consisting of halogen and lower alkyl. In another embodiment of the present invention $R^5$ is selected from chloro, fluoro, bromo and methyl.

In an embodiment of the present invention, the stereo-center on the compound of formula (I) is in the S-configuration. In another embodiment of the present invention, the stereo-center on the compound of formula (I) is in the R-configuration.

In an embodiment of the present invention the compound of formula (I) is present as an enantiomerically enriched mixture, wherein the % enantiomeric enrichment (% ee) is greater than about 75%, preferably greater than about 90%, more preferably greater than about 95%, most preferably greater than about 98%.

Additional embodiments of the present invention, include those wherein the substituents selected for one or more of the variables defined herein (i.e. $R^1$, $R^2$, $R^3$, $R^4$, X—Y and A) are independently selected to be any individual substituent or any

TABLE 2

Additional Compounds of the Present Invention

| ID No. | Y | Stereo | X | $NR^{14}$ | $R^{11}$ | $R^{12}$ |
|---|---|---|---|---|---|---|
| 23 | 2-(5-methoxy-2,3-dihydro-benzo[1,4]dioxinyl) | S | $CH_2$ | NH | H | H |
| 26 | 2-(6-methylcarbonyl-2,3-dihydro-benzo[1,4]dioxinyl) | S | $CH_2$ | NH | H | H |
| 32 | 2-(6-methoxycarbonyl-2,3-dihydro-benzo[1,4]dioxinyl) | S | $CH_2$ | NH | H | H |

TABLE 2-continued

Additional Compounds of the Present Invention

[Structure shown: Y ring with attachment point * connected to X—N(R14)—S(=O)(=O)—N(R11)(R12); also shown: Y ring alone]

| ID No. | | Stereo | X | NR14 | R11 | R12 |
|---|---|---|---|---|---|---|
| 34 | 2-(6-hydroxymethyl-2,3-dihydro-benzo[1,4]dioxinyl) | S | CH2 | NH | H | H |
| 36 | 2-(7-amino-2,3-dihydro-benzo[1,4]dioxinyl) | S | CH2 | NH | H | H |

As used herein, unless otherwise noted, "halogen" shall mean chlorine, bromine, fluorine and iodine.

As used herein, unless otherwise noted, the term "alkyl" whether used alone or as part of a substituent group, includes straight and branched chains. For example, alkyl radicals include methyl, ethyl, propyl, isopropyl, butyl, isobutyl, sec-butyl, t-butyl, pentyl and the like. Unless otherwise noted, "lower" when used with alkyl means a carbon chain composition of 1-4 carbon atoms.

As used herein, unless otherwise noted, "alkoxy" shall denote an oxygen ether radical of the above described straight or branched chain alkyl groups. For example, methoxy, ethoxy, n-propoxy, sec-butoxy, t-butoxy, n-hexyloxy and the like.

As used herein, the notation "*" shall denote the presence of a stereogenic center.

When a particular group is "substituted" (e.g., alkyl, aryl, etc.), that group may have one or more substituents, preferably from one to five substituents, more preferably from one to three substituents, most preferably from one to two substituents, independently selected from the list of substituents.

With reference to substituents, the term "independently" means that when more than one of such substituents is possible, such substituents may be the same or different from each other.

Under standard nomenclature used throughout this disclosure, the terminal portion of the designated side chain is described first, followed by the adjacent functionality toward the point of attachment. Thus, for example, a "phenyl-alkyl-amino-carbonyl-alkyl" substituent refers to a group of the formula

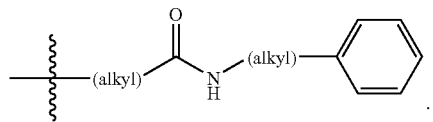

Abbreviations used in the specification, particularly the Schemes and Examples, are as follows:
DCC=Dicyclohexyl Carbodiimide
DCE=Dichloroethane
DCM=Dichloromethane
DIPEA or DIEA=Diisopropylethylamine
DMF=N,N-Dimethylformamide
DMSO=Dimethylsulfoxide
EDC=Ethylcarbodiimide
Et3N or TEA=Triethylamine
Et2O=Diethyl ether
EA or EtOAc=Ethyl acetate
EtOH=Ethanol
IPA=2-propanol
Hept=Heptane
HOBT=1-Hydroxybenzotriazole
HPLC=High Pressure Liquid Chromatography
LAH=Lithium Aluminum Hydride
M or MeOH=Methanol
NMR=Nuclear Magnetic Resonance
Pd—C=Palladium on Carbon Catalyst
RP HPLC=Reverse Phase High Pressure Liquid Chromatography
RT or rt=Room temperature
TEA=Triethylamine
TFA=Trifluoroacetic Acid
THF=Tetrahydrofuran
TLC=Thin Layer Chromatography Where the compounds according to this invention have at least one chiral center, they may accordingly exist as enantiomers. Where the compounds possess two or more chiral centers, they may additionally exist as diastereomers. It is to be understood that all such isomers and mixtures thereof are encompassed within the scope of the present invention. Furthermore, some of the crystalline forms for the compounds may exist as polymorphs and as such are intended to be included in the present invention. In addition, some of the compounds may form solvates with water (i.e., hydrates) or common organic solvents, and such solvates are also intended to be encompassed within the scope of this invention.

For use in medicine, the salts of the compounds of this invention refer to non-toxic "pharmaceutically acceptable salts." Other salts may, however, be useful in the preparation of compounds according to this invention or of their pharmaceutically acceptable salts. Suitable pharmaceutically acceptable salts of the compounds include acid addition salts which may, for example, be formed by mixing a solution of the compound with a solution of a pharmaceutically acceptable acid such as hydrochloric acid, sulfuric acid, fumaric acid, maleic acid, succinic acid, acetic acid, benzoic acid, citric acid, tartaric acid, carbonic acid or phosphoric acid. Furthermore, where the compounds of the invention carry an acidic moiety, suitable pharmaceutically acceptable salts thereof may include alkali metal salts, e.g., sodium or potassium salts; alkaline earth metal salts, e.g., calcium or magnesium salts; and salts formed with suitable organic ligands, e.g., quaternary ammonium salts. Thus, representative pharmaceutically acceptable salts include the following:

acetate, benzenesulfonate, benzoate, bicarbonate, bisulfate, bitartrate, borate, bromide, calcium edetate, camsylate, carbonate, chloride, clavulanate, citrate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroxynaphthoate, iodide, isothionate, lactate, lactobionate, laurate, malate, maleate, mandelate, mesylate, methylbromide, methylnitrate, methylsulfate, mucate, napsylate, nitrate, N-methylglucamine ammonium salt, oleate, pamoate (embonate), palmitate, pantothenate, phosphate/diphosphate, polygalacturonate, salicylate, stearate, sulfate, subacetate, succinate, tannate, tartrate, teoclate, tosylate, triethiodide and valerate.

Representative acids and bases which may be used in the preparation of pharmaceutically acceptable salts include the following:

acids including acetic acid, 2,2-dichloroactic acid, acylated amino acids, adipic acid, alginic acid, ascorbic acid, L-aspartic acid, benzenesulfonic acid, benzoic acid, 4-acetamidobenzoic acid, (+)-camphoric acid, camphorsulfonic acid, (+)-(1S)-camphor-10-sulfonic acid, capric acid, caproic acid, caprylic acid, cinnamic acid, citric acid, cyclamic acid, dodecylsulfuric acid, ethane-1,2-disulfonic acid, ethanesulfonic acid, 2-hydrocy-ethanesulfonic acid, formic acid, fumaric acid, galactaric acid, gentisic acid, glucoheptonic acid, D-gluconic acid, D-glucoronic acid, L-glutamic acid, α-oxo-glutaric acid, glycolic acid, hipuric acid, hydrobromic acid, hydrochloric acid, (+)-L-lactic acid, (±)-DL-lactic acid, lactobionic acid, maleic acid, (−)-L-malic acid, malonic acid, (±)-DL-mandelic acid, methanesulfonic acid, naphthalene-2-sulfonic acid, naphthalene-1,5-disulfonic acid, 1-hydroxy-2-naphthoic acid, nicotinc acid, nitric acid, oleic acid, orotic acid, oxalic acid, palmitric acid, pamoic acid, phosphoric acid, L-pyroglutamic acid, salicylic acid, 4-amino-salicylic acid, sebaic acid, stearic acid, succinic acid, sulfuric acid, tannic acid, (+)-L-tartaric acid, thiocyanic acid, p-toluenesulfonic acid and undecylenic acid; and bases including ammonia, L-arginine, benethamine, benzathine, calcium hydroxide, choline, deanol, diethanolamine, diethylamine, 2-(diethylamino)-ethanol, ethanolamine, ethylenediamine, N-methyl-glucamine, hydrabamine, 1H-imidazole, L-lysine, magnesium hydroxide, 4-(2-hydroxyethyl)-morpholine, piperazine, potassium hydroxide, 1-(2-hydroxyethyl)-pyrrolidine, secondary amine, sodium hydroxide, triethanolamine, tromethamine and zinc hydroxide.

Compounds of formula (I) may be prepared according to the process outlined in Scheme 1.

Compounds of formula (X) wherein is

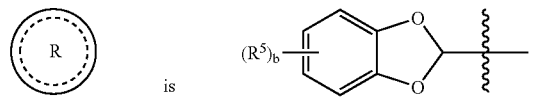

may be prepared according to the process outlined in Scheme 2.

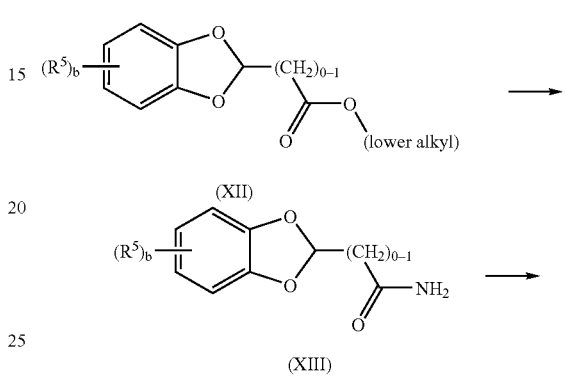

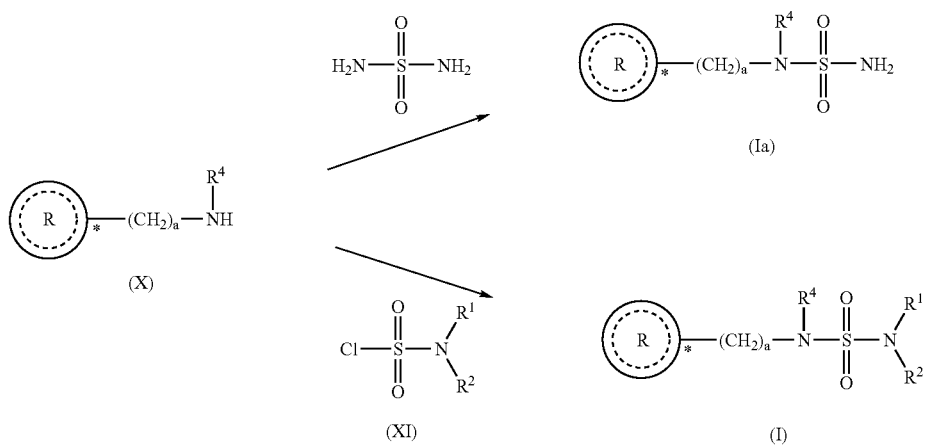

Accordingly, a suitably substituted compound of formula (X), a known compound or compound prepared by known methods, is reacted with sulfamide, a known compound, preferably wherein the sulfamide is present in an amount in the range of about 2 to about 5 equivalents, in an organic solvent such as THF, dioxane, and the like, preferably at an elevated temperature in the range of about 50° C. to about 100° C., more preferably at about reflux temperature, to yield the corresponding compound of formula (Ia).

Alternatively, a suitably substituted compound of formula (X), a known compound or compound prepared by known methods, is reacted with a suitably substituted compound of formula (XI), a known compound or compound prepared by known methods, in the presence of a base such as TEA, DIPEA, pyridine, and the like, in an organic solvent such as DMF, DMSO, and the like, to yield the corresponding compound of formula (I).

-continued

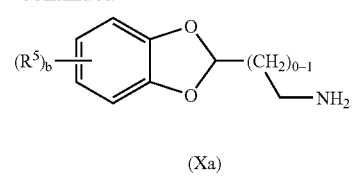

Accordingly, a suitably substituted compound of formula (XII), a known compound or compound prepared by known method (for example as described in Scheme 3 above) is reacted with $NH_4OH$, a known compound, optionally in an organic solvent such as acetonitrile, and the like, to yield the corresponding compound of formula (XIII).

The compound of formula (XIII) is reacted with a suitably selected reducing agent, such as LAH, and the like, and the like, in an organic solvent such as THF, diethyl ether, and the like, to yield the corresponding compound of formula (Xa).

Compounds of formula (X) wherein

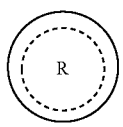

is selected from

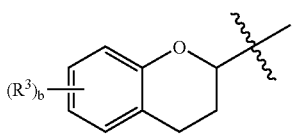

may be prepared according to the process outlined in Scheme 3.

Scheme 3

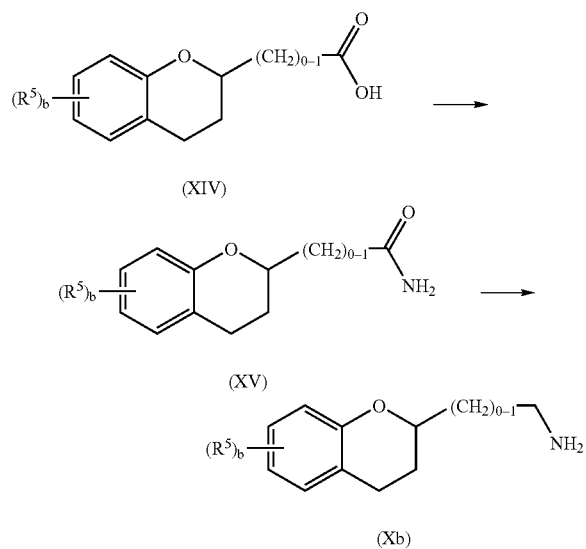

Accordingly, a suitably substituted compound of formula (XIV), a known compound or compound prepared by known methods, is reacted with NH$_4$OH, in the presence of a coupling agent such as DCC, and the like, optionally in an organic solvent such as acetonitrile, and the like, to yield the corresponding compound of formula (XV).

The compound of formula (XV) is reacted with a suitably selected reducing agent, such as LAH, and the like, in an organic solvent such as THF, diethyl ether, and the like, to yield the corresponding compound of formula (Xb).

Compounds of formula (X) wherein

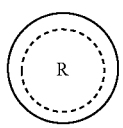

is selected from

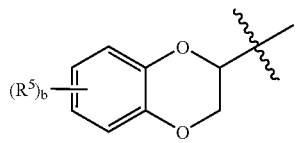

and wherein a is 2, may be prepared according to the process outlined in Scheme 4.

Scheme 5

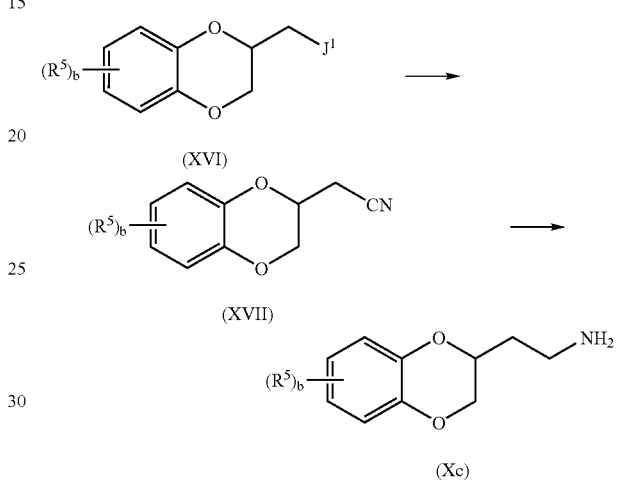

Accordingly, a suitably substituted compound of formula (XVI) wherein J$^1$ is a suitable leaving group such as Br, Cl, I, tosyl, mesyl, triflyl, and the like, a known compound or compound prepared by known methods (for example, by activating the corresponding compound wherein J$^1$ is OH), is reacted with a cyanide such as potassium cyanide, sodium cyanide, and the like, in an organic solvent such as DMSO, DMF, THF, and the like, to yield the corresponding compound of formula (XVII).

The compound of formula (XVII) is reduced according to known methods, for example by reacting with a suitable reducing agent such as LAH, borane, and the like, to yield the corresponding compound of formula (Xc).

Compounds of formula (X) wherein

is selected from

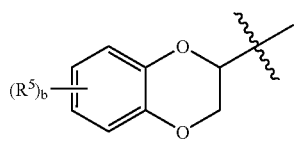

and wherein a is 1, may be prepared according to the process outlined in Scheme 5.

Scheme 5

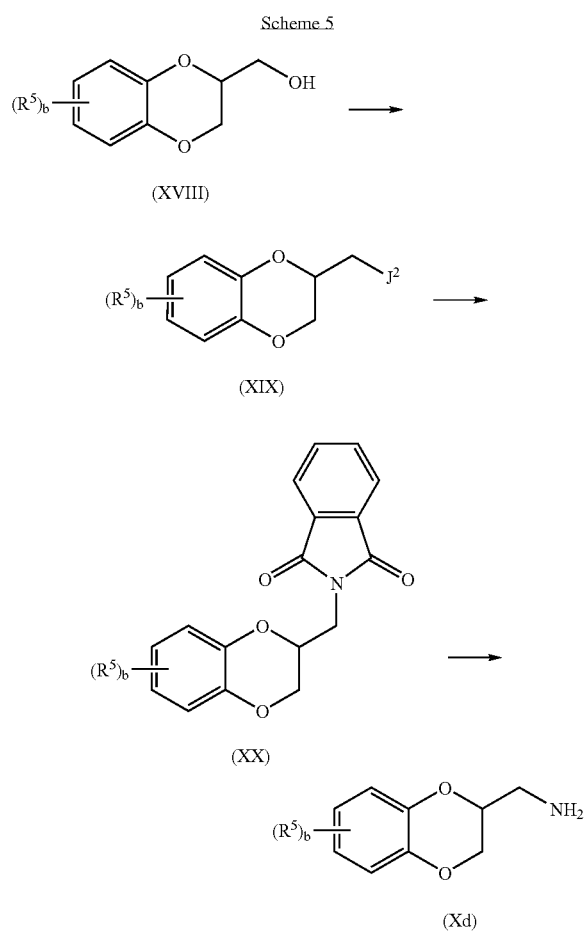

Accordingly, a suitably substituted compound of formula (XVIII), a known compound or compound prepared by known methods is activated, according to known method, to yield the corresponding compound of formula (XIX), wherein $J^2$ is a suitable leaving group, such tosylate, Cl, Br, I, mesylate, triflate, and the like.

The compound of formula (XIX) is reacted with a phthalimide salt such as potassium phthlimide, sodium phthalimide, and the like, in an organic solvent such as DMF, DMSO, acetonitrile, and the like, preferably, at an elevated temperature in the range of from 50° C. to about 200° C., more preferably, at about reflux temperature, to yield the corresponding compound of formula (XX).

The compound of formula (XX) is reacted with $N_2H_4$, a known compound, in an organic solvent such as ethanol, methanol, and the like, preferably, at an elevated temperature in the range of from about 50° C. to about 100° C., more preferably, at about reflux temperature, and the like, to yield the corresponding compound of formula (Xd).

One skilled in the art will recognize that compounds of formula (X) wherein

is selected from

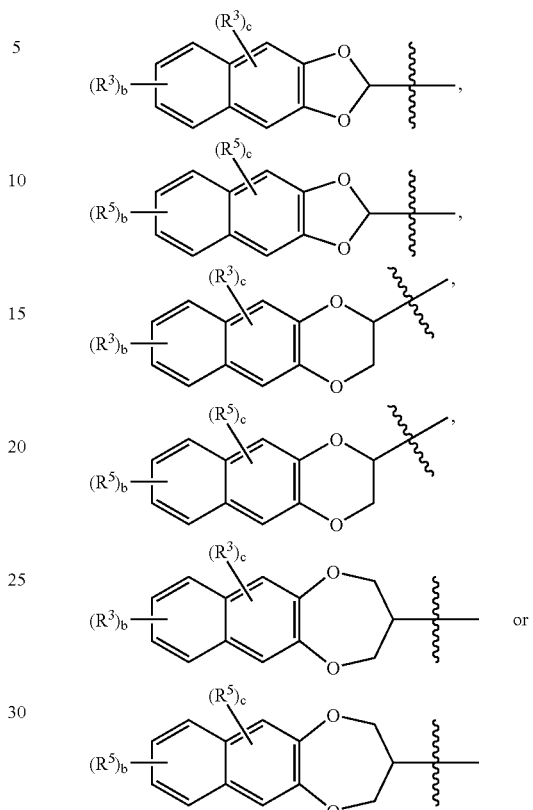

may be similarly prepared according to known methods or for example, according to the processes outlined in Schemes 2 through 5 above, by selecting and substituting the corresponding naphthyl-fused compounds for the benzo-fused starting materials.

One skilled in the art will further recognize that wherein a single enantiomer (or a mixture of enantiomers wherein one enantiomer is enriched) of a compound of formula (X) is desired, the above processes as described in Schemes 1 through 5 may be applied by substituting the corresponding single enantiomer (or mixture of enantiomers wherein one enantiomer is enriched) for the appropriate starting material.

One skilled in the art will recognize that wherein a reaction step of the present invention may be carried out in a variety of solvents or solvent systems, said reaction step may also be carried out in a mixture of the suitable solvents or solvent systems.

Where the processes for the preparation of the compounds according to the invention give rise to mixture of stereoisomers, these isomers may be separated by conventional techniques such as preparative chromatography. The compounds may be prepared in racemic form, or individual enantiomers may be prepared either by enantiospecific synthesis or by resolution. The compounds may, for example, be resolved into their component enantiomers by standard techniques, such as the formation of diastereomeric pairs by salt formation with an optically active acid, such as (−)-di-p-toluoyl-D-tartaric acid and/or (+)-di-p-toluoyl-L-tartaric acid followed by fractional crystallization and regeneration of the free base. The compounds may also be resolved by formation of diastereomeric esters or amides, followed by chromatographic separation and removal of the chiral auxiliary. Alternatively, the compounds may be resolved using a chiral HPLC column.

During any of the processes for preparation of the compounds of the present invention, it may be necessary and/or desirable to protect sensitive or reactive groups on any of the molecules concerned. This may be achieved by means of conventional protecting groups, such as those described in *Protective Groups in Organic Chemistry*, ed. J. F. W. McOmie, Plenum Press, 1973; and T. W. Greene & P. G. M. Wuts, *Protective Groups in Organic Synthesis*, John Wiley & Sons, 1991. The protecting groups may be removed at a convenient subsequent stage using methods known from the art.

The present invention further comprises pharmaceutical compositions containing one or more compounds of formula (I) with a pharmaceutically acceptable carrier. Pharmaceutical compositions containing one or more of the compounds of the invention described herein as the active ingredient can be prepared by intimately mixing the compound or compounds with a pharmaceutical carrier according to conventional pharmaceutical compounding techniques. The carrier may take a wide variety of forms depending upon the desired route of administration (e.g., oral, parenteral). Thus for liquid oral preparations such as suspensions, elixirs and solutions, suitable carriers and additives include water, glycols, oils, alcohols, flavoring agents, preservatives, stabilizers, coloring agents and the like; for solid oral preparations, such as powders, capsules and tablets, suitable carriers and additives include starches, sugars, diluents, granulating agents, lubricants, binders, disintegrating agents and the like. Solid oral preparations may also be coated with substances such as sugars or be enteric-coated so as to modulate major site of absorption. For parenteral administration, the carrier will usually consist of sterile water and other ingredients may be added to increase solubility or preservation. Injectable suspensions or solutions may also be prepared utilizing aqueous carriers along with appropriate additives.

To prepare the pharmaceutical compositions of this invention, one or more compounds of the present invention as the active ingredient is intimately admixed with a pharmaceutical carrier according to conventional pharmaceutical compounding techniques, which carrier may take a wide variety of forms depending of the form of preparation desired for administration, e.g., oral or parenteral such as intramuscular. In preparing the compositions in oral dosage form, any of the usual pharmaceutical media may be employed. Thus, for liquid oral preparations, such as for example, suspensions, elixirs and solutions, suitable carriers and additives include water, glycols, oils, alcohols, flavoring agents, preservatives, coloring agents and the like; for solid oral preparations such as, for example, powders, capsules, caplets, gelcaps and tablets, suitable carriers and additives include starches, sugars, diluents, granulating agents, lubricants, binders, disintegrating agents and the like. Because of their ease in administration, tablets and capsules represent the most advantageous oral dosage unit form, in which case solid pharmaceutical carriers are obviously employed. If desired, tablets may be sugar coated or enteric coated by standard techniques. For parenterals, the carrier will usually comprise sterile water, through other ingredients, for example, for purposes such as aiding solubility or for preservation, may be included. Injectable suspensions may also be prepared, in which case appropriate liquid carriers, suspending agents and the like may be employed. The pharmaceutical compositions herein will contain, per dosage unit, e.g., tablet, capsule, powder, injection, teaspoonful and the like, an amount of the active ingredient necessary to deliver an effective dose as described above. The pharmaceutical compositions herein will contain, per unit dosage unit, e.g., tablet, capsule, powder, injection, suppository, teaspoonful and the like, of from about 0.1-1000 mg and may be given at a dosage of from about 0.01-200.0 mg/kg/day, preferably from about 0.1 to 100 mg/kg/day, more preferably from about 0.5-50 mg/kg/day, more preferably from about 1.0-25.0 mg/kg/day or any range therein. The dosages, however, may be varied depending upon the requirement of the patients, the severity of the condition being treated and the compound being employed. The use of either daily administration or post-periodic dosing may be employed.

Preferably these compositions are in unit dosage forms from such as tablets, pills, capsules, powders, granules, sterile parenteral solutions or suspensions, metered aerosol or liquid sprays, drops, ampoules, autoinjector devices or suppositories; for oral parenteral, intranasal, sublingual or rectal administration, or for administration by inhalation or insufflation. Alternatively, the composition may be presented in a form suitable for once-weekly or once-monthly administration; for example, an insoluble salt of the active compound, such as the decanoate salt, may be adapted to provide a depot preparation for intramuscular injection. For preparing solid compositions such as tablets, the principal active ingredient is mixed with a pharmaceutical carrier, e.g. conventional tableting ingredients such as corn starch, lactose, sucrose, sorbitol, talc, stearic acid, magnesium stearate, dicalcium phosphate or gums, and other pharmaceutical diluents, e.g. water, to form a solid preformulation composition containing a homogeneous mixture of a compound of the present invention, or a pharmaceutically acceptable salt thereof. When referring to these preformulation compositions as homogeneous, it is meant that the active ingredient is dispersed evenly throughout the composition so that the composition may be readily subdivided into equally effective dosage forms such as tablets, pills and capsules. This solid preformulation composition is then subdivided into unit dosage forms of the type described above containing from 0.1 to about 1000 mg of the active ingredient of the present invention. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of material can be used for such enteric layers or coatings, such materials including a number of polymeric acids with such materials as shellac, cetyl alcohol and cellulose acetate.

The liquid forms in which the novel compositions of the present invention may be incorporated for administration orally or by injection include, aqueous solutions, suitably flavored syrups, aqueous or oil suspensions, and flavored emulsions with edible oils such as cottonseed oil, sesame oil, coconut oil or peanut oil, as well as elixirs and similar pharmaceutical vehicles. Suitable dispersing or suspending agents for aqueous suspensions, include synthetic and natural gums such as tragacanth, acacia, alginate, dextran, sodium carboxymethylcellulose, methylcellulose, polyvinyl-pyrrolidone or gelatin.

The method of treating depression described in the present invention may also be carried out using a pharmaceutical composition comprising any of the compounds as defined herein and a pharmaceutically acceptable carrier. The pharmaceutical composition may contain between about 0.1 mg and 1000 mg, preferably about 50 to 500 mg, of the compound, and may be constituted into any form suitable for the mode of administration selected. Carriers include necessary and inert pharmaceutical excipients, including, but not limited to, binders, suspending agents, lubricants, flavorants, sweeteners, preservatives, dyes, and coatings. Compositions suitable for oral administration include solid forms, such as pills, tablets, caplets, capsules (each including immediate release, timed release and sustained release formulations), granules, and powders, and liquid forms, such as solutions, syrups, elixers, emulsions, and suspensions. Forms useful for parenteral administration include sterile solutions, emulsions and suspensions.

Advantageously, compounds of the present invention may be administered in a single daily dose, or the total daily dosage may be administered in divided doses of two, three or four times daily. Furthermore, compounds for the present invention can be administered in intranasal form via topical use of suitable intranasal vehicles, or via transdermal skin patches well known to those of ordinary skill in that art. To be administered in the form of a transdermal delivery system, the dosage administration will, of course, be continuous rather than intermittent throughout the dosage regimen.

For instance, for oral administration in the form of a tablet or capsule, the active drug component can be combined with an oral, non-toxic pharmaceutically acceptable inert carrier such as ethanol, glycerol, water and the like. Moreover, when desired or necessary, suitable binders; lubricants, disintegrating agents and coloring agents can also be incorporated into the mixture. Suitable binders include, without limitation, starch, gelatin, natural sugars such as glucose or beta-lactose, corn sweeteners, natural and synthetic gums such as acacia, tragacanth or sodium oleate, sodium stearate, magnesium stearate, sodium benzoate, sodium acetate, sodium chloride and the like. Disintegrators include, without limitation, starch, methyl cellulose, agar, bentonite, xanthan gum and the like.

The liquid forms in suitably flavored suspending or dispersing agents such as the synthetic and natural gums, for example, tragacanth, acacia, methyl-cellulose and the like. For parenteral administration, sterile suspensions and solutions are desired. Isotonic preparations which generally contain suitable preservatives are employed when intravenous administration is desired.

Compounds of this invention may be administered in any of the foregoing compositions and according to dosage regimens established in the art whenever treatment of depression is required.

The daily dosage of the products may be varied over a wide range from 0.01 to 200 mg/kg per adult human per day. For oral administration, the compositions are preferably provided in the form of tablets containing, 0.01, 0.05, 0.1, 0.5, 1.0, 2.5, 5.0, 10.0, 15.0, 25.0, 50.0, 100, 150, 200, 250, 500 and 1000 milligrams of the active ingredient for the symptomatic adjustment of the dosage to the patient to be treated. An effective amount of the drug is ordinarily supplied at a dosage level of from about 0.01 mg/kg to about 200 mg/kg of body weight per day. Preferably, the range is from about 0.1 to about 100.0 mg/kg of body weight per day, more preferably, from about 0.5 mg/kg to about 50 mg/kg, more preferably, from about 1.0 to about 25.0 mg/kg of body weight per day. The compounds may be administered on a regimen of 1 to 4 times per day.

Optimal dosages to be administered may be readily determined by those skilled in the art, and will vary with the particular compound used, the mode of administration, the strength of the preparation, the mode of administration, and the advancement of the disease condition. In addition, factors associated with the particular patient being treated, including patient age, weight, diet and time of administration, will result in the need to adjust dosages.

One skilled in the art will recognize that, both in vivo and in vitro trials using suitable, known and generally accepted cell and/or animal models are predictive of the ability of a test compound to treat or prevent a given disorder.

One skilled in the art will further recognize that human clinical trails including first-in-human, dose ranging and efficacy trials, in healthy patients and/or those suffering from a given disorder, may be completed according to methods well known in the clinical and medical arts.

The following Examples are set forth to aid in the understanding of the invention, and are not intended and should not be construed to limit in any way the invention set forth in the claims which follow thereafter.

Example 1

((3,4-Dihydro-2H-benzo[b][1,4]dioxepin-3-yl)methyl)sulfamide (Compound #3)

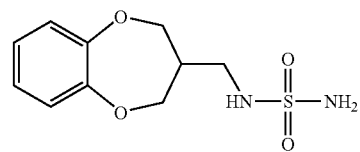

Catechol (5.09 g, 46.2 mmol) and potassium carbonate were combined in acetonitrile and heated to reflux for one hour. 2-Chloromethyl-3-chloro-1-propene (5.78 g, 46.2 mmol) was added and the reaction was continued at reflux for 24 hours. The solution was cooled to room temperature and filtered. The filtrate was evaporated and the residue was diluted with water and extracted with diethyl ether (3×). The combined organic solution was dried over $MgSO_4$ and concentrated. Chromatography (2% ethyl ether in hexane) yielded 3-methylene-3,4-dihydro-2H-benzo[b][1,4]dioxepine as a colorless oil.

MS (ESI): 163.2 (M+H$^+$)

$^1$H NMR (300 MHz, CDCl$_3$), δ: 6.94 (m, 4H), 5.07 (s, 2H), 4.76 (s, 4H).

3-Methylene-3,4-dihydro-2H-benzo[b][1,4]dioxepine (5.00 g, 30.8 mmol) was dissolved in dry THF (100 mL). Borane-THF (1.0 M in THF, 10.3 mL) was added at 0° C. The reaction was stirred at RT for 5 hours. Aminosulfonic acid (6.97 g, 61.6 mmol) was added. The reaction was heated to reflux overnight. The reaction was cooled to room temperature and aqueous sodium hydroxide (3.0 M, 100 mL) was added. The solution was extracted with ethyl acetate (3×100 mL). The combined organic solution was dried over $MgSO_4$. The solution was concentrated under vacuum and purified by chromatography (2% to 8% methanol in dichloromethane) to yield ((3,4-dihydro-2H-benzo[b][1,4]dioxepin-3-yl)methyl)amine as a colorless oil.

MS (ESI): 180.1 (M+H$^+$)

$^1$H NMR (300 MHz, DMSO), δ: 6.92 (m, 4H), 4.21 (m, 2H), 4.07 (m, 2H), 3.33 (broad, 2H), 3.16 (d, J=4 Hz, 1H), 2.72 (d, J=4 Hz, 1H), 2.30 (m, 1H).

((3,4-Dihydro-2H-benzo[b][1,4]dioxepin-3-yl)methyl)amine (2.90 g, 16.2 mmol) and sulfamide (3.11 g, 32.4 mmol) were combined in dry dioxane (60 ml) and heated to reflux overnight. Chloroform was added and the precipitate was removed by filtration. The filtrate was concentrated under vacuum and purified by chromatography (2% to 8% acetone in dichloromethane) to yield the title compound as an off-white solid.

258.8 (M+H⁺)

¹H NMR (300 MHz, DMSO), δ: 6.92 (m, 4H), 6.71 (broad, 1H), 6.59 (broad, 2H), 4.19 (m, 2H), 4.04 (m, 2H), 3.00 (m, 2H), 2.39 (m, 1H).

Example 2

N-(2,3-Dihydro-benzo[1,4]dioxin-2-ylmethyl)-sulfamide (Compound #1)

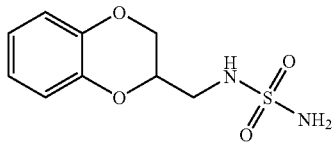

Racemic 2,3-dihydro-1,4-benzdioxin-2-ylmethylamine (4.4 g, 26 mmol) and sulfamide (5.1 g, 53 mmol) were combined in 1,4 dioxane (100 mL) and refluxed for 2 h. The reaction was cooled to room temperature and a small amount of solid was filtered and discarded. The filtrate was evaporated in vacuo and the residue was purified using flash column chromatography (DCM:Methanol—10:1) to yield a white solid. The solid was recrystallized from DCM to yield the title compound as a white solid.

mp: 97.5-98.5° C.

Elemental Analysis:

Anal Calc: C, 44.25; H, 4.95; N, 11.47; S, 13.13

Anal Found: C, 44.28; H, 4.66; N, 11.21; S, 13.15

H¹ NMR (DMSO d6) δ 6.85 (m, 4H), 6.68 (bd s, 3H, NH), 4.28 (m, 2H), 3.97 (dd, J=6.9, 11.4 Hz, 1H), 3.20 (m, 1H), 3.10 (m, 1H).

Example 3

(Benzo[1,3]dioxol-2-ylmethyl)sulfamide (Compound #2)

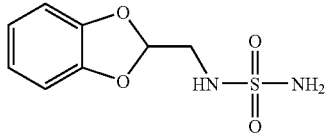

Catechol (10.26 g, 93.2 mmol), sodium methoxide (25% by weight in methanol, 40.3 g, 186 mmol), and methyl dichloroacetate (13.3 g, 93.2 mmol) were combined in dry methanol (100 mL). The solution was heated to reflux overnight. The reaction was cooled to room temperature, acidified by addition of concentrated hydrochloric acid and then reduced in volume under vacuum to about 50 mL. Water was added and the mixture was extracted with diethyl ether (3×100 mL). The combined organic solution was dried with MgSO₄, concentrated to a brown solid, and chromatographed (2% ethyl acetate in hexane) to yield benzo[1,3]dioxole-2-carboxylic acid methyl ester as a colorless oil.

MS (ESI): 195.10 (M+H⁺).

¹H NMR (300 MHz, CDCl₃), δ: 6.89 (broad, 4H), 6.29 (s, 1H), 4.34 (q, J=7 Hz, 2H), 1.33 (t, J=7 Hz, 3H).

To benzo[1,3]dioxole-2-carboxylic acid methyl ester (7.21 g, 40.0 mmol) was added ammonium hydroxide (29% in water, 10 mL) and enough acetonitrile to make the mixture homogeneous (~5 mL). The solution was stirred for two hours at room temperature and then distilled water was added. Benzo[1,3]dioxole-2-carboxylic acid amide precipitated as a white solid and was collected by filtration and used without further purification.

MS (ESI): 160.00 (M+H⁺)

¹H NMR (300 MHz, DMSO), δ: 7.99 (s, broad, 1H), 7.72 (s, broad, 1H), 6.94 (m, 2H) 6.86 (m, 2H), 6.30 (s, 1H).

Benzo[1,3]dioxole-2-carboxylic acid amide (5.44 g, 32.9 mmol) was dissolved in tetrahydrofuran (THF, 100 mL). Lithium aluminum hydride (LAH, 1M in THF, 39.5 mL, 39.5 mmol) was added slowly to the solution at room temperature. The reaction was stirred at room temperature for 24 hours. Distilled water was added to destroy the excess LAH. Aqueous sodium hydroxide (3.0 M, 100 mL) was added and the solution was extracted with ethyl acetate (3×100 mL). The combined organic solution was washed with water and dried over MgSO₄. The solvent was evaporated to yield C-benzo[1,3]dioxol-2-yl-methylamine as a colorless oil.

MS (ESI): 152.1 (M+H⁺)

¹H NMR (300 MHz, CDCl₃), δ: 6.87 (m, 4H), 6.09 (t, J=4 Hz, 1H), 3.13 (d, J=4 Hz, 2H)

C-Benzo[1,3]dioxol-2-yl-methylamine (2.94 g, 19.4 mmol) and sulfamide (3.74 g, 38.9 mmol) were combined in dry dioxane (50 mL) and the solution was heated to reflux overnight. The reaction was concentrated and the residue was chromatographed (2% to 10% acetone in dichloromethane) to yield the title compound as a white solid.

MS (ESI): 230.0 (M+H⁺)

¹H NMR (300 MHz, CDCl₃), δ: 6.87 (m, 4H), 6.25 (t, J=4 Hz, 1H), 4.79 (broad, 1H), 4.62 (broad, 1H), 3.64 (d, J=4 Hz, 2H).

Example 4

(2S)-(−)-N-(2,3-Dihydro-benzo[1,4]dioxin-2-ylmethyl)-sulfamide (Compound #4)

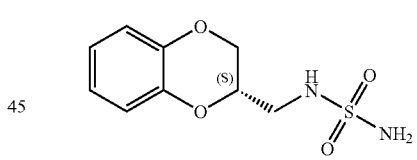

Catechol (13.2 g, 0.12 mol) and potassium carbonate (16.6 g, 0.12 mol) were stirred in DMF (250 mL) and (2R)-glycidyl tosylate (22.8 g, 0.10 mol) was added and the reaction was stirred at 60° C. for 24 h. The reaction was cooled to room temperature and diluted with ice water (1 L) and extracted with diethyl ether (4 times). The combined organic solution was washed 3 times with 10% potassium carbonate, once with water, once with brine and evaporated in vacuo to yield a white solid which was purified by flash column chromatography (DCM:Methanol—50:1) to yield ((2S)-2,3-dihydro-benzo[1,4]dioxin-2-yl)-methanol as a solid.

The solid (13.3 g, 68 mmol) was dissolved in pyridine (85 mL) cooled to 0° C., p-toluenesulfonyl chloride (13.0 g, 68 mmol) was added and the reaction mixture stirred at room temperature for 20 h. The reaction was diluted with diethyl ether (1 L) and 1N HCl (1.2 L). The organic layer was separated and washed 2 times with 1N HCl (500 mL), 4 times with water (150 mL), once with brine, dried (MgSO₄) and evaporated in vacuo to yield a white solid which was purified by flash column chromatography (Hept:EA—2:1) to yield toluene-4-sulfonic acid (2S)-2,3-dihydro-benzo[1,4]dioxin-2-ylmethyl ester as a white solid.

The white solid was combined with potassium phthalimide (14.4 g, 78 mmol) in DMF (250 mL) and heated to reflux for 1 h, cooled to room temperature and poured into vigorously stirring water (1.5 L) and stirred 30 min. White solid was filtered and the solid was washed several times with water, 2% NaOH, and water again and let air dry to yield a (2S)-2-(2,3-Dihydro-benzo[1,4]dioxin-2-ylmethyl)-isoindole-1,3-dione as white powdery solid.

The powdery white solid was combined with hydrazine (2.75 g, 86 mmol) in EtOH (225 mL) and heated at reflux for 2 h, cooled to room temperature and 1N HCl added to pH 1.0 and stirred for 15 min. White solid was filtered and washed with fresh EtOH (solid discarded) and the filtrate was evaporated in vacuo to a solid, which was partitioned between diethyl ether and dilute aqueous NaOH. The diethyl ether solution was dried ($Na_2SO_4$) and evaporated in vacuo to a yield a light yellow oil. The oil was purified by flash column chromatography (DCM:MeOH—10:1) to yield an oil. A portion of the oil (4.82 g, 29 mmol) in 2-propanol (250 mL) was treated with 1N HCl (30 mL) and heated on steambath until homogeneous and then let cool to room temperature. After 3 h, the mixture was ice cooled for 2 h. A white flaky solid (the corresponding HCl salt of (2S)—C-(2,3-Dihydro-benzo[1,4]dioxin-2-yl)-methylamine) was filtered off and then recrystallized again from 2-propanol to yield a white solid.

$[\alpha]_D=-69.6$ (c=1.06, EtOH)

The white solid was partitioned between DCM and dilute NaOH, and the DCM was dried ($NaSO_4$) and evaporated in vacuo to yield (2S)—C-(2,3-Dihydro-benzo[1,4]dioxin-2-yl)-methylamine as an oil.

$[\alpha]_D=-57.8$ (c=1.40, $CHCl_3$)

The oil (2.1 g, 12.7 mmol) and sulfamide (2.44 g, 25.4 mmol) were refluxed in dioxane (75 mL) for 2 h and the crude product was purified by flash column chromatography (DCM:MeOH 10:1) to yield a white solid, which was recrystallized from DCM to yield the title compound as a white crystalline solid.

mp 102-103° C.

$[\alpha]_D=-45.1°$ (c=1.05, M);

$^1$H NMR (DMSO d6) δ 6.86 (m, 4H), 6.81 (bd s, 3H, NH), 4.3 (m, 2H), 3.97 (dd, J=6.9, 11.4 Hz, 1H), 3.20 (dd, J=5.5, 13.7 Hz, 1H), 3.10 (dd, J=6.9, 13.7 Hz, 1H)

Elemental Analysis:

Anal Calc: C, 44.25; H, 4.95; N, 11.47; S, 13.13

Anal Found: C, 44.20; H, 4.69; N, 11.40; S, 13.22.

Example 5

N-(2,3-Dihydro-benzo[1,4]dioxin-2-ylmethyl)-N',N' dimethylsulfamide (Compound #6)

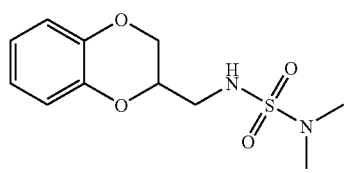

Racemic 2,3-dihydro-1,4-benzdioxin-2-ylmethylamine (8.25 g, 5.0 mmol) and triethylamine (1.52 g, 15 mmol) were combined in DMF (10 mL) and cooled in an ice bath as dimethylsulfamoyl chloride (1.44 g, 10 mmol) was added. The reaction mixture was then stirred for 3 hr with continued cooling. The reaction mixture was partitioned between ethyl acetate and water, and the ethyl acetate solution was washed with brine, dried ($MgSO_4$) and evaporated in vacuo to yield an oil. The oil was purified using flash column chromatography (ethyl acetate:Heptane—1:1) to yield a white solid, which was recrystallized (ethyl acetate/Hexane) to yield the title compound as a white floccular solid.

mp 76-78° C.

MS 273 ($MH^+$)

Elemental Analysis:

Anal Calc: C, 48.52; H, 5.92; N, 10.29; S, 11.78

Anal Found: C, 48.63; H, 5.62; N, 10.20; S, 11.90

$^1$H NMR ($CDCl_3$) δ 6.87 (m, 4H), 4.59 (bd m, 1H, NH), 4.35 (m, 1H), 4.27 (dd, J=2.3, 11.4 Hz, 1H), 4.04 (dd, J=7.0, 11.4, 1H), 3.36 (m, 2H), 2.82 (s, 6H).

Example 6

N-(2,3-Dihydro-benzo[1,4]dioxin-2-ylmethyl)-N-methylsulfamide (Compound #7)

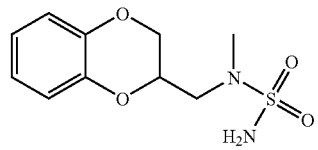

Racemic 2,3-dihydro-1,4-benzdioxin-2-ylmethylamine (825 mg, 5 mmol) was dissolved in ethyl formate (15 mL), refluxed for 30 min and evaporated in vacuo to yield N-(2,3-dihydro-benzo[1,4]dioxin-2-ylmethyl)-formamide as an oil.

The oil in diethyl ether (25 mL) was treated with 1M LAH in THF (9.0 mL, 9.0 mmol) at 0° C. and stirred for 5 h at room temperature. The reaction was cooled in an ice bath and quenched with water (0.50 mL), followed by 3 N NaOH (0.50 mL) and water (0.50 mL). The mixture was then stirred at room temperature for 1 h. Solid was filtered and the filtrate was evaporated in vacuo to yield a residue which was partitioned between 1N HCl and diethyl ether. The aqueous phase was basified with 1N NaOH and extracted with diethyl ether. The organic phase was dried ($MgSO_4$) and evaporated in vacuo to yield (2,3-dihydro-benzo[1,4]dioxin-2-ylmethyl)-methyl-amine as an oil.

MS 180 ($MH^+$)

$^1$H NMR ($CDCl_3$) δ 6.85 (m, 4H), 4.30 (m, 2H), 4.02 (dd, J=7.9, 11.6 Hz, 1H), 2.85 (m, 2H), 2.50 (s, 3H)

The oil (380 mg, 2.1 mmol) and sulfamide (820 mg, 8.5 mmol) were combined in dioxane (15 mL), refluxed for 1.5 h and evaporated in vacuo to yield a crude residue. The residue was purified via column chromatography (ethyl acetate/Heptane 1:1) and the resultant solid was recrystallized from ethyl acetate/Hexane to yield the title compound as a white solid.

mp 97-98° C.

MS 257 ($M^{-1}$)

Elemental Analysis:

Anal Calc: C, 46.50; H, 5.46; N, 10.85; S, 12.41

Anal Found: C, 46.48; H, 5.65; N, 10.90; S, 12.07

$^1$H NMR (CDCl$_3$) δ 6.86 (m, 4H), 4.52 (bs, 2H), 4.46 (m, 1H), 4.29 (dd, J=2.3, 11.5 Hz, 1H), 4.05 (dd, J=6.5, 11.5 Hz, 1H), 3.51 (dd, J=6.7, 14.9 Hz, 1H), 3.40 (dd, J=5.9, 14.9 Hz, 1H), 2.99 (s, 3H).

Example 7

(2S)-(−)-N-(6-Chloro-2,3-dihydro-benzo[1,4]dioxin-2-ylmethyl)-sulfamide (Compound #8)

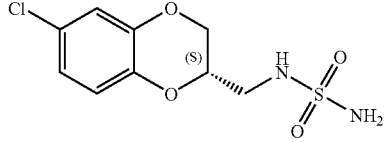

Following the procedure outlined in Example 4 above, 4-chlorocatechol was reacted to yield a mixture of (2S)—C-(7-Chloro-2,3-dihydro-benzo[1,4]dioxin-2-yl)-methylamine and (2S)—C-(6-Chloro-2,3-dihydro-benzo[1,4]dioxin-2-yl)-methylamine (ca. 3:1 ratio of 6-chloro:7-chloro isomers by RP HPLC).

The mixture was dissolved in 2-propanol (100 mL) and 1N HCl in diethyl ether was added until pH=1.0 was attained. The hydrochloride salt that precipitated was filtered (2.65 g) and re-crystallized from methanol/IPA to yield white crystals. The white crystals were partitioned between DCM and dilute NaOH. The DCM was dried and evaporated in vacuo to yield purified (2S)—C-(6-Chloro-2,3-dihydro-benzo[1,4]dioxin-2-yl)-methylamine as an oil.

[α]$_D$=−67.8 (c=1.51, CHCl$_3$)

The oil (7.75 mmol) and sulfamide (1.50 g, 15.5 mmol) were combined in dioxane (50 mL) and refluxed for 2.0 h, cooled to room temperature and evaporated in vacuo to yield a solid. The product was purified via flash column using DCM/methanol 20:1 to yield the title compound as a white solid.

MS 277 (M$^{-1}$)

[α]$_D$=−59.9° (c=1.11, M)

$^1$H NMR (CDCl$_3$) δ 6.90 (d, J=2.2 Hz, 1H), 6.81 (m, 2H), 4.76 (m, 1H), 4.55 (s, 2H), 4.40 (m, 1H), 4.29 (dd, J=2.4, 11.5 Hz, 1H), 4.05 (dd, J=7.1, 11.5 Hz, 1H), 3.45 (m, 2H)

Elemental Analysis:

Anal Calc: C, 38.78; H, 3.98; N, 10.05

Anal Found: C, 38.80; H, 3.67; N, 9.99.

The filtrates of the crystallized hydrochloride salt of (2S)—C-(6-Chloro-2,3-dihydro-benzo[1,4]dioxin-2-yl)-methylamine prepared above were recovered (ca. 1:1 of 6-chloro:7-chloro isomers) and evaporated in vacuo to yield a solid, which was partitioned between DCM (200 mL) and dilute NaOH (0.5 M, 50 mL). The DCM solution was washed once with brine, dried (Na$_2$SO$_4$) and evaporated in vacuo to yield an oil, which was purified via reverse phase HPLC (10-50% ACN with 0.16% TFA in water with 0.20% TFA) to yield (2S)—C-(7-Chloro-2,3-dihydro-benzo[1,4]dioxin-2-yl)-methylamine as a residue.

The residue was combined with sulfamide (0.90 g, 9.4 mmol) in dioxane (25 mL) and refluxed for 2.5 h, cooled to room temperature and evaporated in vacuo to yield an oil. The oil was purified by flash column chromatography using DCM/methanol—10:1 to yield (2S)-(−)-N-(7-Chloro-2,3-dihydro-benzo[1,4]dioxin-2-ylmethyl)-sulfamide as a white solid.

MS 277 (M$^{-1}$)

$^1$H NMR (CDCl$_3$/CD$_3$OD) δ 6.88 (d, J=0.7 Hz, 1H), 6.81 (m, 2H), 4.37 (m, 1H), 4.30 (dd, J=2.3, 11.6 Hz, 1H), 4.04 (dd, J=7.0, 11.6 Hz, 1H), 3.38 (m, 2H).

Example 8

Chroman-2-ylmethylsulfamide (Compound #10)

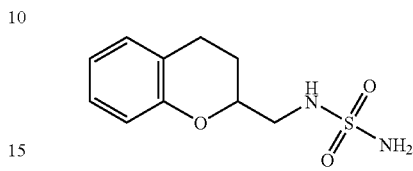

Chroman-2-carboxylic acid (4.5 g, 25 mmol) and HOBT (3.86 g, 25 mmol) were combined in DCM (40 mL) and DMF (10 mL). Dimethylaminopropyl ethylcarbodiimide (EDC, 4.84 g, 25 mmol) was added at room temperature and the reaction mixture was stirred for 30 min. Ammonium hydroxide (2.26 mL, 33.4 mmol) was added and the reaction mixture was stirred for 16 h. The reaction mixture was diluted with DCM (50 mL) and water (50 mL) and the pH of the mixture was adjusted to about pH=3.0 with 1N HCl. The DCM was separated and the aqueous phase extracted twice with DCM. The combined DCM phase was dried (Na$_2$SO$_4$) and evaporated in vacuo to yield an oil, which was purified with flash column chromatography (ethyl acetate) to yield an oil.

The oil (5.35 g, 30 mmol) in THF (90 mL) was stirred as 1M LAH in THF (36 mL, 36 mmol) was added and the reaction mixture was then stirred at room temperature for 20 h. The reaction was quenched with water, stirred for 2 hours, the solution decanted, dried (Na$_2$SO$_4$) and evaporated in vacuo to yield C-chroman-2-yl-methylamine as an oily amine.

The oily amine (1.63 g, 10 mmol) and sulfamide (1.92 g, 20 mmol) were combined in dioxane (50 mL) and brought to reflux for 2 h. The solution was cooled and evaporated in vacuo to yield an oil, which was purified via column chromatography (DCM:Methanol 10:1) to yield a white solid. The solid was recrystallized from ethyl acetate/hexane to yield chroman-2-ylmethylsulfamide as a white solid.

mp 100-101° C.

MS 241 (M$^{-1}$)

Elemental Analysis:

Anal Calc: C, 49.57; H, 5.82; N, 11.56; S, 13.23

Anal Found: C, 49.57; H, 5.80; N, 11.75; S, 13.33.

Example 9

2-(2,3-Dihydro-benzo[1,4]dioxin-2-yl)-ethylsulfamide (Compound #16)

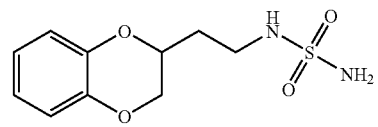

Potassium cyanide (2.05 g, 31.5 mmol) was added to 2-bromomethyl-(2,3 dihydrobenzo[1,4]dioxine) (6.87 g, 30 mmol) in DMSO (90 mL) and stirred at ambient temperature for 20 h. The reaction mixture was then diluted with water (250 mL) and extracted twice with diethyl ether. The diethyl ether was washed with water, then washed twice with brine, dried (Na$_2$SO$_4$) and evaporated in vacuo to yield 2-cyanomethyl-(2,3 dihydrobenzo[1,4]dioxine) as a white solid.

$^1$H NMR (CDCl$_3$) δ 6.89 (m, 4H), 4.50 (m, 1H), 4.31 (dd, J=2.3, 11.5 Hz, 1H), 4.08 (dd, J=6.2, 11.6 Hz, 1H), 2.78 (d, J=6.1, Hz, 2H)

The 2-cyanomethyl-(2,3 dihydrobenzo[1,4]dioxine) was dissolved in THF (50 mL) and 1M BH$_3$ in THF (80 mL, 80 mmol) was added and the reaction mixture refluxed for 5 h, then stirred at ambient temperature for 16 h. With ice bath cooling, 2N HCl was added until pH=1.0 was achieved. The reaction mixture was then stirred for 1 h at room temperature and evaporated in vacuo to yield an oil. The oil was partitioned between 3N NaOH and diethyl ether, and the diethyl ether solution was washed with brine, dried (Na$_2$SO$_4$) and evaporated in vacuo to yield crude 2-(2,3 dihydrobenzo[1,4]dioxin-2-yl)ethylamine.

MS (M+H)$^+$ 180.

The crude 2-(2,3 dihydrobenzo[1,4]dioxin-2-yl)ethylamine in dioxane (100 mL) was combined with sulfamide (3.0 g, 31 mmol) and heated to reflux for 2 h. The solution was cooled and evaporated in vacuo to yield an orange solid, which was purified by column chromatography (DCM:MeOH—10:1) to yield a white solid. The solid was re-crystallized from DCM to yield the title compound as a solid.

MS (M-1) 257
MP 101-103° C. (corr)
$^1$H NMR (CDCl$_3$): δ 6.86 (m, 4H), 4.70 (m, 1H), 4.52 (s, 2H), 4.30 (m, 2H), 3.94 (dd, J=7.4, 11.3 Hz, 1H), 3.43 (dd, J=6.4, 12.9 Hz, 2H), 1.94 (dd, J=6.5, 12.9, 2H).
Elemental Analysis:
Measured: C, 46.48; H, 5.60; N, 10.81; S, 12.41
Calculated: C, 46.50; H, 5.46; N, 10.85; S, 12.41

Example 10

(2S)-(-)-N-(6,7 Dichloro-2,3-dihydro-benzo[1,4]dioxin-2-ylmethyl)-sulfamide (Compound #29)

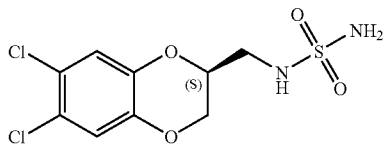

4,5 Dichloroatechol (8.6 g, 48 mmol) and potassium carbonate (6.64 g, 48 mmol) were stirred in DMF (200 mL). (2R)-Glycidyl tosylate (9.12 g, 40 mmol) was added and the reaction mixture was stirred at 60° C. for 24 h. The reaction mixture was cooled to room temperature and then diluted with ice water (600 mL) and extracted with diethyl ether (4 times). The combined organic solution was washed 3 times with 10% potassium carbonate, twice with brine, dried (MgSO$_4$) and evaporated in vacuo to yield a viscous oil of (2S)-2-(6,7-dichloro-2,3-dihydro-benzo[1,4]dioxine) methanol.

The (2S)-2-(6,7 dichloro-2,3-dihydro-benzo[1,4]dioxine) methanol oil (6.4 g, 27 mmol) was dissolved in pyridine (50 mL) cooled to 0° C. Then, p-toluenesulfonyl chloride (5.2 g, 27 mmol) was added and the reaction mixture was stirred at room temperature for 20 h. The reaction mixture was diluted with diethyl ether and 1N HCl (750 mL) and the organic layer was separated and washed 2 times with 1N HCl (250 mL), once with water (150 mL), twice with brine, dried (MgSO$_4$) and evaporated in vacuo to yield light yellow solid of toluene-4-sulfonic acid (2S)-6,7-dichloro-2,3-dihydro-benzo[1,4]dioxin-2-ylmethyl ester.

$^1$H NMR (CDCl3): δ 7.79 (d, J=8.3 Hz, 2H), 7.36 (d, J=8.0 Hz, 2H), 6.94 (s, 1H), 6.83 (s, 1H), 4.37 (m, 1H), 4.2 (m, 3H), 4.03 (dd, J=6.3, 11.7 Hz, 1H), 2.47 (s, 3H).

Toluene-4-sulfonic acid (2S)-6,7-dichloro-2,3-dihydro-benzo[1,4]dioxin-2-ylmethyl ester (8.0 g, 20.5 mmol) was combined with potassium phthalimide (6.1 g, 33 mmol) in DMF (75 mL) and heated to reflux for 1 h, cooled to room temperature and poured into vigorously stirring water (0.5 L) and then stirred 30 min. White solid was filtered and the solid was washed several times with water, 2% NaOH, and water again and then let air dry to yield (2S)-2-(6,7-dichloro-2,3-dihydro-benzo[1,4]dioxin-2-ylmethyl)-isoindole-1,3-dione (6.0 g, 80%) as a white powdery solid.

The white powdery solid was combined with hydrazine (1.06 g, 33 mmol) in EtOH (80 mL) and heated at reflux for 2 h, then cooled to room temperature. 1N HCl was added to adjust the reaction mixture's pH to pH 1.0 and the reaction mixture was then stirred for 15 min. White solid was filtered and washed with fresh EtOH (solid discarded) and the filtrate was evaporated in vacuo to a solid, which was partitioned between diethyl ether and dilute aqueous NaOH. The diethyl ether solution was dried (Na$_2$SO$_4$) and evaporated in vacuo to a yield a viscous oil of (2S)-2-aminomethyl-(6,7-dichloro-2,3-dihydro-benzo[1,4]dioxine).

$^1$H NMR (CDCl3): δ 6.98 (s, 1H), 6.96 (s, 1H), 4.25 (dd, J=2.0, 11.2 Hz, 1H), 4.15 (m, 1H), 4.0 (m, 1H), 2.97 (d, J=5.5 Hz, 2H)

A portion of the oil (3.8 g, 16 mmol) and sulfamide (3.1 g, 32.4 mmol) were refluxed in dioxane (100 mL) for 2 h and the crude product was purified by flash column chromatography (DCM:MeOH 20:1) to yield the title compound as a white solid, which was recrystallized from ethyl acetate/hexane to yield the title compound as a white crystalline solid.

MS [M-H]$^-$ 311.0
mp 119-121° C.
[α]$_D$=-53.4° (c=1.17, M)
$^1$H NMR (DMSO d6): δ 7.22 (s, 1H), 7.20 (s, 1H), 6.91 (bd s, 1H), 6.68 (bd s, 2H), 4.35 (m, 2H), 4.05 (dd, J=6.5, 11.5 Hz, 1H), 3.15 (m, 2H)
Elemental Analysis:
Elemental Analysis:
Measured: C, 34.52; H, 3.22; N, 8.95; Cl, 22.64; S, 10.24
Calculated: C, 34.64; H, 2.68; N, 8.87; Cl, 22.94; S, 10.35.

Example 11

(2S)-(-)-N-(7-Amino-2,3-dihydro-benzo[1,4]dioxin-2-ylmethyl)-sulfamide (Compound #36)

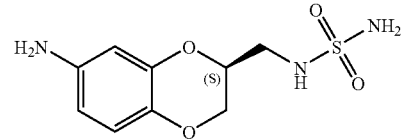

(2S)-(-)-N-(2,3-Dihydro-7-nitro-benzo[1,4]dioxin-2-ylmethyl)-sulfamide (1.2 g, 4.15 mmol), was prepared from 4-nitrocatechol according to the process outlined in Example 4. The (2S)-(-)-N-(2,3-Dihydro-7-nitro-benzo[1,4]dioxin-2-ylmethyl)-sulfamide, was then combined with 10% Pd/C in methanol (120 mL) and shaken under hydrogen atmosphere (39 psi) at room temperature for 3 h. The solids were filtered and washed with 10% M in DCM and the filtrate was evaporated in vacuo to yield crude product. The crude product was dissolved in 0.2 N HCl (25 mL), frozen and lyophilized to yield the title compound as a white flaky solid, as the corresponding hydrochloride salt.

MS (M+H)$^+$ 260

$^1$H NMR (DMSO d6): δ 10.2 (bd s, 3H), 6.86 (m, 1H), 6.85 (s, 1H), 6.74 (dd, J=2.5, 8.4 Hz, 1H), 4.22 (m, 2H), 3.88 (dd, J=6.7, 11.4 Hz, 1H), 3.04 (m, 2H)

Example 12

(2S)-(−)-N-(7-Methyl-2,3-dihydro-benzo[1,4]dioxin-2-ylmethyl)-sulfamide (Compound #19)

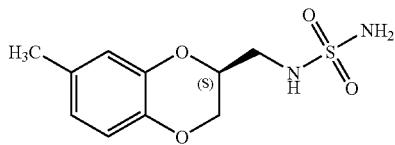

Title compound was prepared according to the procedure described in Example 4 above, starting with 4-methylcatechol, to yield a white solid, which was recrystallized from ethyl acetate/hexane to yield the title compound as a white solid.

MS [M−H]$^-$257

$^1$H NMR (CDCl3): δ 6.76 (m, 1H), 6.66 (m, 2H), 4.80 (m, 1H), 4.57 (bd s, 1H), 4.40 (m, 1H), 4.28 (m, 1H), 4.03 (dd, J=6.9, 11.4 Hz, 1H), 3.45 (m, 2H), 2.25 (s, 3H).

Elemental Analysis

Calculated: C, 46.50; H, 5.46; N, 10.85; S, 12.41

Found: C, 46.65; H, 5.60; N, 10.84; S, 12.61.

Example 13

Dominant-Submissive Relations (DSR) in Rat In Vivo Assay

The DSR assay is divided into two models: Reduction of Dominant Behavior Model (RDBM) of mania and Reduction of Submissive Behavior Model (RSBM) of depression. The RDBM, wherein the dominant animals are treated with test compound, is predictive of the ability of the test compound to treat mania. The RSBM, wherein the submissive animals are treated with test compound, is predictive of the ability of the test compound to treat depression.

Male Sprague Dawley rats (140 to 160 g) from Charles River Laboratories Wilmington, Mass. were used in this assay. Shipments of rats were received at two-week intervals. Each shipment went through five-day quarantine, one-week acclimation period, and one-week selection process, followed by five-weeks of drug or vehicle treatment to those pairs selected.

Rats were housed four per cage. Access to food was restricted to one hour per day after testing on Monday through Thursday. After testing on Friday, rats had free access to food until being fasted again on Sunday. At no time were the rats deprived of water. The food deprivation periods used had little effect on weight gain as the average weight of rats was about 300 g at the end of the study. At the conclusion of experiment rats were sacrificed by decapitation, the trunk blood and brains were collected for in vitro experiments and drug concentration measurements.

The basic testing apparatus consisted of two chambers connected with a tunnel only large enough to allow one rat to pass through at a time. On the floor, at the mid-point of the tunnel was a container of sweetened milk. This basic apparatus was replicated, so that a total of four pairs of rats can be video tracked simultaneously. The camera can distinguish rats marked by different colors. Thus, the rats' heads were colored for the purpose of video tracking, red in one cage and yellow in the other cage. Only one animal at a time can have comfortable access to the feeder, but both animals can drink milk during the five-minute daily session. During the five-minute daily sessions, time spent in the feeder zone by each rat was recorded by the video tracking software and saved into a text file.

The test began with a random assignment of rats into pairs. Each member of a pair was placed in an opposite chamber of the testing apparatus. The time spent in the feeder zone by each animal was recorded. During the first week (five days) of testing the animals habituate to the new environment. Dominance was assigned to the animal with the highest score during the second week of testing if three criteria were achieved. First, there must have been a significant difference (two-tailed t-test, P<0.05) between the average daily drinking scores of both animals. Second, the dominant animal score must have been at least 25% greater than the submissive animal's score. Finally, there must have been no "reversals" during the pair selection week where the putative submissive rat out-scored its dominant partner on isolated occasions. Ideally there were minimal reversals during the acclimation week as well. About twenty-five to thirty-three percent of the initial animal pairs achieved these criteria and only these pairs were continued in the study.

Significant differences between time spent on the feeder by dominant and submissive rats were determined by ANOVA using GraphPad Prism software (GraphPad Software, Inc. San Diego, Calif.) followed by a two-tailed t-test (P<0.05). Comparisons were made between treatment groups using normalized dominance level values in paired animals. The dominance level is a value that measures social relation between paired subjects. Dominance level (DL)=FTD−FTS where FTD is the feeder time of dominant rats and FTS is the feeder time of submissive rats. The normalization was conducted according to the formula:

Dominance Level(week $n$ in %)=(Dominance Level (week $n$))/(Dominance Level(week 2)

The statistical significance of the difference in dominance level between the control group (pairs of rats where both dominant and submissive animals were treated with vehicle) and the treatment group (submissive rats were treated with drug and dominant rats with vehicle) was determined by ANOVA, followed by a t-test. The activity onset time value at 50% of response (AOT-50) and the minimum and maximum response to drug were calculated based on the reduction of the dominance level value using non-linear regression analysis (GraphPad Software, Inc., San Diego, Calif.). The normalized DL values were used for this calculation, where DL values for treatment weeks were normalized as a percent of the second week (pretreatment) value of that pair according the above formula. In these settings the minimum of the response (DL) determined drug positive activity, corresponding to efficacy, since DL values were always reduced if the response to a drug was positive. In the case of the negative response to a drug (worsening of symptoms) DL values were increased. If the drug did not have such activity the maximum of the response did not exceed 100%. Any maximal DL value significantly higher then control value (about 100%) indicated drug negative activity.

Compound #8 was evaluated in the rat RDBM according to the procedure described in more detail below.

Groups of dominant rats were treated p.o. QD with Compound #8; at 0.05 mg/kg (n=4), at 0.5 mg/kg (n=6), at 2.5 mg/kg (n=6), at 5.0 mg/kg n=6) and at 50.0 mg/kg (n=3). A vehicle control group of dominant rats was treated with 0.5% methylcellulose (n=3) and a second control group of dominant rats was treated i.p. QD with sodium valproate at 30 mg/kg (n=6 from 2 studies of n=3 each).

All treatments were administered approximately 1 hour prior to testing. All treatments started on Saturday after the second testing week (selection week). Compound #8 was administered orally (p.o).

When dominant animals were treated with Compound #8 at 0.05 mg/kg, 0.5 mg/kg and 50.0 mg/kg, the difference between dominant and submissive rats was lost after the first week of treatment; and after the second week of treatment when dosed at 2.5 mg/kg and 5.0 mg/kg. Similarly, when dominant animals were treated with sodium valproate, the difference between dominant and submissive rats was also lost after first week of treatment. In this study, the permissiveness of the dominant rats treated with Compound #8 or sodium valproate was observed to increase. Thus the treated dominant rats permitted their submissive partners to increase their time on the feeder.

To compare different drug and dose effects the data were normalized to the initial control week values. The strongest effect of Compound #8 was observed at a dosage of 0.5 mg/kg with a significant difference in dominance level (DL) values between vehicle and compound treated rats starting in the second week and continuing through the treatment duration of 5 weeks. Higher doses of Compound #8 (2.5 mg/kg, 5.0 mg/kg, and 50.0 mg/kg) showed a weaker response, which was not significantly different from that observed with the 0.5 mg/kg dose.

In comparison, sodium valproate treated animals (30 mg/kg) consistently showed a decreased dominance level after the second week of treatment with the effect increasing in the following weeks. The effect of lithium chloride (100 mg/kg) was significantly different from control only after the third week of treatment.

To estimate activity onset time (AOT), daily average values for feeder time of dominant and submissive animal pairs were plotted and significant differences between these two groups were calculated using the two-tail t-test. The first day of consistent lack of statistical significance occurred after treatment with Compound #8 at 0.05 mg/kg on the $3^{rd}$ day; at 0.5 mg/kg on the $4^{th}$ day, at 2.5 mg/kg on the $10^{th}$ day, at 5.0 mg/kg on the $11^{th}$ day and at 50.0 mg/kg on the $3^{rd}$ day.

To compare activity onset time (AOT) between different treatments the activity onset time was estimated from the non-linear regression fit. The non-linear regression model was fit for each drug and dose normalized daily DL values. $AOT_{50}$ for Compound #8 at 0.05 mg/kg and 0.5 mg/kg was significantly shorter from that of lithium.

Effects of Compound #8 in the RDBM were dose dependent, with a calculated $ED_{50}$ of 0.03±0.004 mg/kg [CI=0.01-0.04] and and $E_{max}$ of 116.4±2.3% [CI=109.2-123.6].

In this assay, Compound #8 reduced dominant behavior indicating that the compound is active as an anti-manic agent.

Example 14

Dominant-Submissive Relations (DSR) in Rat In Vivo Assay

The DSR assay is divided into two models: Reduction of Dominant Behavior Model (RDBM) of mania and Reduction of Submissive Behavior Model (RSBM) of depression. The RDBM, wherein the dominant animals are treated with test compound, is predictive of the ability of the test compound to treat mania. The RSBM, wherein the submissive animals are treated with test compound, is predictive of the ability of the test compound to treat depression.

Male Sprague Dawley rats (140 to 160 g) from Charles River Laboratories Wilmington, Mass. were used in this assay. Shipments of rats were received at two-week intervals. Each shipment went through five-day quarantine, one-week acclimation period, and one-week selection process, followed by five-weeks of drug or vehicle treatment to those pairs selected.

Rats were housed four per cage. Access to food was restricted to one hour per day after testing on Monday through Thursday. After testing on Friday, rats had free access to food until being fasted again on Sunday. At no time were the rats deprived of water. The food deprivation periods used had little effect on weight gain as the average weight of rats was about 300 g at the end of the study. At the conclusion of experiment rats were sacrificed by decapitation, the trunk blood and brains were collected for in vitro experiments and drug concentration measurements.

The basic testing apparatus consisted of two chambers connected with a tunnel only large enough to allow one rat to pass through at a time. On the floor, at the mid-point of the tunnel was a container of sweetened milk. This basic apparatus was replicated, so that a total of four pairs of rats can be video tracked simultaneously. The camera can distinguish rats marked by different colors. Thus, the rats' heads were colored for the purpose of video tracking, red in one cage and yellow in the other cage. Only one animal at a time can have comfortable access to the feeder, but both animals can drink milk during the five-minute daily session. During the five-minute daily sessions, time spent in the feeder zone by each rat was recorded by the video tracking software and saved into a text file.

The test began with a random assignment of rats into pairs. Each member of a pair was placed in an opposite chamber of the testing apparatus. The time spent in the feeder zone by each animal was recorded. During the first week (five days) of testing the animals habituate to the new environment. Dominance was assigned to the animal with the highest score during the second week of testing if three criteria were achieved. First, there must have been a significant difference (two-tailed t-test, P<0.05) between the average daily drinking scores of both animals. Second, the dominant animal score must have been at least 25% greater than the submissive animal's score. Finally, there must have been no "reversals" during the pair selection week where the putative submissive rat out-scored its dominant partner on isolated occasions. Ideally there were minimal reversals during the acclimation week as well. About twenty-five to thirty-three percent of the initial animal pairs achieved these criteria and only these pairs were continued in the study.

Terminal blood samples (0.5-1.0 mL) were collected post experiment into heparinized tubes. Blood samples were centrifuged for cell removal, and 200 µL of plasma supernatant was then transferred to a clean vial, placed on dry ice, and subsequently stored in a −80° C. freezer prior to analysis. Two hundred microliters of acetonitrile containing internal standard was added to 100 μL of plasma or brain tissue to precipitate proteins and/or tissue residues. Samples were centrifuged and supernatant removed for analysis by liquid chromatography-triple quadruple mass spectrometry (LC-MS-MS). Calibration standards were prepared by adding appropriate volumes of stock solution directly into blank plasma or brain tissue homogenates and treated identically to collected samples. Calibration standards were prepared in the range of 0.01 to 10 μM for quantitation. LC-ESI-MS/MS (negative mode) analysis was performed utilizing multiple reaction monitoring (MRM) for detection of characteristic ions for the test compound.

Significant differences between time spent on the feeder by dominant and submissive rats were determined by ANOVA using GraphPad Prism software (GraphPad Software, Inc. San Diego, Calif.) followed by a two-tailed t-test (P<0.05). Comparisons were made between treatment groups using normalized dominance level values in paired animals. The dominance level is a value that measures social relation between paired subjects. Dominance level (DL)=FTD−FTS where FTD is the feeder time of dominant rats and FTS is the feeder time of submissive rats. The normalization was conducted according to the formula:

Dominance Level(week $n$ in %)=(Dominance Level (week $n$))/(Dominance Level(week 2)

The statistical significance of the difference in dominance level between the control group (pairs of rats where both dominant and submissive animals were treated with vehicle) and the treatment group (submissive rats were treated with drug and dominant rats with vehicle) was determined by ANOVA, followed by a t-test. The activity onset time value at 50% of response (AOT-50) and the minimum and maximum response to drug were calculated based on the reduction of the dominance level value using non-linear regression analysis (GraphPad Software, Inc., San Diego, Calif.). The normalized DL values were used for this calculation, where DL values for treatment weeks were normalized as a percent of the second week (pretreatment) value of that pair according the above formula. In these settings the minimum of the response (DL) determined drug positive activity, corresponding to efficacy, since DL values were always reduced if the response to a drug was positive. In the case of the negative response to a drug (worsening of symptoms) DL values were increased. If the drug did not have such activity the maximum of the response did not exceed 100%. Any maximal DL value significantly higher then control value (about 100%) indicated drug negative activity.

Compound #8 was evaluated in the Rat Reduction of Submissive Behavior Model (RSBM) of depression (Malatynska, E., Rapp, R., Harrawood, D., and Tunnicliff, G., *Neuroscience and Biobehavioral Review*, 82 (2005) 306-313; Malatynska, E., and Knapp, R. J., *Neuroscience and Biobehavioral Review*, 29 (2005) 715-737).

More specifically, Compound #8 was administered p.o. (orally) to the submissive rats at 2.5 mg/kg (n=8), 12 mg/kg (n=12), 60 mg/kg (n=12) and 120 mg/kg (n=7), once a day for 5 weeks while the dominant partners were dosed with vehicle (0.5% aqueous methylcellulose). As controls, additional groups of rats were treated i.p. with fluoxetine at 10.0 mg/kg (n=10) and i.p. venlafaxine at 30.0 mg/kg (n=6). All treatments were administered approximately 1 hour prior to testing. Compound #8 was observed to reduce submissive behavior in a dose-dependent manner.

When submissive animals were treated with Compound #8, the significant difference between dominant and submissive rats was lost after the first week of treatment. This was true for all doses used, indicating that the onset of activity was independent from the dose. By contrast, when submissive animals were treated with fluoxetine the significant difference between dominant and submissive rats was lost after third week of treatment. (This method of data analysis did not take into account the fluctuation of behavior that occurs in the control group.) To compare different drug and dose effects the data were normalized to the initial control week values.

Dominance Level (DL) values in the group of submissive rats treated with 2.5 mg/kg dose of Compound #8 did not significantly differ from control. However, the group treated with Compound #8 at 12.0 mg/kg showed DL values significantly different from vehicle treated controls after the second, fourth and fifth week of treatment. Similarly, the group treated with Compound #8 at 60 mg/kg showed a significant difference in DL values relative to vehicle starting at the first week and continuing through the treatment duration of 5 weeks. At the highest dose, (120 mg/kg) Compound #8 DL values were significantly different from the control group after first week, however, this significance dissipated after the second week of treatment.

Fluoxetine treated animals (10 mg/kg) consistently showed increased submissiveness during first week of treatment. In comparison with fluoxetine treated animals (10 mg/kg), Compound #8 treated groups did not show this effect. At 60.0 mg/kg dose of Compound #8, the difference in DL values with fluoxetine treated group was statistically significant at p<0.001 after first week and p<0.05 after second week of treatment. There was no significant difference between normalized DL levels of pairs treated with fluoxetine and Compound #8 during subsequent treatment weeks.

To estimate activity onset time, daily average values for feeder time of dominant and submissive animal pairs were plotted and significant differences between these two groups were calculated using the two-tail t-test. The first day of consistent lack of statistical significance occurred after treatment with Compound #8 at 12.0 mg/kg on the $6^{th}$ day and at 60 mg/kg on the $4^{th}$ day. There was no consistent loss of significance between dominant and submissive rats feeder time after treatment with Compound #8 at 2.5 mg/kg and 120.0 mg/kg.

To compare activity onset time between different treatments the activity onset time was estimated from the non-linear regression fit. The non-linear regression model was fit for each drug and dose normalized daily DL values. Activity Onset Time at the 50% effect ($AOT_{50}$) and Emax for Compound #8 at 2.5 mg/kg, 12 mg/kg and 60 mg/kg was 2.1; 5.3 and 1.6 days, respectively and was not significantly different between doses. The maximum of the effect derived from this analysis was 52.4±32.7% (SEM), 87.9±42.6% (SEM) and 116.9±29.5% (SEM) for the 2.5 mg/kg, 12 mg/kg and 60 mg/kg dose respectively and was also not significantly different between these doses.

In summary, the effect of Compound #8 in the RSBM assay was dose dependent, with a calculated $ED_{50}$ of 6.6±0.8 mg/kg [CI=3.0-10.2] and $E_{max}$ of 131.4±4.7% [CI=111.3-151.5].

In this assay, Compound #8 reduced submissive behavior indicating that the compound is active as an anti-depressant agent.

Example 15-17 KINDLING AND BIPOLAR CYCLING

Discussion in current literature suggests that the mechanisms underlying kindling may be similar to the mechanism of cycling in bipolar disorder and/r may be related to mood stabilization. Thus, the amygdala kindling and hippocampal kindling assays described in more detail hereinafter may be predictive of the ability of a test compounds to treat the cycling associated with, characteristic of or symptomatic of bipolar disorder. (Ghaemi, S. N., Boiman, E. E., and Goodwin, F. K., *Soc. of Bio. Psychiatry*, (1999), vol. 45, pp 137-144; Stoll, A. L., and Severus, W. E., *Harvard Rev. Psychiatry*, July/August (1996), Vol. 4, No. 2, pp 77-89)

Example 15

Amygdala Kindling Assay (Kindling Prevention)

Briefly, the assay procedure was as follows. Adult male, Sprague-Dawley rats weighing between 250-300 g were obtained from Charles River, Wilmington, Mass. All the animals were housed on a 12:12 light dark cycle and permitted free access to both food (Prolab RMH 3000) and water except when removed from the home cage for experimental procedures. Animals were cared for in a matter consistent with the recommendations detailed in the National Research Council Publication, "Guide for the Care and Use of Laboratory Animals" in a temperature controlled, pesticide-free facility. Kindling stimulations were routinely performed between 9 AM-2 PM to avoid any circadian variations.

Compound #8 was triturated in a small volume of 0.5% methylcellulose, sonicated for 10 min, and brought to a final volume with 0.5% methylcellulose. Compound #8 was administered systemically (i.p.) in a volume of 0.04 ml/10 g body weight and all tests were conducted at the pre-determined time of peak effect of 0.5 hours after i.p. administration.

The ability of Compound #8 to block the expression of amygdala kindled seizures was determined as follows. Rats were anaesthetized with a ketamine (120 mg/kg, i.p.) and xylazine (12 mg/kg, i.p.) cocktail. Under aseptic conditions, a bipolar electrode (Plastic One, Roanoke, Va.) was stereotaxically implanted into the right basolateral amygdala (AP −2.2, ML −4.7, DV −8.7; Paxinos and Watson). Anterior-posterior and lateral measurements were from Bregma, whereas the dorsal-ventral measurement was from the skull surface. Sterile skull screws (3-4) were implanted for the indifferent reference electrode. Electrodes were fixed using dental cement and acrylic. The wound was then closed using sterile 18/8 Michel suture clips (Roboz, Gaithersburg, Md.). Neomycin antibiotic ointment was applied to the wound and a single dose of penicillin (60,000 IU, im, AgriLabs) was administered to the each rat before returning them to clean cages for one week of post operative recovery.

Amygdala kindling was then performed according to the following protocol. Following a brief acclimation (<5 minutes) to the recording chamber, baseline EEG recordings were obtained (MP 100, Biopac Systems Inc., Goleta, Calif.). Rats were then randomized to receive either vehicle (0.5% methylcellulose) or Compound #8 (75 mg/kg, i.p.) (n=10 rats per group). On the day of the experiment, a single dose of Compound #8 or 0.5% methylcellulose was administered 30 minutes prior to amygdala stimulation (200 µA for 2 seconds). The behavioral seizure score and AD duration was recorded for rats in each treatment group. Behavioral seizure scores were determined using the Racine scale; i.e., 0=no response; stage 1=grooming/hyperactivity; stage 2=head nodding/tremor; stage 3=unilateral forelimb clonus; stage 4=clonus with rearing; and stage 5=generalized tonic-clonic seizure with rearing and falling (Racine, 1972). After-discharge (AD) activity was digitally recorded for up to 180 seconds following the stimulation train and the duration of the primary AD was measured. Rats were considered fully kindled when they displayed five consecutive Stage 4 or 5 generalized seizures. Daily stimulations were continued for up to 13 consecutive days in all three groups until rats in the vehicle-treated group were fully kindled (i.e., five consecutive Stage 4 or 5 seizures). At this time, all rats were allowed a one-week stimulus and drug-free period; after which they were re-challenged in the absence of drug with the same stimulus employed during the acquisition phase (i.e., days 1-13). Rats treated with Compound #8 were subsequently stimulated once per day until they reached a fully kindled state.

The after-discharge (AD) duration in both the vehicle and Compound #8 treated groups displayed a progressive increase over the course of the kindling acquisition phase. No statistical difference between treatment groups was observed.

Compound #8 prevented the acquisition of the full generalized kindled seizure. This conclusion is based on the finding that the seizure score at the conclusion of the drug- and stimulus-free period remained significantly lower than that of the rats in the vehicle-treated group (Compound #8=1.4±0.40 vs. vehicle=4.6±0.24). Additionally, when stimulated in the absence of drug, the seizure score of rats in the Compound #8 treatment group increased at a rate that was parallel to that observed in the vehicle-treated rats—supporting the conclusion that Compound #8 delayed the acquisition of kindling by several days.

The results of this study demonstrate that Compound #8 possesses the ability to modify the development of kindling in the amygdala kindled rat model of partial epilepsy. These results are consistent with the conclusion that Compound #8 possesses disease-modifying effects. This conclusion is based on the finding that the seizure score, at the conclusion of the drug- and stimulation-free period, of rats in the Compound #8 treatment group remained significantly lower than that of the vehicle-treated rats. Furthermore, once the stimulation protocol was resumed in the absence of drug, the seizure score progressed at a rate that was parallel to the vehicle-treated group.

The finding that the seizure score, but not the after-discharge duration, in the compound treatment group one-week after the stimulus- and drug-free week was markedly lower than that of the vehicle-treated group suggests that Compound #8 prevented the acquisition of the secondarily generalized seizure but not the focal seizure.

Example 16

Hippocampal Kindling Model (Interruption of Kindled State)

Kindled seizures provide an experimental model of focal seizures, allowing scientists to study complex brain networks that may contribute to seizure spread and generalization from a focus.

In the present rapid hippocampal kindling model adult male Sprague-Dawley rats (300-400 g) were surgically implanted with bipolar electrodes placed in the hippocampus. The rats were kindled by repetitive electrical stimulation (50 Hz, 10 s train of 1 ms, biphasic 200 µA pulses every 30 min for 6 h every other day for a total of 60 stimulations) resulting in stage 5 bilateral motor seizures. One week later, the rats received 2-3 supra-threshold stimulations delivered every 30 min before treatment with test compound, to ensure stability of the behavioral seizure stage and after-discharge duration. Fifteen minutes after the last stimulation, a single dose of vehicle or test compound was administered i.p. (intraperitoneally). After 15 min, each rat was then stimulated every 30 min for 3 to 4 h. After each stimulation, individual seizure scores and after-discharge durations were recorded. The group mean±SEM were calculated for each parameter. Eight rats per dose and a minimum of four doses were used to establish an $ED_{50}$ value. Efficacy was measured as the ability of a compound to modify the seizure score (severity of spread) and after-discharge duration (ADD; excitability) of the generalized seizures.

Using this approach, a compound that reduces the seizure score from 5 to 3 without any effect on the ADD suggest the utility of the compound for the treatment of secondarily generalized seizures. In contrast, a compound that reduces the seizure score from 5 to less than 1, as well as reduces the ADD, suggest the utility of the compound for the treatment of focal seizures. Thus, according to the theories presented in current literature (Ghaemi, S. N., Boiman, E. E., and Goodwin, F. K., *Soc. of Bio. Psychiatry*, (1999), vol. 45, pp 137-144; Stoll, A. L., and Severus, W. E., *Harvard Rev. Psychiatry*, July/August (1996), Vol. 4, No. 2, pp 77-89) a decrease in seizure score and/or ADD may also be predictive of the ability of a test compound to treat the cycling associated with bipolar disorder.

Compound #8 (formulated in a 0.5% aqueous solution of methylcellulose) exhibited anticonvulsant activity in this model with an $ED_{50}$=68.5±1.3 mg/kg (corresponding to a decrease in seizure score at 45 min, and peak activity at 165 min). Seizure scores were significantly reduced from 5 to 1 in 4 out of 8 rats (p=0.0003). There was no statistically significant effect on the ADD (p=0.07). Ethosuximide was ineffective in this model; whereas, phenytoin, carbamazepine and valproic acid significantly suppressed seizure activity, but at doses associated with toxicity.

In this model, 6 out of 8 rats showed a significant reduction in global seizure activity (score <3) after treatment with Compound #8, as shown in FIG. 5. Similar protection was observed for valproic acid (at toxic doses >300 mg/kg) and carbamazepine (at toxic doses >26 mg/kg).

Comparison Results from this assay are as listed in Table 4, below.

TABLE 4

Evaluation of Compound #8 and Reference Drugs in the Rat Hippocampal Kindling Test

| | Dose (mg/kg), i.p. | Mean Seizure Score | After-Discharge Duration (% of control) |
|---|---|---|---|
| Compound #8 | 100 | 2.1 ± 0.5 | 153 ± 24% |
| | $TD_{50}$~100 | (p = 0.0003) | (p = 0.07) |
| Ethosuximide | 250 | 5 ± 0.1 | 78 ± 13% |
| | $TD_{50}$ = 189 | (p = 0.20) | (p = 0.03) |
| Phenytoin | 30 | 4.3 ± 0.3 | 209 ± 43% |
| | $TD_{50}$ = 15 | (p = 0.02) | (p = 0.02) |
| Carbamazepine | 75 | 2.3 ± 0.6 | 72 ± 13% |
| | $TD_{50}$ = 26 | (p = 0.005) | (p = 0.02) |
| Valproic acid | 350 | 0.3 ± 0.2 | 3 ± 1% |
| | $TD_{50}$ = 316 | (p < 0.0001) | (p < 0.0001) |

$ED_{50}$ = median therapeutic dose; $TD_{50}$ = median toxic dose
P = paired t-test; one-tailed Example 17

Lamotrigine Resistant Amygdala Kindled Rat Model (Interruption of Kindled State)

Compound #8 was evaluated in the lamotrigine (LTG)-resistant amygdala kindled rat model (NINDS). Amygdala kindling is less severe than hippocampal kindling, such that many AEDs are effective against amygdala kindled seizures, but are ineffective against hippocampal kindled seizures. For example, lamotrigine can significantly reduce amygdala kindled seizure score and ADD ($ED_{50}$=25 mg/kg, i.p., Cl=4-50 mg/kg; score ~2; ADD reduced by 62%), but is unable to protect against hippocampal kindled seizures.

In the LTG-resistant amygdala kindling model, rats were dosed with LTG (5 mg/kg, i.p., q.d.) during the acquisition phase of kindling. This dose has been shown to have no effect on kindling itself, but leads to the development of fully kindled rats that are resistant to the anticonvulsant effects of LTG. Once kindled (supra-threshold stimulation of 150 μA biphasic 60 Hz current pulse for 1 second; ~2 weeks), rats were re-challenged with a high dose of LTG (45 mg/kg, i.p.) one week later to insure resistance. After a 3-4 day wash out period, rats received 2-3 supra-threshold stimulations delivered every 30 min before treatment with Compound #8 (or vehicle) to ensure stability of the behavioral seizure stage and after-discharge duration. Fifteen minutes after the last stimulation, a single dose of vehicle or test compound was administered i.p. After 15 min, each rat was then stimulated every 30 min for 3 to 4 h. After each stimulation, individual seizure scores and after-discharge durations were recorded. The group mean±SEM was calculated for each parameter.

Compound #8 (75 mg/kg, i.p., n=9) significantly reduced the seizure score and after-discharge duration. Eight out of nine rats were protected such that the seizure score was reduced from a 5 to 0.8 and the after-discharge duration was reduced 86% (from 73 sec to 10 sec). Four of the nine rats exhibited ataxia and sedation at this dose.

Example 18

Tail Suspension Test (Acute)

In the tail suspension test (TST) for evaluating compounds for anti-depressant activity, mice are suspended by their tails to a metal or plastic rod using clip or scotch tape. The test is usually quite short, 5-7 min, and the amount of time the mice spend immobile is recorded either manually or with an automated device. Agents which have antidepressant activity, decrease the duration of immobility of mice in this test.

The basic apparatus for the tail suspension assay consisted of a yellow plastic chamber (91×45×10 cm) divided for four arenas 25, 20, 20 and 25 cm wide separated by yellow plastic walls 0.75 cm thick. Mice were suspended by their tails using a rubber clip (7 cm long) attached to the plastic rod that was placed on the top of a testing chamber half way through its deep dimension. Each experimental session was videotaped and analyzed for four animals in the real time by computer software ("Depression Scan" Clever Sys Inc.). The computer justification of immobility was calibrated with the use of animals dosed with lorazepam while justification of movement was calibrated with the high dose of desipramine treated animals. Control, vehicle treated animals and animals treated with Compound #8 were analyzed under the calibrated settings. The settings were adjusted separately for dark (CH3/HeJ and C57BI/6J strains) and white mice (Balb/cJ and A/J strains). A yellow background was used for dark mice and a blue background was used to record movements of white mice.

The ability of a test compound to decrease the duration of immobility, or increase mobility was measured using the TST procedure described above. Acute treatment with clinically effective antidepressants and/or novel compounds that have potential antidepressant properties decrease the duration of immobility and at the same time increases mobility in the TST.

Data were analyzed using GraphPad Prism software (GraphPad Software, Inc. San Diego, Calif.). For the comparison of the effect of different doses for various drugs on immobility in the TST one-way analyses of variance (ANOVA) were used followed by Dunnett's multiple comparison test. The $ED_{50}$ and $E_{max}$ values were calculated for DMI, VLX, DLX and Compound #8 using non-linear regression analysis with one phase exponential decay equation for curve fitting. The $ED_{50}$ and $E_{max}$ values were compared using two-way ANOVA and Bonferroni post-hoc test.

The dose-response for different antidepressants and Compound #8 in the $CH_3/HeJ$ mice was evaluated. Compound #8 was suspended in 0.5% of methylcellulose. Positive controls included duloxetine (DLX), venlafaxine (VLX) and desipramine (DMI) which were dissolved in 0.5% methylcellulose and lorazepam (LOR) which was suspended in 0.5% of methylcellulose in water by sonication. All drugs and vehicles were administered orally (p.o.) by gavage in a volume of 10 mL/kg.

The mice were ordered 5 weeks old and at the beginning of experiment their weight was 20±5 g. Animals were housed in groups of four in plastic cages at an ambient temperature of 21° C. to 23° C. with an automated 12/12 hours light/dark cycle and access to water and a commercial rodent food ad libitum.

This group was divided into eight experiments testing the effects of Compound #8, positive controls (DMI, VLX, DLX) at different doses and negative control (LOR) at 5 mg/kg. Each experiment consisted of seven treatment groups with four animals per group. A total of 28 animals per experiment were used. Every two consecutive experiments (1 & 2, 3 & 4, 5 & 6 and 7 & 8) were exact replicas of each other. This resulted in a total number of eight animals per treatment group at the end of the study. One treatment group of four animals in each experiment was a vehicle treated group. In addition to the vehicle treated group, the effects of DMI at 6 mg/kg, 12 mg/kg, 30 mg/kg, 60 mg/kg and 120 mg/kg and LOR at 5 mg/kg were tested in experiments 1 and 2. In experiments 3 and 4 the effects of Compound #8 at 6 mg/kg, 12 mg/kg, 30 mg/kg, 60 mg/kg, 120 mg/kg and 240 mg/kg were tested. In experiments 5 and 6 the effects of DLX at 6 mg/kg, 12 mg/kg, 30 mg/kg, 60 mg/kg, 120 mg/kg and LOR at 5 mg/kg were tested. In experiments 7 and 8 the effects of VLX at 6 mg/kg, 12 mg/kg, 30 mg/kg, 60 mg/kg, 120 mg/kg and LOR at 5 mg/kg were tested. In the course of the study one mouse died due to miss-dosing in the group treated with Compound #8 12 mg/kg, so this group consisted of seven animals on the end of the study.

Compound #8 and all tested antidepressant drugs decreased immobility time and increased mobility time in CH3/HeJ mice during a 7-min testing session. Compound #8 effects were statistically significant at 12 mg/kg, 60 mg/kg, and 120 mg/kg. Significance was determined in comparison to parallel controls treated with vehicle.

DMI effects were statistically significant at 12, 30, 60 and 120 mg/kg. VLX effects were statistically significant at 6, 12, 30, 60 and 120 mg/kg. DLX effects were statistically significant at 60 and 120 mg/kg.

$ED_{50}$ and $E_{max}$ values were calculated from these results by non-linear regression analysis. $ED_{50}$ and $E_{max}$ values are listed in Table 5 below. $ED_{50}$ values calculated for immobility and mobility were not significantly different across treatments. The $ED_{50}$ value for Compound #8 was significantly lower than the $ED_{50}$ value for DLX but not different than the $ED_{50}$ values for DMI and VLX. The $E_{max}$ values calculated for immobility and mobility were not significantly different for Compound #8 but were significantly different for all tested antidepressant. The $E_{max}$ immobility value for Compound #8 was also significantly lower then than antidepressant drug values.

TABLE 5

$ED_{50}$ and $E_{max}$ Values for Different Drugs in the TST

| Mobility | | | |
| --- | --- | --- | --- |
| Drug | $ED_{50}$ mg/kg | SEM $ED_{50}$ | CI |
| Cmpd #8 | 3.6 | 2.9 | −4.6-11.8 |
| DMI | 24.4 | 9.0 | −0.5-49.3 |
| VLX | 21.1 | 8.4 | −2.1-44.4 |
| DLX | 61.5 | 20.9 | 3.6-119.3 |
| Drug | $E_{max}$ % of C | SEM $E_{max}$ | CI |
| Cmpd #8 | 95.6 | 13.0 | 59.4-131.7 |
| DMI | 195.7 | 24.9 | 126.7-264.7 |
| VLX | 412.6 | 53.9 | 263.0-562.2 |
| DLX | 175.5 | 28.3 | 96.9-254.2 |
| Immobility | | | |
| Drug | $ED_{50}$ mg/kg | SEM $ED_{50}$ | CI |
| Cmpd #8 | 5.6 | 3.3 | 1.7-12.1 |
| DMI | 27.4 | 16.0 | 11.3-55.0 |
| VLX | 25.0 | 15.4 | 8.8-55.1 |
| DLX | 31.4 | 15.7 | 22.4-42.6 |
| Drug | $E_{max}$ % of C | SEM $E_{max}$ | CI |
| Cmpd #8 | 22.2 | 6.1 | 2.8-41.6 |
| DMI | 38.5 | 6.3 | 18.5-58.5 |
| VLX | 63.7 | 11.1 | 28.4-98.9 |
| DLX | 80.4 | 6.4 | 59.9-100.9 |

In summary, studies described in this example show that Compound #8 has antidepressant-like activity, as measured by the tail suspension test. The $ED_{50}$ for Compound #8 was calculated as 3.6±2.9 mg/kg and the $E_{max}$ calculated as 22.2±6.1% under the condition of our study.

Example 19

Forced Swim Test (Acute)

The Forced Swim test (FST) is a commonly used procedure to screen compounds for possible antidepressant properties. This test is also known as the behavioral despair test. Rodents placed in familiar tanks filled with water present a wide variety of escape or immobility behaviors. Antidepressant drugs from different classes markedly increase escape behaviors and/or decrease latency or duration of immobility. Since these effects are characteristic of clinically active antidepressants the compounds with unknown clinical activity showing such effects in the FST are interpreted to have potential to treat human mood disorders.

Compound #8 and maprotyline were dissolved in 10% solutol. Venlafaxine and desipramine were dissolved in water. All drugs and their vehicles were administered orally (p.o.) by gavage in a volume of 5 mL/kg.

Male Sprague Dawley rats (140 to 160 g) from Charles River Laboratories Wilmington, Mass. were used. The animals went through a five-day quarantine period before being subjected to the experimental procedure.

Animals were housed in groups of four in plastic cages at an ambient temperature of 21° C. to 23° C. with an automated 12 hour light/dark cycle and access to water and commercial rodent food ad libitum. Animals were not handled more than for the routine bedding change prior to pre-test swim session.

The study was divided into six experiments testing the effects of Compound #8, three positive controls (desipramine, maprotyline, venlafaxine) and a negative control (lorazepam) at different doses. Each experiment consisted of seven treatment groups with n=4 animals per group. A total of 28 animals per experiment were used. Two consecutive experiments (1 and 2, 3 and 4, and 5 and 6) were exact replicas of each other. This resulted in a total number of eight animals per treatment group at the end of the study. One treatment group of n=4 animals in each experiment was a vehicle treated group. In addition to the vehicle treated group, the effects of desipramine at 3 mg/kg, 6 mg/kg, 12 mg/kg, 30 mg/kg and 60 mg/kg and lorazepam at 1 mg/kg were tested in experiments 1 and 2. In experiments 3 and 4 the effects of Compound #8 at 3 mg/kg, 6 mg/kg, 12 mg/kg, 30 mg/kg, 60 mg/kg and 120 mg/kg were tested. In experiments 5 and 6 the effects of venlafaxine and maprotyline at 12 mg/kg, 30 mg/kg, and 60 mg/kg were tested. In the course of the study one rat died due to miss-dosing in group treated with desipramine 12 mg/kg, so this group consisted of seven animals on the end of the study.

The basic apparatus consisted of a cylinder (46 cm tall×~20 cm diameter) filled with water to 30 cm deep, at a temperature of 25±1° C. The automated version of the FST was used to perform the experiments. Plumbing for automatic filling and emptying water connected the four cylinders. Cylinders were placed in the dividing chambers 25 cm wide to separate animals visually. Each 5-minute experimental session was videotaped and analyzed in real time by computer software (Clever Systems, Inc.) for four animals at a time. The immobility, swimming, climbing and escape times were recorded by the software. The four activities are defined as follow. Immobility: the animal floats motionlessly or makes only those movements necessary to keep its head above water; Climb: the animal vigorously moves vertically while scratching the wall around the cylinder; Swim: the animal moves horizontally around in the cylinder more than necessary to keep its head above water; and Escape: sum of all vigorous active movements.

The ability of a test compound to decrease the duration or frequency of immobility, or changes in swimming, climbing and escape times, was measured using the FST procedure described above. Clinically effective antidepressants and/or novel compounds that have potential antidepressant properties decrease the duration or frequency of immobility in the FST when administered between the pre-test and the test sessions. The analysis of the results in the studies described was focused on the immobility time during 5-minute test session.

There were two swim sessions in each experiment. First, a pre-test swim session for 15 minutes was performed. Following 48 hours later was a test session of 5-minute duration. Upon completion of a swim session, each animal was placed under a heat lamp in a cage with soft bedding for approximately 15 minutes to prevent hypothermia.

Animals were pre-treated with a vehicle or test compound after completing the pre-test swim session, then 24 hours later and then shortly prior to the 5-minute test session; i.e., three injections were given to each animal between the two swim sessions that occurred on 3 consecutive days. The time prior to test session was 1 hour for desipramine, maprotyline, venlafaxine, lorazepam or 4 hours for Compound #8; the time of the maximal effect in the maximal electroshock seizures (MES) test.

Data were analyzed using GraphPad Prism software (GraphPad Software, Inc. San Diego, Calif.). For the comparison of the effect of different doses for various drugs on immobility in the FST one-way ANOVA was used followed by Dunnett's multiple comparison test. The $ED_{50}$ and $E_{max}$ values were calculated for desipramine and Compound #8 using non-linear regression analysis with a one-phase exponential decay equation for curve fitting. The $ED_{50}$ and $E_{max}$ values were statistically compared using two-tail t-test.

All tested antidepressant drugs decreased immobility time during the 5-minute testing session. The desipramine effect was statistically significant at 6 mg/kg, 12 mg/kg, 30 mg/kg, and 60 mg/kg. The calculated $ED_{50}$ for desipramine was 2.0±0.1 mg/kg (Cl=1.3-3.3 mg/kg) and its $E_{max}$ was 50.0±8.4 seconds (Cl=31.8-57.7). The effect of treatment with Compound #8 was statistically significant at 12 mg/kg, 60 mg/kg, and 120 mg/kg compared to vehicle treated controls. The large variability between individual rats rendered the effect of the 30 mg/kg dose of Compound #8 not significantly different from control. For this reason the immobility data for 30 mg/kg dose were not used in the $ED_{50}$ calculation. The $ED_{50}$ calculated for Compound #8 was 5.6±0.6 mg/kg (Cl=2.2-15.6 mg/kg) and its $E_{max}$ was 67.0±11.6 seconds (Cl=30.3-103.8). The $ED_{50}$ value for Compound #8 was significantly different from the $ED_{50}$ value for desipramine at $p<0.001$ (two tail t-test). There was no statistically significant difference between $E_{max}$ values for desipramine and Compound #8. Venlafaxine and maprotyline (positive controls) were tested only at three doses of 12 mg/kg, 30 mg/kg, and 60 mg/kg. The immobility of animals treated at the 30 mg/kg and 60 mg/kg doses were significantly different from vehicle-treated controls for both venlafaxine and maprotyline. However, there were too few data points to calculate an $ED_{50}$ for these two drugs. Lorazepam (negative control) was tested at 1 mg/kg and showed no significant effect on the rats' immobility time during the testing session. The results indicate that Compound #8 has antidepressant-like activity in the FST.

TABLE 6

$ED_{50}$ and $E_{max}$ values for Compound #8 and DMI in the FST

|  | $ED_{50}$ mg/kg | SEM $ED_{50}$ | CI $ED_{50}$ | $E_{max}$ % | SEM $E_{max}$ | CI $E_{max}$ |
| --- | --- | --- | --- | --- | --- | --- |
| Compound #8 | 5.6 | 0.6 | 2.2-15.6 | 57.0 | 11.6 | 30.3-103.8 |
| DMI | 2.0 | 0.1 | 1.3-3.3 | 50.0 | 8.4 | 31.8-57.7 |

Example 20

Chronic Mild Stress Model (Chronic)

In the chronic mild stress (CMS) model rats subjected to a variety of mild stressors for a prolonged period of time show, among other behavioral, biochemical and physiological impairments, a substantial decrease in their responsiveness to rewarding stimuli. This deficit is usually monitored by a decrease in the consumption of the 1% sucrose solution, but can also be seen in other tests, such as place preference conditioning or intracranial self-stimulation. Since the sub-sensitivity to reward appears to reflect anhedonia (inability to experience pleasure), which is a core symptom of major depressive disorders, the CMS procedure may serve as a suitable research tool in studies into the mechanisms of anti-depressant action.

Male Wistar rats were brought into the laboratory two months before the start of the experiment. Except as described below, the animals were singly housed with food and water freely available, and were maintained on a 12-h light/dark and in a constant temperature (22±2° C.) and humidity (50±5%) conditions.

The animals were first trained to consume a 1% sucrose solution; training consisted of eight 1 h baseline tests in which sucrose was presented, in the home cage, following 14 h food and water deprivation; the sucrose intake was measured by weighing pre-weighed bottles containing the sucrose solution, at the end of the test. Subsequently, sucrose consumption was monitored, under similar conditions, at weekly intervals throughout the whole experiment.

On the basis of their sucrose intakes in the final baseline test, the animals were divided into two matched groups. One group of animals was subjected to the chronic mild stress procedure for a period of 7 consecutive weeks. Each week of stress regime consisted of: two periods of food or water deprivation, two periods of 45 degree cage tilt, two periods of intermittent illumination (lights on and off every 2 h), two periods of soiled cage (250 ml water in sawdust bedding), one period of paired housing, two periods of low intensity stroboscopic illumination (150 flashes/min), and three periods of no stress. All stressors were 10-14 h of duration and were applied individually and continuously, day and night. Control animals were housed in separate rooms and had no contact with the stressed animals. They were deprived of food and water for the 14 h preceding each sucrose test, but otherwise food and water were freely available in the home cage.

On the basis of their sucrose intakes following initial 2 weeks of stress, both stressed and control animals were each divided further into matched subgroups (n=8), and for subsequent five weeks they received once daily intraperitoneal administration of vehicle (0.5% methylcellulose, 1 ml/kg), Compound #8 at 12 mg/kg, 30 mg/kg or 60 mg/kg, imipramine at 10 g/kg or venlafaxine at 10 mg/kg as reference treatments. The drugs were administered at approx. 10.00 and the weekly sucrose tests were carried out 24 h following the last drug injections. After five weeks all treatments were terminated and 24 h later the blood and/or brain samples were collected from all animals and submitted for further biochemical analysis. Stress was continued throughout the entire period of treatment.

Animals were individually removed from their housing rooms to another room for sacrifice. Then they were decapitated in a semi-randomized order. Whole brains were be removed, rapidly frozen in dry ice/n-heptane immediately after sacrifice and stored in plastic vials at −70° C. Trunk blood for plasma was collected into EDTA tubes which contained EDTA (approximately 1.6 mg/ml of blood). The EDTA blood was centrifuged directly at 1500×g for 10 min at 4° C. The plasma was aspirated and stored in Eppendorf tubes at −70° C. Additionally, 2 lots of 20 ml of plasma from naïve animals were prepared for generating a compound standard curve for bioanalysis.

All results obtained in this study were analyzed by multiple analyses of variance with three between-subjects factors (stress/control, drug treatments and successive sucrose tests). The Fisher's LSD test was used for the post-hoc comparisons of means.

Chronic mild stress caused a gradual decrease in the consumption of 1% sucrose solution. In the final baseline test, all animals drank approx. 11 g of sucrose solution. Following the initial two weeks of stress, intakes remained at a similar level in controls but fell to approx. 6 g in stressed animals, resulting in a significant Group effect [$F(1,84)=87.204$; $p<0.001$]. Such a difference between control and stressed animals treated with vehicle, persisted at similar level for the remainder of the experiment.

As compared to vehicle administration, Imipramine was inactive in controls [Treatment effect: $F(1,84)=1.578$; NS] and caused significant Treatment effect: $F(1,84)=22.651$; $p<0.001$ and Treatment×Weeks interaction: $F(5,84)=2.717$; $p=0.025$] in stressed animals. Similarly, Venlafaxine was inactive in controls [Treatment effect: $F(1,84)=0.208$; NS] and caused significant Treatment effect: $F(1,84)=35,724$; $p<0.001$ and Treatment×Weeks interaction: $F(5,84)=3.219$; $p=0.010$] in stressed animals.

As compared to Week 0 scores, the increases in sucrose intake in stressed animals reached statistical significance after four weeks of treatment with imipramine ($p<0.05$) and venlafaxine ($p<0.01$) and this effect was maintained thereafter. One stressed animal (no 480) did not respond to venlafaxine treatment but it was not excluded from the statistical analysis.

As compared to vehicle administration, Compound #8 did not cause significant Treatment effects in control [$F(3,168)=1.198$; NS] and in stressed [$F(3,168)=1.676$; NS] animals, indicating that the compound is inactive in the CMS model of depression.

Example 21

Resident I Intruder Assay (Also Known as Chronic Social Stress Assay)

The behavioral resident/intruder assay is used to screen compounds for anti-depressant-like activity. Compound #8 was tested in this assay, with the assay run according to the procedure as described in Rygula, R., Abumaria, N., Flugge, G., Fuchs, E., Ruther, E., Havemann-Reinecke, U., *Behavioral Brain Research*, 162 (2005), pp 127-134.

Tables 5, 6 and 7 below, list the mean and standard deviation values for measured parameters, for the following compounds, administered p.o. (orally): vehicle, control compounds imipramine at 10 mg/kg and venlafaxine at 10 mg/kg, Compound #8 at 60 mg/kg and Compound #8 at 120 mg/kg.

TABLE 5

Resident Intruder Effect on Sucrose Intake

| Treatment | Dose mg/kg | Sucrose Intake Mean ± SD | | |
|---|---|---|---|---|
| | | Week 3 | Week 4 | Week 5 |
| Vehicle - non-stressed | 0 | 90.2 ± 2.5* | 89.0 ± 4.2* | 91.7 ± 2.1* |
| Vehicle - stressed | 0 | 51.7 ± 26.7 | 69.3 ± 7.5 | 66.3 ± 6.1 |
| Imipramine - non-stressed | 10 | 87.9 ± 2.7 | 89.7 ± 5.3 | 91.0 ± 3.7 |
| Imipramine - stressed | 10 | 70.5 ± 19.5 | 78.3 ± 15.1 | 73.6 ± 19.4 |
| Venlafaxine - non-stressed | 10 | 88.4 ± 9.1 | 91.5 ± 5.6 | 87.9 ± 15.0 |
| Venlafaxine - stressed | 10 | 74.5 ± 16.7 | 76.1 ± 18.2 | 73.3 ± 17.6 |
| Compound #8 - non-stressed | 60 | 90.9 ± 3.5 | 92.3 ± 1.4 | 88.9 ± 7.4 |
| Compound #8 - stressed | 60 | 92.1 ± 3.2* | 89.5 ± 6.9* | 92.4 ± 4.5* |
| Compound #8 - non-stressed | 120 | 83.6 ± 22.1 | 91.3 ± 4.6 | 89.3 ± 5.1 |
| Compound #8 - stressed | 120 | 76.1 ± 20.8 | 75.5 ± 20.6 | 87.4 ± 7.9* |

*statistically significantly different from vehicle stressed animals

TABLE 6

Resident Intruder Effect on Locomotor Activity

| Treatment | Dose mg/kg | Locomotor Mean ± SD | Rearing Mean ± SD | Sniffing Up Mean ± SD | Sniffing Down Mean ± SD |
|---|---|---|---|---|---|
| Vehicle non-stressed | 0 | week 1<br>8184.7 ± 1597.2<br>week 5<br>8102.3 ± 1805.6* | week 1<br>50.8 ± 10.2*<br>week 5<br>46.8 ± 7.6* | week 1<br>47.8 ± 9.6<br>week 5<br>43 ± 6.6* | week 1<br>24.5 ± 4.9<br>week 5<br>29.8 ± 5.3* |
| Vehicle stressed | 0 | week 1<br>5816.8 ± 1589.6<br>week 5<br>3920.8 ± 887.3 | week 1<br>28 ± 11.2<br>week 5<br>18 ± 9.1 | week 1<br>27.5 ± 10.8<br>week 5<br>14.5 ± 6.7 | week 1<br>15.8 ± 5.7<br>week 5<br>9 ± 2.6 |
| Imipramine non-stressed | 10 | week 1<br>8162.8 ± 929.9<br>week 5<br>7278 ± 1030 | week 1<br>51.5 ± 12.6<br>week 5<br>42.1 ± 2.9 | week 1<br>48.1 ± 10.3<br>week 5<br>37.5 ± 2.1 | week 1<br>25.8 ± 4.9<br>week 5<br>26.4 ± 5.2 |
| Imipramine stressed | 10 | week 1<br>6037.8 ± 1382.8<br>week 5<br>5642.8 ± 998.6 | week 1<br>30 ± 9.5<br>week 5<br>27.8 ± 7.4 | week 1<br>27.5 ± 7.9<br>week 5<br>24.3 ± 5.1 | week 1<br>14.4 ± 4.4<br>week 5<br>17.3 ± 3.4* |
| Venlafaxine non-stressed | 10 | week 1<br>9094.9 ± 1832.7<br>week 5<br>8078.6 ± 1665.2 | week 1<br>48.3 ± 11.2<br>week 5<br>40.1 ± 8.9 | week 1<br>43.3 ± 8.9<br>week 5<br>38.6 ± 7.7 | week 1<br>27.1 ± 5.2<br>week 5<br>27 ± 4.7 |
| Venlafaxine stressed | 10 | week 1<br>6233.6 ± 1087.2<br>week 5<br>6250.1 ± 789.2* | week 1<br>30.8 ± 6.6<br>week 5<br>35.1 ± 7.4 | week 1<br>28.6 ± 6.5<br>week 5<br>33.1 ± 7.5* | week 1<br>14.9 ± 3.5<br>week 5<br>18.3 ± 3.6* |
| Compound #8 non-stressed | 60 | week 1<br>8288.6 ± 2117.5<br>week 5<br>7922.9 ± 1476 | week 1<br>49.6 ± 8.7<br>week 5<br>37.4 ± 11.5 | week 1<br>44.1 ± 9.4<br>week 5<br>33.4 ± 11.2 | week 1<br>20.9 ± 3.3<br>week 5<br>23.5 ± 6.4 |
| Compound #8 stressed | 60 | week 1<br>5858.5 ± 708.2<br>week 5<br>7080.9 ± 1238.7* | week 1<br>26.5 ± 6.1<br>week 5<br>32.8 ± 10.3 | week 1<br>25 ± 7.3<br>week 5<br>30.6 ± 11.1 | week 1<br>13 ± 3.3<br>week 5<br>24.8 ± 5.7* |
| Compound #8 non-stressed | 120 | week 1<br>8056.6 ± 867.2<br>week 5<br>8648.3 ± 1060.9 | week 1<br>42 ± 10.6<br>week 5<br>36.5 ± 6.3 | week 1<br>37.6 ± 8.4<br>week 5<br>33.5 ± 5.9 | week 1<br>22.8 ± 3.7<br>week 5<br>25.5 ± 4.1 |
| Compound #8 stressed | 120 | week 1<br>6168.3 ± 1132.1<br>week 5<br>6444 ± 1010.3* | week 1<br>29.3 ± 7<br>week 5<br>30.1 ± 6.4 | week 1<br>27.5 ± 6.1<br>week 5<br>30.4 ± 7.5 | week 1<br>13 ± 3.6<br>week 5<br>22.5 ± 4.1* |

*statistically significantly different from vehicle stressed animals

TABLE 7

Resident Intruder Effect on Forced Swim Test

| Treatment | Dose mg/kg | Immobility during 5 min: Week 5 Mean ± SD |
|---|---|---|
| Vehicle - non-stressed | 0 | 165.5 ± 25* |
| Vehicle - stressed | 0 | 227 ± 40.2 |
| Imipramine - non-stressed | 10 | 125.3 ± 50.1 |
| Imipramine - stressed | 10 | 157.5 ± 71.6 |
| Venlafaxine - non-stressed | 10 | 181.8 ± 27.6 |
| Venlafaxine - stressed | 10 | 190.4 ± 36.8 |
| Compound #8 - non-stressed | 60 | 164.3 ± 25.3 |
| Compound #8 - stressed | 60 | 175.1 ± 29.5 |
| Compound #8 - non-stressed | 120 | 136.7 ± 34.9 |
| Compound #8 - stressed | 120 | 128.3 ± 37.4* |

*statistically significantly different from vehicle stressed animals

Compound #8 was active in the resident/intruder assay indicating that Compound #8 would be expected to be active as an anti-depressant.

Example 22

As a specific embodiment of an oral composition, 100 mg of the Compound #8 prepared as in Example 7 is formulated with sufficient finely divided lactose to provide a total amount of 580 to 590 mg to fill a size 0 hard gel capsule.

While the foregoing specification teaches the principles of the present invention, with examples provided for the purpose of illustration, it will be understood that the practice of the invention encompasses all of the usual variations, adaptations and/or modifications as come within the scope of the following claims and their equivalents.

We claim:

1. A method for treating bipolar mania comprising administering to a subject with bipolar mania in need of treatment, a therapeutically effective amount of a compound of formula (I)

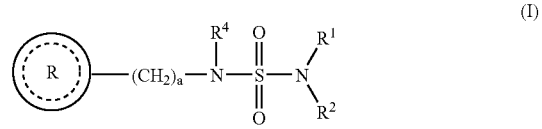

wherein
$R^1$ and $R^2$ are each independently selected from the group consisting of hydrogen and lower alkyl;
$R^4$ is selected from the group consisting of hydrogen and lower alkyl;
a is an integer from 1 to 2;

 is

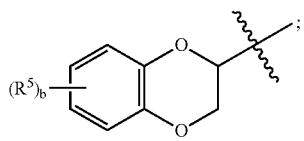

wherein b is an integer from 0 to 4;
each $R^5$ is independently selected from the group consisting of halogen, and lower alkyl;
or a pharmaceutically acceptable salt thereof.

2. The method as in claim 1, wherein
$R^1$ and $R^2$ are each independently selected from the group consisting of hydrogen and lower alkyl;
$R^4$ is selected from the group consisting of hydrogen and lower alkyl;
a is an integer from 1 to 2;

is

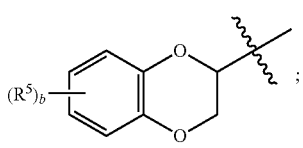

wherein b is an integer from 0 to 2; each $R^5$ is independently selected from the group consisting of halogen, and lower alkyl;
or a pharmaceutically acceptable salt thereof.

3. The method as in claim 2, wherein
$R^1$ and $R^2$ are each independently selected from the group consisting of hydrogen and lower alkyl;
$R^4$ is selected from the group consisting of hydrogen and methyl;
a is an integer from 1 to 2;

is selected from the group consisting of 2-(2,3-dihydro-benzo[1,4]dioxinyl), 2-(6-chloro-2,3-dihydro-benzo[1,4]dioxinyl), 2-(6-fluoro-2,3-dihydro-benzo[1,4]dioxinyl), 2-(5-fluoro-2,3-dihydro-benzo[1,4]dioxinyl), 2-(7-chloro-2,3-dihydro-benzo[1,4]dioxinyl), 2-(7-methyl-2,3-dihydro-benzo[1,4]dioxinyl), 2-(5-chloro-2,3-dihydro-benzo[1,4]dioxinyl), 2-(6-bromo-2,3-dihydro-benzo[1,4]dioxinyl), 2-(6,7-dichloro-2,3-dihydro-benzo[1,4]dioxinyl), and 2-(8-chloro-2,3-dihydro-benzo[1,4]dioxinyl);
or a pharmaceutically acceptable salt thereof.

4. The method as in claim 3, wherein
$R^1$ and $R^2$ are each independently selected from the group consisting of hydrogen and methyl;
$R^4$ is selected from the group consisting of hydrogen and methyl;
a is an integer from 1 to 2;

is selected from the group consisting of 2-(2,3-dihydro-benzo[1,4]dioxinyl), 2-(6-chloro-2,3-dihydro-benzo[1,4]dioxinyl), 2-(7-chloro-2,3-dihydro-benzo[1,4]dioxinyl), 2-(7-methyl-2,3-dihydro-benzo[1,4]dioxinyl), 2-(6-bromo-2,3-dihydro-benzo[1,4]dioxinyl) and 2-(6,7-dichloro-2,3-dihydro-benzo[1,4]dioxinyl);
or a pharmaceutically acceptable salt thereof.

5. The method of claim 1, wherein the compound of formula (I) is (2S)-(−)-N-(6-chloro-2,3-dihydro-benzo[1,4]dioxin-2-ylmethyl)-sulfamide or a pharmaceutically acceptable salts thereof.

6. A method of treating bipolar mania comprising administering to a subject with bipolar mania in need of treatment, a therapeutically effective amount of (2S)-(−)-N-(6-chloro-2,3-dihydro-benzo[1,4]dioxin-2-ylmethyl)-sulfamide or a pharmaceutically acceptable salts thereof.

7. A method for treating bipolar disorder comprising administering to a subject with bipolar mania in need of treatment, a therapeutically effective amount of a compound of formula (I)

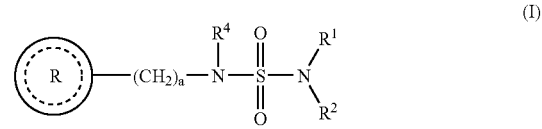

wherein
$R^1$ and $R^2$ are each independently selected from the group consisting of hydrogen and lower alkyl;
$R^4$ is selected from the group consisting of hydrogen and lower alkyl;
a is an integer from 1 to 2;

is

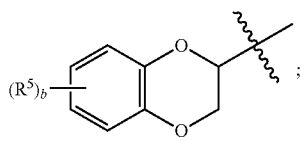

wherein b is an integer from 0 to 4;
each $R^5$ is independently selected from the group consisting of halogen, and lower alkyl;

or a pharmaceutically acceptable salt thereof.

8. The method as in claim 7, wherein
$R^1$ and $R^2$ are each independently selected from the group consisting of hydrogen and lower alkyl;
$R^4$ is selected from the group consisting of hydrogen and lower alkyl;
a is an integer from 1 to 2;

is

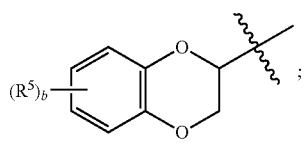

wherein b is an integer from 0 to 2;
each $R^5$ is independently selected from the group consisting of halogen, and lower alkyl;
or a pharmaceutically acceptable salt thereof.

9. The method as in claim 8, wherein
$R^1$ and $R^2$ are each independently selected from the group consisting of hydrogen and lower alkyl;
$R^4$ is selected from the group consisting of hydrogen and methyl;
a is an integer from 1 to 2;

is selected from the group consisting of 2-(2,3-dihydro-benzo[1,4]dioxinyl), 2-(6-chloro-2,3-dihydro-benzo[1,4]dioxinyl), 2-(6-fluoro-2,3-dihydro-benzo[1,4]dioxinyl), 2-(5-fluoro-2,3-dihydro-benzo[1,4]dioxinyl), 2-(7-chloro-2,3-dihydro-benzo[1,4]dioxinyl), 2-(7-methyl-2,3-dihydro-benzo[1,4]dioxinyl), 2-(5-chloro-2,3-dihydro-benzo[1,4]dioxinyl), 2-(6-bromo-2,3-dihydro-benzo[1,4]dioxinyl), 2-(6,7-dichloro-2,3-dihydro-benzo[1,4]dioxinyl), and 2-(8-chloro-2,3-dihydro-benzo[1,4]dioxinyl);
or a pharmaceutically acceptable salt thereof.

10. The method as in claim 9, wherein
$R^1$ and $R^2$ are each independently selected from the group consisting of hydrogen and methyl;
$R^4$ is selected from the group consisting of hydrogen and methyl;
a is an integer from 1 to 2;

is selected from the group consisting of 2-(2,3-dihydro-benzo[1,4]dioxinyl), 2-(6-chloro-2,3-dihydro-benzo[1,4]dioxinyl), 2-(7-chloro-2,3-dihydro-benzo[1,4]dioxinyl), 2-(7-methyl-2,3-dihydro-benzo[1,4]dioxinyl), 2-(6-bromo-2,3-dihydro-benzo[1,4]dioxinyl) and 2-(6,7-dichloro-2,3-dihydro-benzo[1,4]dioxinyl);
or a pharmaceutically acceptable salt thereof.

11. The method of claim 7, wherein the compound of formula (I) is (2S)-(−)-N-(6-chloro-2,3-dihydro-benzo[1,4]dioxin-2-ylmethyl)-sulfamide or a pharmaceutically acceptable salts thereof.

12. The method of claim 7, wherein the method of treating bipolar disorder comprises treating the mania of bipolar disorder.

13. The method of claim 7, wherein the method of treating bipolar disorder comprises treating the mania and the cycling of bipolar disorder.

14. A method of treating bipolar disorder comprising administering to a subject with bipolar mania in need of treatment, a therapeutically effective amount of (2S)-(−)-N-(6-chloro-2,3-dihydro-benzo[1,4]dioxin-2-ylmethyl)-sulfamide or a pharmaceutically acceptable salts thereof.

15. The method of claim 14, wherein the method of treating bipolar disorder comprises treating the mania of bipolar disorder.

16. The method of claim 14, wherein the method of treating bipolar disorder comprises treating the mania and the cycling bipolar disorder.

17. A method for treating bipolar depression comprising administering to a subject with bipolar depression in need of treatment, a therapeutically effective amount of a compound of formula (I)

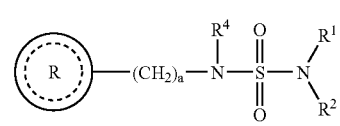 (I)

wherein
$R^1$ and $R^2$ are each independently selected from the group consisting of hydrogen and lower alkyl;
$R^4$ is selected from the group consisting of hydrogen and lower alkyl;
a is an integer from 1 to 2;

is

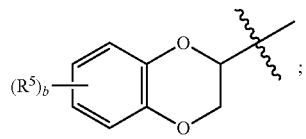

wherein b is an integer from 0 to 4; each $R^5$ is independently selected from the group consisting of halogen, and lower alkyl;
or a pharmaceutically acceptable salt thereof.

18. The method as in claim 17, wherein
$R^1$ and $R^2$ are each independently selected from the group consisting of hydrogen and lower alkyl;

R⁴ is selected from the group consisting of hydrogen and lower alkyl;
a is an integer from 1 to 2;

is

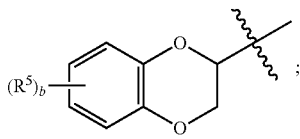

wherein b is an integer from 0 to 2;
each $R^5$ is independently selected from the group consisting of halogen, and lower alkyl;
or a pharmaceutically acceptable salt thereof.

19. The method as in claim 18, wherein
$R^1$ and $R^2$ are each independently selected from the group consisting of hydrogen and lower alkyl;
$R^4$ is selected from the group consisting of hydrogen and methyl;
a is an integer from 1 to 2;

is selected from the group consisting of 2-(2,3-dihydro-benzo[1,4]dioxinyl), 2-(6-chloro-2,3-dihydro-benzo[1,4]dioxinyl), 2-(6-fluoro-2,3-dihydro-benzo[1,4]dioxinyl), 2-(5-fluoro-2,3-dihydro-benzo[1,4]dioxinyl), 2-(7-chloro-2,3-dihydro-benzo[1,4]dioxinyl), 2-(7-methyl-2,3-dihydro-benzo[1,4]dioxinyl), 2-(5-chloro-2,3-dihydro-benzo[1,4]dioxinyl), 2-(6-bromo-2,3-dihydro-benzo[1,4]dioxinyl), 2-(6,7-dichloro-2,3-dihydro-benzo[1,4]dioxinyl), and 2-(8-chloro-2,3-dihydro-benzo[1,4]dioxinyl;
or a pharmaceutically acceptable salt thereof.

20. The method as in claim 19, wherein
$R^1$ and $R^2$ are each independently selected from the group consisting of hydrogen and methyl;
$R^4$ is selected from the group consisting of hydrogen and methyl;
a is an integer from 1 to 2;

is selected from the group consisting of 2-(2,3-dihydro-benzo[1,4]dioxinyl), 2-(6-chloro-2,3-dihydro-benzo[1,4]dioxinyl), 2-(7-chloro-2,3-dihydro-benzo[1,4]dioxinyl), 2-(7-methyl-2,3-dihydro-benzo[1,4]dioxinyl), 2-(6-bromo-2,3-dihydro-benzo[1,4]dioxinyl) and 2-(6,7-dichloro-2,3-dihydro-benzo[1,4]dioxinyl);
or a pharmaceutically acceptable salt thereof.

21. The method of claim 17, wherein the compound of formula (I) is (2S)-(−)-N-(6-chloro-2,3-dihydro-benzo[1,4]dioxin-2-ylmethyl)-sulfamide or a pharmaceutically acceptable salts thereof.

22. A method of treating bipolar depression comprising administering to a subject with bipolar depression in need of treatment, a therapeutically effective amount of (2S)-(−)-N-(6-chloro-2,3-dihydro-benzo[1,4]dioxin-2-ylmethyl)-sulfamide or a pharmaceutically acceptable salts thereof.

23. A method for treating bipolar mania comprising administering to a subject with bipolar mania in need of treatment, a therapeutically effective amount of a compound of formula

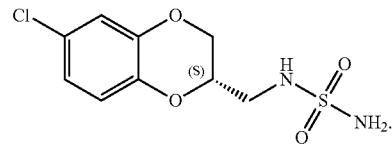

24. A method for treating bipolar disorder comprising administering to a subject with bipolar disorder in need of treatment, a therapeutically effective amount of a compound of formula

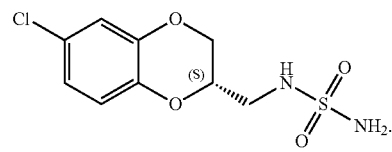

25. A method for treating bipolar depression comprising administering to a subject with bipolar depression in need of treatment, a therapeutically effective amount of a compound of formula

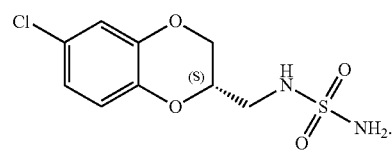

* * * * *